US008846038B2

(12) United States Patent
Nakamura et al.

(10) Patent No.: US 8,846,038 B2
(45) Date of Patent: *Sep. 30, 2014

(54) METHOD FOR TREATING SYNOVIAL SARCOMA

(71) Applicant: Oncotherapy Science, Inc., Toyko (JP)

(72) Inventors: Yusuke Nakamura, Tokyo (JP);
Toyomasa Katagiri, Tokushima (JP);
Chikako Fukukawa, Kawasaki (JP);
Motoki Kuhara, Nagoya (JP)

(73) Assignee: Oncotherapy Science, Inc., Kawasaki-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,599

(22) Filed: Jun. 14, 2013

(65) Prior Publication Data

US 2013/0295108 A1 Nov. 7, 2013

Related U.S. Application Data

(60) Division of application No. 12/769,599, filed on Apr. 28, 2010, now Pat. No. 8,697,068, which is a division of application No. 11/067,231, filed on Feb. 28, 2005, now Pat. No. 7,803,370, which is a continuation-in-part of application No. PCT/JP03/10591, filed on Aug. 21, 2003, said application No. 11/067,231 is a continuation-in-part of application No. PCT/JP2004/002144, filed on Feb. 24, 2004.

(60) Provisional application No. 60/407,506, filed on Aug. 30, 2002, provisional application No. 60/486,195, filed on Jul. 11, 2003, provisional application No. 60/598,834, filed on Aug. 5, 2004, provisional application No. 60/486,195, filed on Jul. 11, 2003.

(51) Int. Cl.
*A61K 39/395* (2006.01)
*C12Q 1/68* (2006.01)
*C07K 16/28* (2006.01)

(52) U.S. Cl.
CPC .......... *C07K 16/28* (2013.01); *C12Q 2600/112* (2013.01); *C12Q 1/6886* (2013.01); *C12Q 2600/106* (2013.01); *C07K 2317/732* (2013.01); *C12Q 2600/136* (2013.01)
USPC ..................................... 424/130.1; 424/277.1

(58) Field of Classification Search
None
See application file for complete search history.

(56) References Cited

U.S. PATENT DOCUMENTS

| 6,964,849 | B2 | 11/2005 | Rastelli et al. | |
|---|---|---|---|---|
| 2003/0044409 | A1 | 3/2003 | Carson et al. | |
| 2003/0215449 | A1* | 11/2003 | Mezes et al. | ............... 424/146.1 |
| 2004/0247593 | A1* | 12/2004 | He et al. | .................... 424/143.1 |

FOREIGN PATENT DOCUMENTS

| WO | WO 96/02641 A2 | 2/1996 |
|---|---|---|
| WO | WO 01/74405 A1 | 10/2001 |
| WO | WO 02/16620 A2 | 2/2002 |
| WO | WO 02/055705 A2 | 7/2002 |
| WO | WO 02/086443 A2 | 10/2002 |
| WO | WO 02/88081 A2 | 11/2002 |
| WO | WO 02/092635 A2 | 11/2002 |
| WO | WO 03/004045 A2 | 1/2003 |
| WO | WO 2004/020668 A2 | 3/2004 |
| WO | WO 2005/004912 A | 1/2005 |

OTHER PUBLICATIONS

Nagayama et al,Oncogen 24:6201-6212, 2005, IDS filed on Jun. 14, 2013, Item 20.*
Chikako Fukukawa et al., Program, Sixty-Third Annual Meeting of the Japanese Cancer Association, Sep. 29-Oct. 1, 2004, Fukuoka.
Fukukawa, Chikako et al., "Therapeutic potential of antibodies against frizzled homologue 10, a cell-surface protein, for synovial sarcoma," Proceedings of the American Association for Cancer Research Annual Meeting, vol. 47, Apr. 2006, p. 465.
Kamarainen et al., Int. J. Cancer, 1998, vol. 76, pp. 487-490.
Koike et al., Biochemical and Biophysical Research Communications, 1999, vol. 262, pp. 39-43.
Nagayama et al., Cancer Research., 2002, vol. 62, pp. 5859-5866.
Nagayama et al., Oncogene, 2005, vol. 24, pp. 6201-6212.
Satoshi Nagayama et al., Gene Expression Profiles of Synovial Sarcoma, The Journal of the Japanese Orthopedic Association, vol. 76, No. 6, Jun. 2002.
Satoshi Nagayama et al., Proceedings Sixty-Second Annual Meeting of the Japanese Cancer Association, Sep. 25-27, 2003, Nagoya.
Search Report issued on Apr. 2, 2012 in corresponding EP application No. 11170198.3.
Tamborini et al., British Journal of Cancer, 2001, vol. 85, No. 3, pp. 405-411.
Terasaki et al., International Journal of Molecular Medicine, 2002, vol. 9, pp. 107-112.

* cited by examiner

*Primary Examiner* — Lei Yao
(74) *Attorney, Agent, or Firm* — Birch, Stewart, Kolasch & Birch, LLP

(57) ABSTRACT

Methods of detecting synovial sarcoma using differentially expressed genes are disclosed. Also disclosed are methods of identifying agents for treating synovial sarcoma. Further, a method for treating or preventing a disease that is associated with Frizzled homologue 10 (FZD10) in a subject is provided.

3 Claims, 26 Drawing Sheets
(2 of 26 Drawing Sheet(s) Filed in Color)

| 214 | GVDVYWSREDKR (SEQ ID NO: 213) |
| 157 | EPTRGSGLFPPLFRPQ (SEQ ID NO: 214) |
| 174 | PHSAQEHPLKDGGPGRGG (SEQ ID NO: 215) |
| 43  | KDIGYNMTRMPNLM (SEQ ID NO: 216) |
| 61  | QREAAIQLHEFA (SEQ ID NO: 217) |
| 189 | RGGCDNPGKFHHVE (SEQ ID NO: 218) |

Fig. 17
157-170 : EPTRGSGLFPPLFR (SEQ ID NO: 219)
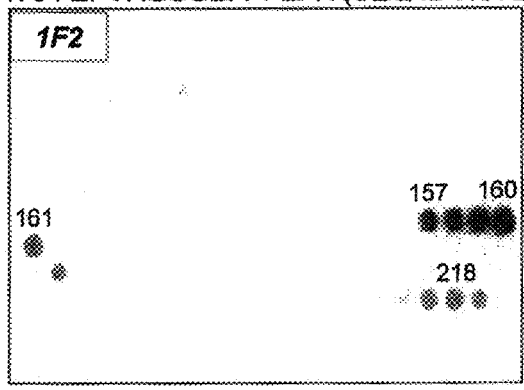
157-170 : EPTRGSGLFPPLFR (SEQ ID NO: 219)
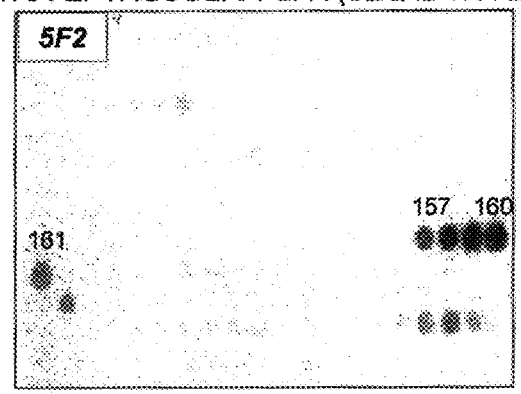
161-173 : GSGLFPPLFRPQR
(SEQ ID NO: 220)
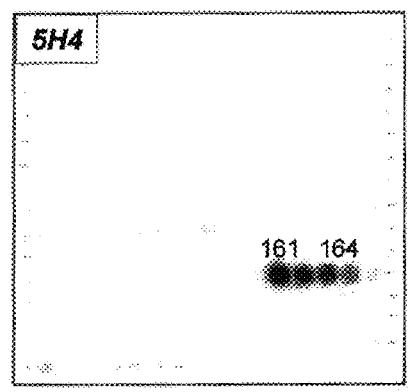
156-169 : DEPTRGSGLFPPLF
(SEQ ID NO: 221)
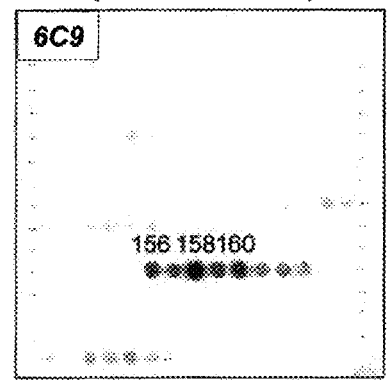

METHOD FOR TREATING SYNOVIAL SARCOMA

CROSS-REFERENCE TO RELATED APPLICATION

This application is a Divisional of application Ser. No. 12/769,599 filed on Apr. 28, 2010, which is a Divisional of U.S. application Ser. No. 11/067,231 filed on Feb. 28, 2005, which has matured into U.S. Pat. No. 7,803,370, and for which priority is claimed under 35 U.S.C. §120.

U.S. Pat. No. 7,803,370 is a Continuation-In-Part of PCT/JP03/10591 filed on Aug. 21, 2003, which claims priority under 35 U.S.C. §119(e) on U.S. Provisional Applications 60/407,506 filed on Aug. 30, 2002, and 60/486,195 filed on Jul. 11, 2003. This application is also a Continuation-In-Part of PCT/JP2004/002144 filed on Feb. 24, 2004, which claims priority under 35 U.S.C. §119(e) on U.S. Provisional Application 60/486,195 filed on Jul. 11, 2003. This application also claims priority under 35 U.S.C. §119(e) on U.S. Provisional Application 60/598,834 filed on Aug. 5, 2004. The entire contents of all of the above applications are hereby incorporated by reference in their entirety.

FIELD OF THE INVENTION

The invention relates to methods of diagnosing synovial sarcoma. Also, the present invention relates to a method for diagnosing Frizzled homologue 10 (FZD10)-associated disease in a subject. Further, the present invention relates to a method for treating and/or preventing FZD10-associated disease in a subject, particularly synovial sarcoma, colorectal cancer, gastric cancer, chronic myeloid leukemia, and acute myeloid leukemia. Furthermore, the present invention relates to a pharmaceutical composition comprising an antibody against FZD10 protein or a fragment thereof, or an double-stranded RNA molecule for FZD10 or an expression vector capable of expressing a double-stranded RNA molecule for FZD10.

BACKGROUND OF THE INVENTION

Soft tissue sarcoma (STS) is one of the difficult diseases both for diagnosis and treatment. STSs are generally classified according to their histological resemblance to mature, normal tissues (Weiss, S. W. and Goldblum, J. R., Enzinger and Weiss's Soft Tissue Tumors, 4th edition. St. Louis: Mosby, 2001). However, some sarcomas such as synovial sarcoma (SS) have no histological counterparts in normal tissues, and therefore are grouped together as "miscellaneous soft tissue tumors" (Weiss, S. W. and Sobin, L., Histological typing of soft tissue tumours, In: World Health Organization International Histological Classification of Tumours, 2nd edition. Berlin: Springer-Verlag, 1994). Synovial sarcoma predominantly affects the lower extremities of adolescents and young adults at 15-40 years of age (Weiss, 2001 supra). The clinicopathological designation was originally given because SS occurs primarily in the vicinity of large joints and histologically resembles developing synovium (Smith, L. W., Synoviomata. Am. J. Pathol., 3: 355, 1927). However, subsequent immunohistochemical and ultrastructural studies (Ghadially, F. N., Ultrastruct. Pathol., 11: 147-51, 1987; Smith, M. E. et al., Histopathology, 26: 279-81, 1995) have revealed significant differences between the tumor cells of SS and synovial cells. In addition, SS can arise where synovial structures are rare or absent, including the lung (Roberts, C. A. et al., Cancer Genet. Cytogenet., 88: 49-52, 1996), heart (Iyengar, V. et al., Arch. Pathol. Lab. Med., 119: 1080-2, 1995), kidney (Argani, P. et al., Am. J. Surg. Pathol., 24: 1087-96, 2000), digestive tract (Billings, S. D. et al., Mod. Pathol., 13: 68-76, 2000), and bone marrow (Hiraga, H. et al., J. Bone Joint Surg. Am., 81: 558-63, 1999). Those data support the hypothesis that SS may originate from cells that are widely distributed in a variety of tissues.

Among several histological findings the most distinctive feature of SS is epithelial differentiation. Based on the presence or absence of an epithelial component, SS is classified into two major subtypes: biphasic, composed of distinct epithelial and spindle tumor cells, and monophasic, occupied by a fibrosarcoma-like spindle tumor cells and no detectable epithelial components (Weiss, 2001 supra). However, as the proportion and features of the epithelial component vary significantly among biphasic tumors, transition from one to the other subtype may be gradual rather than abrupt.

Although the histogenesis of SS remains unclear, molecular analysis of mechanisms underlying tumorigenesis of SS did progress notably with the discovery that a SYT-SSX fusion gene is an SS-specific genetic alteration (Clark, J. et al., Nat. Genet., 7: 502-8, 1994; Skytting, B. et al., J. Natl. Cancer Inst., 91: 974-5, 1999).

On the other hand, molecular target therapy using humanized monoclonal antibodies such as trastuzumab (Herceptin) against ErbB2 (Fendly, B. M. et al., Cancer Res. 50: 1550-8., 1990) and rituximab (Rituxan) against CD20 (Maloney, D. G. et al., Blood. 90: 2188-95., 1997) has recently contributed to the improvement of treatment outcomes in some cases of breast cancer and malignant lymphoma. These promising therapies are the first examples of genomic research-based cancer drugs that bind directly to targeted proteins on the surface of tumor cells. The humanized antibodies are thought to exert an antitumor effect through inhibition of growth signal transduction by the blocking of the cell-surface receptor, and down-regulation of target molecules by interaction with specific antibodies and/or antibody-dependent cell-mediated cytotoxicity (ADCC). Although the precise mechanisms of the antibody-based antitumor effect remain to be elucidated, these therapies are promising alternatives, especially in the treatment of chemoresistant or radioresistant cancers.

Among sarcomas defined as malignant tumors occurring in the mesenchymal tissues, osteosarcomas, Ewing's sarcoma and rhabdmyosarcomas are generally sensitive to chemotherapy. Many other sarcomas, however, especially spindle cell sarcomas in adults, are difficult diseases to treat due to chemo- and radioresistance (Crist, W. M. et al., J Clin Oncol. 19: 3091-102., 2001; Wunder, J. S. et al., J Bone Joint Surg Am. 80: 1020-33., 1998; Ferguson, W. S, and Goorin, A. M., Cancer Invest. 19: 292-315., 2001; Adjuvant chemotherapy for localised resectable soft-tissue sarcoma of adults: meta-analysis of individual data. Sarcoma Meta-analysis Collaboration, Lancet. 350: 1647-54., 1997). SS is a prototype of such tumors, and novel treatment modalities including antibody-based therapy should be developed for further improvement of outcomes, although the prognosis of SS has improved with advances in multidisciplinary treatment.

For the development of antibody-based therapy against target tumors, a critical key is identification of a cell-surface molecule that is overexpressed in the majority of the target tumors and whose expression is absent or minimal in the normal organ tissues. However, it is difficult to identify proteins specifically expressed in tumors, and there have been no reports of such proteins specifically expressed in synovial sarcoma and other tumors against which antibody-based therapies are desired to be established.

SUMMARY OF THE INVENTION

Considering the above problems and demands for developing therapeutics for synovial sarcoma (SS), the present inventors have identified 26 genes that were commonly up-regulated in SS, whose products should be suitable molecular targets for the development of novel therapeutic drugs. Among these up-regulated genes, we selected a candidate gene suitable for the development of molecular target therapy for SS on the basis of the following criteria: (i) expression in the vital organs including brain, heart, lung, liver, kidney and bone marrow was relatively low to avoid critically adverse side effects; and (ii) the gene product has predicted to be the plasma integral membrane protein. Based on these criteria, we focused on one of the cell-surface receptors for the Wnts, Frizzled homologue 10 (FZD10), which belongs to the Frizzled family of seven-pass transmembrane proteins. Although expression of FZD10 has been demonstrated to be up-regulated in primary colorectal cancer (Terasaki, H. et al., Int J Mol. Med. 9: 107-12., 2002) and primary gastric cancer (Kirikoshi, H. et al., Int J. Oncol. 19: 767-71., 2001) as well as SS, the precise biological effects of FZD10 in tumorigenesis remain obscure. Hence, the possible role of FZD10 in tumor growth could potentially be elucidated by inhibition of signal transduction of FZD10.

The invention is based in part the findings that a pattern of gene expression are correlated to a cancerous state, e.g., synovial sarcoma. The genes that are differentially expressed in synovial sarcoma are collectively referred to herein as "SYX nucleic acids" or "SYX polynucleotides" and the corresponding encoded polypeptides are referred to as "SYX polypeptides" or "SYX proteins."

Accordingly, in one aspect, the invention provides a method of diagnosing or determining a predisposition to synovial sarcoma in a subject by determining a level of expression of a synovial sarcoma-associated gene in a patient derived biological sample. By synovial sarcoma-associated gene is meant a gene that is characterized by a level of expression, which differs in a synovial sarcoma cell compared to a normal (or non-synovial sarcoma) cell. A synovial sarcoma-associated gene includes for example SYX 1-26. An alteration, e.g., increase of the level of expression of the gene compared to a normal control level of the gene indicates that the subject suffers from or is at risk of developing synovial sarcoma.

By normal control level is meant a level of gene expression detected in a normal, healthy individual or in a population of individuals known not to be suffering from synovial sarcoma. A control level is a single expression pattern derived from a single reference population or from a plurality of expression patterns. For example, the control level can be a database of expression patterns from previously tested cells.

An increase in the level of SYX 1-26 detected in a test sample compared to a normal control level indicates the subject (from which the sample was obtained) suffers from or is at risk of developing synovial sarcoma.

Alternatively, expression of a panel of synovial sarcoma-associated genes in the sample is compared to a synovial sarcoma control level of the same panel of genes. By synovial sarcoma control level is meant the expression profile of the synovial sarcoma-associated genes found in a population suffering from synovial sarcoma.

A similarity in the level of SYX 1-26 compared to a synovial sarcoma control level indicates the subject suffers from or is at risk of developing synovial sarcoma.

Gene expression is increased 10%, 25%, 50% compared to the normal control level. Alternately, gene expression is increased 1, 2, 5 or more folds compared to the normal control level. Expression is determined by detecting hybridization, e.g., on a chip, of a synovial sarcoma-associated gene probe to a gene transcript of the patient-derived biological sample. Also, the expression can be determined by detecting the protein encoded by the sarcoma-associated gene or the biological activity thereof.

The patient derived biological sample is any sample from a test subject, e.g., a patient known to or suspected of having synovial sarcoma. For example, the sample contains a tumor cell. For example, the sample is a tumor cell from a synovial sarcoma.

In another aspect, the invention also provides a synovial sarcoma reference expression profile of a gene expression level two or more of SYX 1-26.

In other aspect, the invention further provides methods of identifying an agent that inhibits the expression or activity of a synovial sarcoma-associated gene, by contacting a test sample expressing a synovial sarcoma-associated gene with a test agent and determining the expression level of the synovial sarcoma-associated gene. The test sample is a tumor cell such as a tumor cell from synovial sarcoma. A decrease of the level compared to a normal control level of the gene indicates that the test agent is an inhibitor of the synovial sarcoma-associated gene.

The invention also provides a kit comprising a detection reagent which binds to two or more SYX nucleic acids or which binds to a gene product encoded by the nucleic acid sequences. Also provided is an array of nucleic acids that binds to two or more SYX nucleic acids.

In other aspect, the invention further provides a method of screening for a compound for treating or preventing synovial sarcoma, comprising:

(a) contacting a test compound with a polypeptide encoded by a polynucleotide selected from the group consisting of SYX 1-26;

(b) detecting the binding activity of the test compound to the polypeptide; and (c) selecting the compound that binds to the polypeptide.

In another embodiment, the method of screening for a compound for treating or preventing synovial sarcoma of the present invention comprises:

(a) contacting a test compound with a cell expressing one or more marker genes, wherein the marker genes are selected from the group consisting of SYX 1-26; and (b) selecting a compound that reduces the expression level of the marker genes as compared to a control.

In yet another embodiment, the method of screening for a compound for treating or preventing synovial sarcoma of the invention comprises:

(a) contacting a test compound with a cell into which a vector comprising the transcriptional regulatory region of one or more marker genes and a reporter gene that is expressed under the control of the transcriptional regulatory region has been introduced, wherein the one or more marker genes are selected from the group consisting of SYX 1-26;

(b) measuring the activity of the reporter gene; and (c) selecting a compound that reduces the expression level of the reporter gene when the marker gene is an up-regulated marker gene selected from the group consisting of SYX 1-26 as compared to a control.

In an additional embodiment, the method of screening for a compound for treating or preventing synovial sarcoma of the invention comprises:

(a) contacting a test compound with a polypeptide encoded by a polynucleotide selected from the group consisting of SYX 1-26;

(b) detecting the biological activity of the polypeptide of step (a); and (c) selecting a compound that suppresses the biological activity of the polypeptide encoded by the polynucleotide in comparison with the biological activity detected in the absence of the test compound.

In other aspect, the present invention provides a method for treating or preventing synovial sarcoma in a subject, comprising administering to the subject a pharmaceutically effective amount of the compound obtained by any one of screening method described above.

In further aspect, the present invention provides a composition for treating or preventing synovial sarcoma, wherein the composition comprises a pharmaceutically effective amount of the compound obtained by any one of screening method described above as an active ingredient, and a pharmaceutically acceptable carrier.

Further, the present inventors successfully demonstrated that knockdown of the expression of FZD10 gene via RNA interference resulted in the growth suppression of SS cells, indicating that FZD10 plays an important role in the cell growth of SS.

So, in one aspect, the present invention provides a method for inhibiting or reducing an expression of FZD10 gene in a cell or tissue in vitro, in vivo or ex vivo, comprising introducing into the cell or tissue a double-stranded RNA molecule for FZD10 or an expression vector capable of expressing a double-stranded RNA molecule for FZD10, wherein the double-stranded RNA molecule for FZD10 comprises a nucleotide sequence targeted to the 10 to 100 continuous nucleotides, preferably 10 to 50 continuous nucleotides, more preferably 10 to 30 continuous nucleotides of SEQ ID NO:154. Preferably, the double-stranded RNA molecule for FZD10 may comprise a short nucleotide sequence as a short-interfering RNA (siRNA). For example, the double-stranded RNA molecule comprises a nucleotide sequence targeted to nucleotides nos. 1481 to 1499 (SEQ ID No. 203) or nucleotides nos. 1595 to 1613 (SEQ ID No. 204) of SEQ ID No. 154. More specifically, the double-stranded RNA molecule for FZD10 can be expressed by the expression vector having the sequence of SEQ ID Nos. 195, 196, 197, or 198.

In other aspect, the present invention provides a method for preventing or treating synovial sarcoma in a subject, comprising administering therapeutically effective amount of a double-stranded RNA for FZD10 or an expression vector capable of expressing a double-stranded RNA for FZD10 to the subject.

Moreover, the present inventors generated a specific polyclonal antibody (TT641 pAb) and monoclonal antibodies (mAbs) that recognized the N-terminal extracellular domain of FZD10 (FZD10-ECD) for the development of antibody-based therapy for synovial sarcoma (SS). As the above-mentioned criteria for selection of molecular targets, the present inventors revealed that the expression of FZD10 was absent or low in normal vital organs except epithelia in some organ tissues with immunohistochemical analysis using TT641 pAb. Moreover, it was demonstrated by the present inventors that this specific antibody was effective in mediating antibody-dependent cell-mediated cytotoxicity (ADCC) against FZD10-overexpressing SS cells. In addition, in vivo experiments using nude mice successfully showed that intratumoral injection of TT641 pAb attenuated the growth of SS xenografts presumably through induction of apoptosis of tumor cells.

Based on the above findings, the present inventors concluded that the antibody for FZD10 has therapeutic potential in the treatment and diagnosis of SS and other FZD10-overexpressing tumors. Also, the present invention is based on the findings that FZD10 is specifically expressed in certain tumors including synovial sarcoma, and that these tumors can be detected using the specific antibody for FZD10.

In one aspect, the present invention provides a method for treating or preventing a disease that is associated with Frizzled homologue 10 (FZD10) in a subject, comprising administering to the subject an effective amount of an antibody against FZD10 protein or a fragment thereof "The disease that is associated with FZD10" (FZD10-associated disease) refers to a disease that is associated with overexpression of FZD10 protein. Such diseases include, but are not limited to, synovial sarcoma (SS), colorectal cancer, gastric cancer, chronic myeloid leukemia (CML), and acute myeloid leukemia (AML).

The antibody used in the present method may be a polyclonal or monoclonal antibody. Preferably, the antibody is raised against a peptide comprising at least 5 amino acid residues of an amino acid sequence shown in SEQ ID NO: 153, especially a peptide comprising at least residues 43-56, 61-72, 156-169, 157-170, 157-172, 161-173, 174-191, 189-202, 214-225, or 1-225 of an amino acid sequence shown in SEQ ID NO: 153.

Furthermore, in another aspect, the present invention provides a method for diagnosis or prognosis of a disease that is associated with Frizzled homologue 10 (FZD10) or of a predisposition to develop the disease in a subject, comprising (a) contacting a sample from the subject with an antibody against FZD10 protein or a fragment thereof;

(b) detecting the FZD10 protein in the sample; and (c) judging whether or not the subject suffers from or is at risk of developing the disease based on the relative abundance of the FZD10 protein compared to a control.

"The disease that is associated with FZD10" (FZD10-associated disease) refers to a disease associated with overexpression of FZD10 protein. Such diseases include, but are not limited to, synovial sarcoma (SS), colorectal cancer, gastric cancer, chronic myeloid leukemia (CML), and acute myeloid leukemia (AML). The antibody used in the present method may be a polyclonal or monoclonal antibody. Preferably, the antibody is raised against a peptide comprising at least 5 amino acid residues of an amino acid sequence shown in SEQ ID NO: 153, especially a peptide comprising at least residues 43-56, 61-72, 156-169, 157-170, 157-172, 161-173, 174-191, 189-202, 214-225, or 1-225 of an amino acid sequence shown in SEQ ID NO: 153.

Still further, the present invention provides a pharmaceutical composition for treating or preventing a disease associated with Frizzled homologue 10 (FZD10), comprising an antibody or a fragment thereof which is raised against a peptide comprising at least 5 amino acid residues of an amino acid sequence shown in SEQ ID NO: 153, and a pharmaceutically acceptable carrier or excipient.

Still further, the present invention provides a kit for diagnosis or prognosis of a disease associated with Frizzled homologue 10 (FZD10), comprising an antibody or a fragment thereof raised against a peptide comprising at least 5 amino acid residues of an amino acid sequence shown in SEQ ID NO: 153.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7A are photographs showing western blot analyses of FZD10 in several tumor cell lines: SS cell lines (HS-SY-2 and YaFuSS), colon cancer cell lines (SW480, LoVo, DLD1, HT29, HCT116, SNU-C4 and SNU-05), cervical adenocarcinoma cell line (HeLa) and fibrosarcoma cell line (HT1080). β-actin expression was used as a loading control.

FIG. 7B are photographs showing semi-quantitative RT-PCR analyses of the FZD gene family in the same tumor cell lines as those examined in FIG. 7A. Expression of β2-microglobulin gene (β2MG) served as an internal control. FZD family members were placed in order of the homology of amino acid sequences to FZD10-ECD; FZD9 was the most homologous to FZD10-ECD.

FIG. 8A is a photograph showing western blots indicating the establishment of COST-FZD10 cells, which stably over-expressed FZD10. S5, S9, S10, S3 and S11 were representatives of COST-FZD10 stable transfectant cells, and exogenously expressed products were the same size as endogenous FZD10 expressed in the SS cell lines, HS-SY-2 and YaFuSS.

FIG. 8B are photographs showing an immunocytochemical staining using anti-myc antibody and the TT641 pAb. The left panel shows a cell immunostained with Texas Red-conjugated anti-myc. The middle panel shows the same cell treated with TT641 pAb (Alexa Flour 488), and both signals are overlaid in the double-color image as a yellow signal (right panel).

FIG. 8C are photographs showing an immunocytochemical staining with TT641 pAb for the detection of endogenous FZD10 in SS cell lines (HS-SY-2 and YaFuSS).

FIG. 17 are photographs showing epitope mapping of mAbs, 1F2, 5F2, 5H4 and 6C9 with synthetic overlapping linear peptides.

DETAILED DESCRIPTION AND PREFERRED EMBODIMENTS OF THE PRESENT INVENTION

The present invention is based in part on the findings of changes in expression patterns of multiple nucleic acid sequences in endothelial cells from patients with sarcoma. The differences in gene expression were identified by using a comprehensive cDNA microarray system.

1. Gene Expression Profiles
1.1. Determining Gene Expression Profiles

Gene-expression profiles of a panel of synovial sarcoma (SS) cases were analyzed using a genome-wide cDNA microarray containing 23,040 genes. In addition to SS, gene-expression profiles were analyzed among four other types of soft tissue sarcomas (STS), including malignant fibrous histiocytoma (MFH), leiomyosarcoma (LMS), pleomorphic and dedifferentiated liposarcoma (PLS and DLS), and malignant peripheral nerve sheath tumor (MPNST). These tumors exhibit histological features that closely resemble those of SS.

Figure 2:
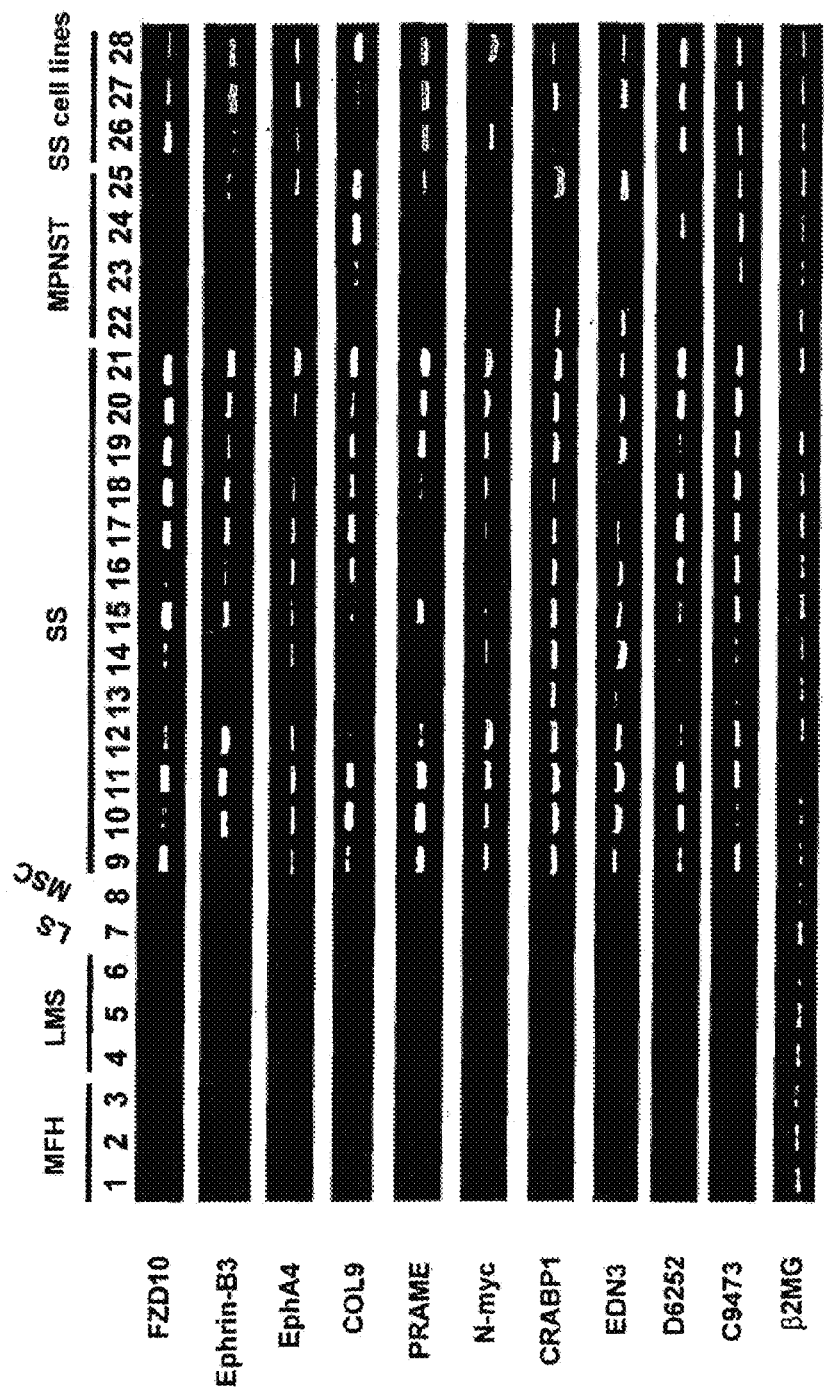
FIG. 2 is a photograph of a blot showing the results of semiquantitative RT-PCR analyses of 10 representative up-regulated genes common to STS in 3 MFH (lanes 1-3), 3 LMS (lanes 4-6), 1 LS (lanes 7), 1 MSC (lanes 8), 13 SS (lanes 9-21), 4 MPNST (lanes 22-25) cases and three SS cell lines (lanes 26-28). Many of the genes were also expressed in MPNST at the same or lower levels, compared to SS. β2MG, β2 microglobulin (internal control).

Twenty-six genes, including four ESTs were identified, that were commonly up-regulated in SS (Table A). Among them Frizzled homolog 10 (C0671) and one EST (A8647) were up-regulated specifically in SS; the remaining 24 genes were also expressed in MPNST, at the same or lower levels. The results of semi-quantitative RT-PCR experiments confirmed the specific expression of these genes in SS, or SS and MPNST (FIG. 2). In addition, expression of all 26 genes was detected in three SS cell lines, indicating that this activity was intrinsic to SS cells and not induced by in vivo environments.

The differentially expressed genes identified herein are used for diagnostic purposes and to develop gene targeted therapeutic approaches to treating synovial sarcoma.

The genes whose expression levels are increased in synovial sarcoma patients are summarized in Table A and are collectively referred to herein as "synovial sarcoma-associated genes", "SYX nucleic acids" or "SYX polynucleotides" and the corresponding encoded polypeptides are referred to as "SYX polypeptides" or "SYX proteins." Unless indicated otherwise, "SYX" is meant to refer to any of the sequences disclosed herein (e.g., SYX 1-26). The genes have been previously described and are presented along with a database accession number.

By measuring expression of the various genes in a sample of cells, synovial sarcoma can be determined in a cell or population of cells. Similarly, by measuring the expression of these genes in response to various agents, agents for treating synovial sarcoma can be identified.

TABLE A

Up-regulated genes common to Synovial Sarcoma

| ID | Hs. | GENE | SYX Assignment |
|---|---|---|---|
| C0671 | 31664 | frizzled homolog 10 | 1 |
| A8647 | 105805 | EST | 2 |
| A0102 | 1408 | endothelin 3 | 3 |
| A5094N | 53563 | collagen, type IX, alpha 3 | 4 |
| A0623 | 144879 | dual specificity phosphatase 9 | 5 |
| B9059 | 25960 | N-myc | 6 |
| A6384 | 346950 | cellular retinoic acid-binding protein 1 | 7 |
| A0277 | 26988 | ephrin-B3 | 8 |
| A5044 | 31439 | serine protease inhibitor, Kunitz type, 2 | 9 |
| C0488 | 30743 | preferentially expressed antigen in melanoma | 10 |

TABLE A-continued

Up-regulated genes common to Synovial Sarcoma

| ID | Hs. | GENE | SYX Assignment |
|---|---|---|---|
| A2246 | 73964 | EphA4 | 11 |
| A0650 | 49585 | fibroblast growth factor 18 | 12 |
| C1372 | 256311 | granin-like neuroendocrine peptide precursor | 13 |
| E1451 | 198760 | neurofilament, heavy polypeptide (200 kD) | 14 |
| A2691N | 2877 | cadherin 3, type 1, P-cadherin (placental) | 15 |
| B9201 | 284122 | WNT inhibitory factor1 | 16 |
| A2029 | 79404 | neuron-specific protein | 17 |
| C9473 | 92732 | *Homo sapiens* X28 region near ALD locus | 18 |
| A8857 | 11849 | Hypothetical protein MGC15827 | 19 |
| C5852 | 55407 | *Homo sapiens* cDNA DKFZp434K0621 | 20 |
| A5313 | BC009491 | clone MGC 16382 | 21 |
| D6309 | 129010 | EST | 22 |
| D6252 | 128899 | EST | 23 |
| C9468 | 92679 | *Homo sapiens* clone CDABP0014 | 24 |
| B8437 | 24583 | hypothetical protein DKFZp434C0328 | 25 |
| B7503 | 12714 | EST | 26 |

Italic ID; Highly specific to SS.
Hs.; UniGene accession number.

The invention involves determining (e.g., measuring) the expression of at least one, and up to all the SYX sequences listed in Table A. Using sequence information provided by the GeneBank database entries for the known sequences the synovial sarcoma-associated genes are detected and measured using techniques well known to one of ordinary skill in the art. For example, sequences within the sequence database entries corresponding to SYX sequences, can be used to construct probes for detecting SYX RNA sequences in, e.g., Northern blot hybridization analysis. Alternatively, the sequences can be used to construct primers for specifically amplifying the SYX sequences in, e.g, amplification-based detection methods such as reverse-transcription based polymerase chain reaction.

Expression level of one or more of the synovial sarcoma-associated genes in the test cell population, e.g., a patient derived biological sample is then compared to expression levels of the some genes in a reference population. The reference cell population includes one or more cells for which the compared parameter is known, i.e., the cell is cancerous or noncancerous such as a mesenchymal stem cell.

Whether or not a pattern of gene expression levels in the test cell population compared to the reference cell population indicates cancer or predisposition thereto depends upon the composition of the reference cell population. For example, if the reference cell population is composed of non-cancerous cells, a similar gene expression pattern in the test cell population and reference cell population indicates the test cell population is non-cancerous. Conversely, if the reference cell population is made up of cancerous cells, a similar gene expression profile between the test cell population and the reference cell population indicates that the test cell population includes cancerous cells.

A level of expression of synovial sarcoma-associated genes in a test cell population can be considered altered in levels of expression if its expression level varies from the reference cell population by more than 1.0, 1.5, 2.0, 5.0, 10.0 or more folds from the expression level of the corresponding synovial sarcoma-associated genes in the reference cell population.

If desired, comparison of differentially expressed genes between a test cell population and a reference cell population can be done with respect to a control nucleic acid whose expression is independent of the parameter or condition being measured. For example, a control nucleic acid is one which is known not to differ depending on the malignant or non-malignant state of the cell. Expression levels of the control nucleic acid in the test and reference nucleic acid can be used to normalize signal levels in the compared populations. Control genes can be, e.g., β-actin, glyceraldehyde 3-phosphate dehydrogenase or ribosomal protein P1.

The test cell population is compared to multiple reference cell populations. Each of the multiple reference populations may differ in the known parameter. Thus, a test cell population may be compared to a second reference cell population known to contain, e.g., synovial sarcoma cells, as well as a second reference population known to contain, e.g., non-synovial sarcoma cells such as mesenchymal stem cells or epithelial cells. The test cell is included in a tissue type or cell sample from a subject known to contain, or to be suspected of containing, synovial sarcoma cells.

The test cell is obtained from a bodily tissue or a bodily fluid, e.g., biological fluid (such as synovial fluid, blood or urine). For example, the test cell is purified from synovial fluid or another tissue. Preferably, the test cell population comprises a tumor cell.

Cells in the reference cell population are derived from a tissue type as similar to test cell, e.g., a synovial sarcoma cell line (positive control) or a normal non-synovial sarcoma cell line (negative control). Alternatively, the control cell population is derived from a database of molecular information derived from cells for which the assayed parameter or condition is known.

The subject is preferably a mammal. The mammal can be, e.g., a human, non-human primate, mouse, rat, dog, cat, horse, or cow.

Expression of the genes disclosed herein is determined at the RNA level using any method known in the art. For example, Northern hybridization analysis using probes which specifically recognize one or more of these nucleotide sequences can be used to determine gene expression. Alternatively, expression is measured using reverse-transcription-based PCR assays, e.g., using primers specific for the differentially expressed sequences.

Expression is also determined at the protein level, i.e., by measuring the levels of polypeptides encoded by the gene products described herein, as well as biological activity thereof. Such methods are well known in the art and include, e.g., immunoassays based on antibodies to proteins encoded by the genes. The biological activities of the proteins encoded by the genes are also well known.

1.2. Diagnosing Synovial Sarcoma

Synovial sarcoma is diagnosed by measuring the level of expression of one or more SYX nucleic acids in a biological sample including a test population of cells, (i.e., a patient derived biological sample) that contain or suspected to contain a synovial sarcoma cell. The "biological sample" is not specifically limited, as long as it is a biological sample that is derived from a subject to be diagnosed. Examples of the sample include cell or organ, and tissue sections, as well as bodily fluids. Preferably, the biological sample comprises a tumor cell. Most preferably, the biological sample comprises a tumor cell from a synovial sarcoma tumor. Gene expression is also measured from blood or other bodily fluids such as urine. These biological samples can be used for measuring the expression level of the SYX nucleic acids in protein level. For example, the protein level in the biological sample such as blood or serum derived from subject to be diagnosed can be measured by immunoassay or biological assay well-known in the art.

Expression of one or more of a synovial sarcoma-associated gene, e.g., SYX 1-26 is determined in the biological sample and compared to the expression of the normal control level. Preferably, the level of expression of SYX 1 and SYX 2 is determined. By normal control level is meant the expression profile of the synovial sarcoma-associated genes typically found in a population not suffering from synovial sarcoma. An increase of the level of expression of the synovial sarcoma-associated genes in the patient derived biological sample indicates that the subject is suffering from or is at risk of developing synovial sarcoma. For example, an increase in expression of SYX 1-26 in the test population compared to the normal control level indicates that the subject is suffering from or is at risk of developing synovial sarcoma.

When one or more of the synovial sarcoma-associated genes are altered in the biological sample compared to the normal control level indicates that the subject suffers from or is at risk of developing synovial sarcoma. For example, 50%, 60%, 80%, 90% or more of the synovial sarcoma-associated genes are altered.

Alternatively, if the expression profile of the synovial sarcoma-associated genes in the biological sample is compared to the expression profile of a population suffering from synovial sarcoma, a similar expression of SYX 1-26 indicates that the subject is suffering from synovial sarcoma.

1.3. Identifying Agents that Inhibit Synovial Sarcoma-Associated Gene Expression An agent that inhibits the expression or activity of a synovial sarcoma-associated gene is identified by contacting a test sample expressing a synovial sarcoma-associated gene with a test agent and determining the expression level of the synovial sarcoma-associated gene. A decrease in expression compared to the normal control level indicates the agent is an inhibitor of a synovial sarcoma-associated gene.

The test sample may be any sample expressing the synovial sarcoma-associated genes. For example, the test sample comprises a tumor cell. Preferably, the tumor cell is derived from the synovial sarcoma. For example, the test sample is an immortalized cell line derived from an adenocarcinoma cell. Alternatively, the test sample is a cell, which has been transfected with a synovial sarcoma-associated gene or which has been transfected with a regulatory sequence (e.g. promoter sequence) from a synovial sarcoma-associated gene operably linked to a reporter gene.

An agent can be identified by combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection.

1.4. Assessing Efficacy of Treatment of Synovial Sarcoma in a Subject

The differentially expressed synovial sarcoma-associated gene identified herein also allow for the course of treatment of synovial sarcoma to be monitored. In this method, a test sample is provided from a subject undergoing treatment for synovial sarcoma. If desired, test samples are obtained the subject at various time points before, during, or after treatment. Expression of one or more of the synovial sarcoma-associated gene, in the sample is then determined and compared to a reference sample which includes cells whose synovial sarcoma state is known. Preferably, the reference samples have not been exposed to the treatment.

If the reference sample contains no synovial sarcoma cells, a similarity in expression between synovial sarcoma-associated gene in the test sample and the reference sample indicates that the treatment is efficacious. However, a difference in expression between synovial sarcoma-associated gene in the test sample and this reference sample indicates the treatment is not efficacious.

By "efficacious" is meant that the treatment leads to a decrease in size, prevalence, or metastatic potential of synovial sarcoma tumors in a subject. When treatment is applied prophylactically, "efficacious" means that the treatment retards or prevents synovial sarcoma tumors from forming Efficaciousness is determined in association with any known method for diagnosing or treating synovial sarcoma. Synovial sarcoma is diagnosed for example, by identifying histological anomalies, e.g., epithelial differentiation, along with molecular identification of SYT-SSX fusion gene.

1.5. Selecting a Therapeutic Agent for Treating Synovial Sarcoma that is Appropriate for a Particular Individual Differences in the genetic makeup of individuals can result in differences in their relative abilities to metabolize various drugs. An agent that is metabolized in a subject to act as an anti-synovial sarcoma agent can manifest itself by inducing a change in gene expression pattern in the subject-derived sample from that characteristic of a synovial sarcomal state to a gene expression pattern characteristic of a non-synovial sarcomal state. Accordingly, the differentially expressed synovial sarcoma-associated gene disclosed herein allow for a putative therapeutic or prophylactic anti-synovial sarcoma agent to be tested in a test sample from a selected subject in order to determine if the agent is a suitable inhibitor of synovial sarcoma in the subject.

To identify an inhibitor of synovial sarcoma, that is appropriate for a specific subject, a test sample from the subject is exposed to a therapeutic agent, and the level of expression of one or more of SYX 1-26 genes is determined.

The test sample contains a synovial sarcoma cell expressing a synovial sarcoma-associated gene. Preferably, the test sample is a tumor cell from a synovial sarcoma. For example, a test sample is incubated in the presence of a candidate agent and the pattern of gene expression of the test sample is measured and compared to one or more reference profiles, e.g., a synovial sarcoma reference expression profile or a non-synovial sarcoma reference expression profile.

If the reference sample is a synovial sarcoma cell, a similarity in gene expression patterns between the test sample and the reference sample indicates the agent is not suitable for treating synovial sarcoma in the subject.

A decrease in expression of one or more of SYX 1-26 in a test sample relative to a reference sample containing synovial sarcoma is indicative that the agent is therapeutic.

The test agent can be any compound or composition. In some embodiments the test agents are compounds and compositions know to be anti-cancer agents.

1.6. Screening Assays for Identifying a Candidate Therapeutic Agent for Treating or Preventing Synovial SARCOMA The differentially expressed genes disclosed herein can also be used to identify candidate therapeutic agents for treating a synovial sarcoma. The method is based on screening a candidate therapeutic agent to determine if it converts an expression profile of SYX 1-26 characteristic of a synovial sarcoma state to a pattern indicative of a non-synovial sarcoma state.

In the method, a cell is exposed to a test agent or a combination of test agents (sequentially or consequentially) and the expression of one or more SYX 1-26 in the cell is measured.

The expression profile of the synovial sarcoma-associated genes in the test population is compared to expression level of the synovial sarcoma-associated genes in a reference cell population that is not exposed to the test agent.

The test agent can be a compound not previously described or can be a previously known compound but which is not known to be an anti-synovial sarcoma agent. An agent effective in suppressing expression of over-expressed genes can be further tested for its ability to prevent synovial sarcoma tumor growth, and is a potential therapeutic useful for the treatment of synovial sarcoma. Further evaluation of the clinical usefulness of such a compound can be performed using standard methods of evaluating toxicity and clinical effectiveness of anti-cancer agents.

In a further embodiment, the present invention provides methods of screening for candidate agents which are potential targets in the treatment or prevention of synovial sarcoma. As discussed in detail above, by controlling the expression levels or activities of marker genes, one can control the onset and progression of synovial sarcoma. Thus, candidate agents, which are potential targets in the treatment or prevention of synovial sarcoma, can be identified by screening test compounds using the expression levels and/or activities of marker genes as indices. In the context of the present invention, such screening may comprise, for example, the following steps:

(a) contacting a test compound with a polypeptide encoded by at least one of the polynucleotide of SYX 1-26;

(b) detecting the binding activity of the test compound to the polypeptide; and (c) selecting a compound that binds to the polypeptide.

Alternatively, the screening method of the present invention may comprise the following steps:

(a) contacting a candidate compound with a cell expressing one or more marker genes, wherein the marker genes are selected from the group consisting of SYX 1-26; and (b) selecting a compound that reduces the expression level of the marker genes as compared to a control.

Cells expressing a marker gene include, for example, cell lines established from synovial sarcoma; such cells can be used for the above screening of the present invention.

The expression of the marker gene can be determined by, for example, using the expression of a reporter gene. Accordingly, the screening method of the present invention may comprise the following steps:

(a) contacting a candidate compound with a cell into which a vector comprising the transcriptional regulatory region of one or more marker genes and a reporter gene that is expressed under the control of the transcriptional regulatory region has been introduced, wherein the one or more marker genes are selected from the group consisting of SYX 1-26;

(b) measuring the activity of the reporter gene; and (c) selecting a compound that reduces the expression level of the reporter gene when the marker gene is an up-regulated marker gene selected from the group consisting of SYX 1-26 as compared to a control.

Suitable reporter genes and host cells are well-known in the art. The reporter construct used in the screening method can be prepared by using the transcriptional regulatory region of a marker gene. When the transcriptional regulatory region of a marker gene has been known to those skilled in the art, a reporter construct can be prepared by using the previously elucidated sequence information. When the transcriptional regulatory region of a marker gene remains unidentified, a nucleotide segment containing the transcriptional regulatory region can be isolated from a genome library based on the nucleotide sequence information of the marker gene.

Alternatively, the screening method of the present invention may comprise the following steps:

(a) contacting a test compound with a polypeptide encoded by a polynucleotide selected from the group consisting of SYX 1-26;

(b) detecting the biological activity of the polypeptide of step (a); and (c) selecting a compound that suppresses the biological activity of the polypeptide encoded by the polynucleotide in comparison with the biological activity detected in the absence of the test compound.

A protein used in the screening method can be obtained as a recombinant protein using the nucleotide sequence of the SYX 1-26. Based on the information of the nucleotide sequence, one skilled in the art can select any suitable biological activity of the protein as an index for screening the compound of interest.

The compound obtained by any of the above screening methods may be a candidate for drugs that inhibit the activity of the protein encoded by synovial sarcoma-associated genes (SYX 1-26) and can be applied to the treatment or prevention of synovial sarcoma.

Moreover, when the compound may be a polynucleotide or polypeptide, the compound in which a part of the structure of the compound inhibiting the activity of proteins encoded by SYX 1-26 is altered by addition, deletion and/or replacement of one or more nucleotides or amino acids of the compound are also included in the compounds obtainable by the screening method of the present invention.

When administrating the compound isolated by the method of the invention as a pharmaceutical for mammals, such as humans, mice, rats, guinea-pigs, rabbits, cats, dogs, sheep, pigs, cattle, monkeys, baboons, and chimpanzees, preferably humans, the isolated compound can be directly administered or can be formulated into a dosage form using known pharmaceutical preparation methods. For example, according to need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; and flavoring agents such as peppermint, Gaultheria adenothrix oil and cherry. When the unit-dose form is a capsule, a liquid carrier, such as an oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80™ and HCO-50.

Sesame oil or Soy-bean oil can be used as a oleaginous liquid and may be used in conjunction with benzyl benzoate or benzyl alcohol as a solubilizer and may be formulated with a buffer, such as phosphate buffer and sodium acetate buffer; a pain-killer, such as procaine hydrochloride; a stabilizer, such as benzyl alcohol and phenol; and an anti-oxidant. The prepared injection may be filled into a suitable ampule.

Methods well-known to one skilled in the art may be used to administer the pharmaceutical composition of the present invention to patients, for example as intraarterial, intravenous, or percutaneous injections and also as intranasal, transbronchial, intramuscular or oral administrations. The method of administration varies according to the body-weight and age of a patient and the administration method; however, one skilled in the art can routinely select a suitable method of administration. If the compound is encoded by a DNA, the DNA can be inserted into a vector for gene therapy and the vector administered to a patient to perform the therapy.

The composition can be administered in a pharmaceutically effective amount. The "pharmaceutically effective amount" may vary according to the body-weight, age, and symptoms of the patient, as well as the method of administration and the dosage form, but one skilled in the art can suitably select them. For example, although the dose of a compound that binds to the protein encoded by a synovial sarcoma-associated gene and regulates its activity depends on various factors including the symptoms, the dose may be about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously apply a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

1.7. Assessing the Prognosis of a Subject with Synovial Sarcoma

Also provided is a method of assessing the prognosis of a subject with synovial sarcoma by comparing the expression of one or more synovial sarcoma-associated genes in a test sample to the expression of the genes in a reference sample derived from patients over a spectrum of disease stages. By comparing gene expression of one or more synovial sarcoma-associated genes in the test sample and the reference sample(s), or by comparing the pattern of gene expression overtime in test samples derived from the subject, the prognosis of the subject can be assessed.

The reference sample includes primarily non-synovial sarcoma or synovial sarcoma cells. Alternatively, the reference sample may be a synovial sarcoma or non-synovial sarcoma expression profile.

Alternatively, when a reference sample includes primarily non-synovial sarcoma cells, an increase in expression of one or more of SYX 1-26 indicates a less favorable prognosis in the subject, while a similar expression indicates a more favorable prognosis.

1.8. Kits

The invention also includes an SYX-detection reagent, e.g., nucleic acids that specifically identify one or more SYX nucleic acids by having homologous nucleic acid sequences, such as oligonucleotide sequences, complementary to a portion of the SYX nucleic acids or antibodies to proteins encoded by the SYX nucleic acids packaged together in the form of a kit. The kit may contain in separate containers a nucleic acid or antibody (either already bound to a solid matrix or packaged separately with reagents for binding them to the matrix), control formulations (positive and/or negative), and/or a detectable label. Instructions (e.g., written, tape, VCR, CD-ROM, etc.) for carrying out the assay may be included in the kit. The assay may, for example, be in the form of a Northern hybridization or a sandwich ELISA as known in the art.

For example, SYX detection reagent is immobilized on a solid matrix such as a porous strip to form at least one SYX detection site. The measurement or detection region of the porous strip may include a plurality of sites containing a nucleic acid. A test strip may also contain sites for negative and/or positive controls. Alternatively, control sites are located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of SYX present in the sample. The detection sites may be configured in any suitably detectable shape and are typically in the shape of a bar or dot spanning the width of a test strip.

Alternatively, the kit contains a nucleic acid substrate array comprising one or more nucleic acids. The nucleic acids on the array specifically identify one or more nucleic acid sequences represented by SYX 1-26. In various embodiments, the expression of 2, 3, 4, 5, 6, 7, 8, 9, 10, 15, 20, or 25, or more of the nucleic acids represented by SYX 1-26 are identified by virtue if binding to the array. The substrate array can be on, e.g., a solid substrate, e.g., a "chip" as described in U.S. Pat. No. 5,744,305.

1.9. Arrays and Pluralities

The invention also includes a nucleic acid substrate array comprising one or more nucleic acids. The nucleic acids on the array specifically identify one or more nucleic acid sequences represented by SYX 1-26. In various embodiments, the expression of 2, 3, 4, 5, 6, 7, 8, 9, 10, 15, 20, or 25 or more of the nucleic acids represented by SYX 1-26 are identified by detecting nucleic acid binding to the array.

The invention also includes an isolated plurality (i.e., a mixture if two or more nucleic acids) of nucleic acids. The nucleic acid is in a liquid phase or a solid phase, e.g., immobilized on a solid support such as a nitrocellulose membrane. The plurality typically includes one or more of the nucleic acids represented by SYX 1-26. In various embodiments, the plurality includes 2, 3, 4, 5, 6, 7, 8, 9, 10, 15, 20, or 25 or more of the nucleic acids represented by SYX 1-26.

2. Therapeutics Based on the Analysis of Gene Expression Profiles 2.1. Methods of Treating Synovial Sarcoma The invention provides a method for treating or preventing a synovial sarcoma in a subject. Administration can be prophylactic or therapeutic to a subject at risk of (or susceptible to) a disorder or having a disorder associated with aberrant expression or activity of the herein described differentially expressed sequences (e.g., SYX 1-26).

The therapeutic method involves decreasing the expression, or function, or both, of one or more gene products of genes whose expression is increased ("over-expressed gene") in a synovial sarcoma cell as compared to a non-synovial sarcoma cell. Expression can be inhibited in any of several ways known in the art. For example, expression is inhibited by administering to the subject a nucleic acid that inhibits, or antagonizes, the expression of the over-expressed gene or genes. In one embodiment, the therapeutic method can be achieved using antisense method or RNA interference, that is, an antisense polynucleotide or a double-stranded RNA can be administered which disrupts expression of the gene or genes.

Alternatively, function of one or more gene products of the over-expressed genes can be inhibited by administering a compound that binds to or otherwise inhibits the function of the gene products. The compound can be, e.g., an antibody to the over-expressed gene product or gene products.

As noted above, antisense polynucleotide corresponding to the nucleotide sequence of SYX 1-26 can be used to reduce the expression level of the SYX 1-26. Antisense polynucleotide corresponding to SYX 1-26 that are up-regulated in synovial sarcoma are useful for the treatment of synovial sarcoma. Specifically, the antisense nucleic acids of the present invention may act by binding to the SYX 1-26 or mRNAs corresponding thereto, thereby inhibiting the transcription or translation of the genes, promoting the degradation of the mRNAs, and/or inhibiting the expression of proteins encoded by the SYX 1-26, finally inhibiting the function of the proteins. More specifically, such antisense polynucleotide include those comprising the nucleotide sequence of SEQ ID NO: 90 for suppressing expression of SYX 10; SEQ ID NO: 101 or 103 for SYX 8; SEQ ID NO: 110 for SYX 11; SEQ ID NO: 121 for SYX 5; SEQ ID NO: 128 or 130 for SYX 4; SEQ ID NO: 136, 138 or 139 for SYX 3; and SEQ ID NO: 148 for SYX 13.

The term "antisense polynucleotide" as used herein encompasses both nucleotides that are entirely complementary to the target sequence and those having a mismatch of one or more nucleotides, so long as the antisense polynucleotide can specifically hybridize to the target sequences. For example, the antisense polynucleotide of the present invention includes polynucleotides that have a homology of at least 70% or higher, preferably at 80% or higher, more preferably 90% or higher, even more preferably 95% or higher over a span of at least 15 continuous nucleotides of the target sequences. Any algorithms known in the art can be used to determine the above homology.

The antisense polynucleotide derivatives of the present invention act on cells producing the proteins encoded by synovial sarcoma-associated genes by binding to the DNAs or mRNAs encoding the proteins, inhibiting their transcription or translation, promoting the degradation of the mRNAs, and inhibiting the expression of the proteins, thereby resulting in the inhibition of the protein function.

An antisense polynucleotide derivative of the present invention can be made into an external preparation, such as a liniment or a poultice, by mixing with a suitable base material which is inactive against the derivative.

Also, as needed, the derivatives can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense polynucleotide derivative is given to the patient by directly applying onto the ailing site or by injecting into a blood vessel so that it will reach the site of ailment. An antisense-mounting medium can also be used to increase durability and membrane-permeability. Examples are, liposomes, poly-L-lysine, lipids, cholesterol, lipofectin or derivatives of these.

The dosage of the antisense polynucleotide derivative of the present invention can be adjusted suitably according to the patient's condition and used in desired amounts. For example, a dose range of 0.1 to 100 mg/kg, preferably 0.1 to 50 mg/kg can be administered.

The antisense polynucleotide of the invention inhibit the expression of the protein of the invention and is thereby useful for suppressing the biological activity of a protein of the invention. Also, expression-inhibitors, comprising the antisense polynucleotide of the invention, are useful, since they can inhibit the biological activity of a protein of the invention.

The antisense polynucleotide of present invention include modified oligonucleotides. For example, thioated nucleotides may be used to confer nuclease resistance to an oligonucleotide.

Therefore, future therapeutic method of the present invention will probably involves combining conventional drugs with target-specific agents aimed at different characteristics of tumor cells such as angiogenesis and invasiveness.

Further, RNA interference can be useful for treating or preventing synovial sarcoma of the present invention. RNA interference is known as a cellular event in which mRNA from an endogenous gene is degraded by introducing a double-stranded RNA (dsRNA) that has the sequence complementary to the sequence of the endogenous gene. As a result, the expression of a target gene can be inhibited or reduced. This event is reported in, for example, Elbashir, S M. et al., Nature 411, 494-498, 2001; Hannon, G J., Nature 418, 244-251, 2002 (review); Shinagawa, T. et al., Genes Dev. 17: 1340-1345 2003; International Patent Publication Nos. WO99/32619 and WO99/61613.

We successfully designed dsRNA molecules which effectively inhibit or reduce the expression of FZD10 gene via RNA interference. So, in one embodiment, the present invention provides a method for inhibiting or reducing an expression of FZD10 gene in a cell or tissue in vitro, in vivo or ex vivo, comprising introducing into the cell or tissue a double-stranded RNA molecule for FZD10 or an expression vector capable of expressing a double-stranded RNA molecule for FZD10, wherein the double-stranded RNA molecule for FZD10 comprises a nucleotide sequence targeted to the 10 to 100 continuous nucleotides, preferably 10 to 50 continuous nucleotides, more preferably 10 to 30 continuous nucleotides of SEQ ID NO:154. Preferably, the double-stranded RNA molecule for FZD10 may comprise a short nucleotide sequence as a short-interfering RNA (siRNA). For example, the double-stranded RNA molecule comprises a nucleotide sequence targeted to nucleotides nos. 1481 to 1499 (SEQ ID No. 203) or nucleotides nos. 1595 to 1613 (SEQ ID No. 204) of SEQ ID No. 154. More specifically, the double-stranded RNA molecule for FZD10 can be expressed by the expression vector having the sequence of SEQ ID Nos. 195, 196, 197, or 198 as indicated below. Also, the expression vector having the sequence of SEQ ID Nos. 195, 196, 197, or 198 may be useful in the method of the present invention.

| Sequence | Seq ID No. |
|---|---|
| 5'-CACCAACGCTGGACTGCCTGATGTTCAAGAGACATCAGGCAGTCCAGCGTT-3' | 195 |
| 5'-AAAAAACGCTGGACTGCCTGATGTCTCTTGAACATCAGGCAGTCCAGCGTT-3' | 196 |

-continued

| Sequence | Seq ID No. |
|---|---|
| 5'-CACC<u>GACTCTGCAGTCCTGGCAGT</u>TCAAGAGA<u>CTGCCAGGACTGCAGAGTC</u>-3' | 197 |
| 5'-AAAA<u>GACTCTGCAGTCCTGGCAGT</u>CTCTTGAA<u>CTGCCAGGACTGCAGAGTC</u>-3' | 198 |

The specific sequences to FZD10 are underlined.

Further, as described above, FZD10 is significantly overexpressed in synovial sarcoma (SS), and the growth of SS cells is suppressed by inhibiting or reducing the expression of FZD10. Therefore, in an alternative embodiment, the present invention provides a method for preventing or treating synovial sarcoma in a subject, comprising administering therapeutically effective amount of a double-stranded RNA for FZD10 or an expression vector capable of expressing a double-stranded RNA for FZD10 to the subject.

The method of the present invention can be performed ex vivo (e.g., by culturing the cell derived from a subject with the dsRNA or expression vector) or, alternatively, in vivo (e.g., by administering the dsRNA or expression vector to a subject).

The dsRNA can be delivered to a target location (such as a cancerous cell) by a variety of known administration methods. For example, the dsRNA can be delivered using an expression vector capable of expressing the dsRNA. Examples of an expression vector that can be used in the present invention include, but are not limited to, adenovirus, herpes virus, vaccinia virus, and RNA viruses such as retrovirus.

Other examples of the gene delivery system that can be used for administering the dsRNA to the target tissue or cell include a colloidal dispersion system, a liposome-induced system, and an artificial virus envelope. Specifically, a macromolecular complex, a nano-capsule, a microsphere, beads, oil-in-water type emulsion, micelle, mixed micelle, and liposome, for example, may be used as a delivery system.

The dsRNA or expression vector may be directly administered by intravenous injection (including continuous infusion), intramuscular injection, intraperitoneal injection, and subcutaneous injection, or via other route of administration.

Alternatively, the dsRNA or expression vector may be introduced into a cell or tissue obtained from a subject and then the cell may be administered to the subject (ex vivo method). The introduction of the dsRNA or expression vector into the cell or tissue may be carried out by a conventional gene-introducing method such as, for example, a calcium phosphate method, a DEAE dextran method, electroporation, or lipofection. The administration of the cell or tissue in which the dsRNA is expressed may also be carried out in the same manner as in the case of the direct administering of the dsRNA or expression vector.

The dosage of dsRNA or expression vector administered may vary depending on age, sex, symptoms, administration routes, administration frequency, and dosage form. However, a conventional method in the relevant art may be appropriately selected and used.

In the other embodiment, the present invention provides a composition comprising a double-stranded RNA molecule for FZD10 or an expression vector capable of expressing a double-stranded RNA molecule for FZD10, and a pharmaceutically acceptable carrier.

Various types of compositions may be formulated in a conventional manner by appropriately selecting pharmaceutically acceptable carriers that are typically used for the formulation of preparations, such as excipient, disintegrant, lubricant, surfactant, dispersing agent, buffering agent, preservative, solubilizer, antiseptic agent, stabilizing agent, and isotonizing agent.

These modulatory methods can be performed ex vivo or in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of the differentially expressed proteins or nucleic acid molecules. In one embodiment, the method involves administering an agent (e.g., an agent identified by a screening assay described herein), or combination of agents that modulates (e.g., downregulates) expression or activity of one or more differentially expressed genes. In another embodiment, the method involves administering a protein or combination of proteins or a nucleic acid molecule or combination of nucleic acid, molecules as therapy to compensate for reduced or aberrant expression or activity of the differentially expressed genes.

Diseases and disorders that are characterized by increased (relative to a subject not suffering from the disease or disorder) levels or biological activity of the genes may be treated with therapeutics that antagonize (i.e., reduce or inhibit) activity of the overexpressed gene or genes. Therapeutics that antagonize activity may be administered therapeutically or prophylactically.

Therapeutics that may be utilized include, e.g., (i) a polypeptide, or analogs, derivatives, fragments or homologs thereof of the overexpressed sequence or sequences; (ii) antibodies to the overexpressed sequence or sequences; (iii) nucleic acids encoding the overexpressed sequence or sequences; (iv) antisense nucleic acids, double-stranded RNA molecules or nucleic acids that are "dysfunctional" (i.e., due to a heterologous insertion within the coding sequences of coding sequences of one or more overexpressed sequences); or (v) modulators (i.e., inhibitors, agonists and antagonists that alter the interaction between an overexpressed polypeptide and its binding partner. The dysfunctional antisense molecules are utilized to "knockout" endogenous function of a polypeptide by homologous recombination (see, e.g., Capecchi, *Science* 244: 1288-1292 1989).

Decreased levels can be readily detected by quantifying peptide and/or RNA, by obtaining a patient biological sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Administration of a prophylactic agent can occur prior to the manifestation of symptoms characteristic of aberrant gene expression, such that a disease or disorder is prevented or, alternatively, delayed in its progression. Depending on the type of aberrant expression detected, the agent can be used for treating the subject. The appropriate agent can be determined based on screening assays described herein.

Another aspect of the invention pertains to methods of modulating expression or activity of one of the herein described differentially regulated genes for therapeutic purposes. The method includes contacting a cell with an agent that modulates one or more of the activities of the gene products of the differentially expressed genes. An agent that modulates protein activity can be an agent as described herein, such as a nucleic acid or a protein, a naturally-occurring cognate ligand of these proteins, a peptide, a peptidomimetic, or other small molecule. In one embodiment, the agent stimulates one or more protein activities of one or more of the differentially expressed genes. Examples of such stimulatory agents include active protein and a nucleic acid molecule encoding such proteins that has been introduced into the cell.

2.2. Pharmaceutical Compositions for Treating Synovial Sarcoma

In another aspect the invention includes pharmaceutical or therapeutic compositions containing one or more therapeutic compounds described herein. Such therapeutic compound includes, but not limited to, an antisense polynucleotide and a double-stranded RNA as described in Section 2.1. Pharmaceutical formulations may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the active compound with liquid carriers or finely divided solid carriers or both as needed and then, if necessary, shaping the product into the desired formulation.

Pharmaceutical formulations suitable for oral administration may conveniently be presented as discrete units, such as capsules, cachets or tablets, each containing a predetermined amount of the active ingredient; as a powder or granules; or as a solution, a suspension or as an emulsion. The active ingredient may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example, sealed ampoules and vials, and may be stored in a freeze-dried (lyophilized) condition requiring only the addition of the sterile liquid carrier, for example, saline water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the compounds of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation the compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example, a powder mix of the compound and a suitable powder base such as lactose or starch. The powder composition may be presented in unit dosage form, in, for example, capsules, cartridges, gelatin or blister packs from which the powder may be administered with the aid of an inhalator or insufflators.

When desired, the above described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the compositions may be administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg. The pharmaceutical composition preferably is administered orally or by injection (intravenous or subcutaneous), and the precise amount administered to a subject will be the responsibility of the attendant physician. However, the dose employed will depend upon a number of factors, including the age and sex of the subject, the precise disorder being treated, and its severity. Also the route of administration may vary depending upon the condition and its severity.

3. Antibody for FZD10 and its Use

The present inventors presume that synovial sarcoma (SS) may originate from neural crest cells and that the biological features of SS are similar to those of malignant peripheral nerve sheath tumor through genome-wide analysis of gene-expression patterns using a cDNA microarray consisting of 23,040 genes as described above. As a result, we have identified 26 genes that were commonly up-regulated in SS, whose products should be suitable molecular targets for the development of novel therapeutic drugs for SS. Among these up-regulated genes, we selected a candidate gene suitable for the development of molecular target therapy for SS on the basis of the following criteria: (i) expression in the vital organs including brain, heart, lung, liver, kidney and bone marrow was relatively low to avoid critically adverse side effects; and (ii) the gene product has predicted to be the plasma integral membrane protein. Based on these criteria, we focused on one of the cell-surface receptors for the Wnts, Frizzled homologue 10 (FZD10), which belongs to the Frizzled family of seven-pass transmembrane proteins. Although expression of FZD10 has been demonstrated to be up-regulated in primary colorectal cancer (Terasaki, H. et al., Int J Mol Med. 9: 107-12., 2002) and primary gastric cancer (Kirikoshi, H. et al., Int J. Oncol. 19: 767-71., 2001) as well as SS, the precise biological effects of FZD10 in tumorigenesis remain obscure. Hence, the possible role of FZD10 in tumor growth could potentially be elucidated by inhibition of signal transduction of FZD10.

The present inventors generated a specific polyclonal antibody (TT641 pAb) that recognized the N-terminal extracellular domain of FZD10 (FZD10-ECD) for the development of antibody-based therapy for synovial sarcoma (SS). As the above-mentioned criteria for selection of molecular targets, the present inventors revealed that the expression of FZD10 was absent or low in normal vital organs except epithelia in some organ tissues with immunohistochemical analysis using TT641 pAb. Moreover, it was demonstrated by the present inventors that this specific antibody was effective in mediating antibody-dependent cell-mediated cytotoxicity (ADCC) against FZD10-overexpressing SS cells. In addition, in vivo experiments using nude mice successfully showed that intratumoral injection of TT641 pAb attenuated the growth of SS xenografts presumably through induction of apoptosis of tumor cells.

Based on the above findings, the present inventors concluded that the antibody for FZD10 has therapeutic potential in the treatment and diagnosis of SS and other FZD10-overexpressing tumors. Therefore, the present invention also relates to a method for treating and/or preventing a disease which is associated with Frizzled homologue 10 (FZD10) (FZD10-associated disease) in a subject and to a method for diagnosis and/or prognosis of the disease. Compositions useful in these methods are also encompassed within the scope of the present invention.

3.1. Production of an Antibody

Antibodies that can be used in the present invention specifically react against an FZD10 protein derived from an FZD10-associated disease. The term "antibody" used herein means an antibody molecule as a whole, or its fragments such as Fab fragments, F(ab')$_2$ fragments and Fv fragments, which can bind to the protein or its partial peptides as the antigen. The antibody can be either a polyclonal antibody or a monoclonal antibody. It can also be a humanized or chimeric antibody, or a single chain Fv (scFv) antibody. The antibodies (polyclonal antibodies and monoclonal antibodies) for use in the present invention can be prepared, for example, by the following process.

3.1.1. Immunogen (Antigen)

Initially, a protein for use as an immunogen (antigen) is prepared for the preparation of an antibody useful in the present invention. FZD10 protein or its partial peptide is used as an immunogen protein. The amino acid sequence of FZD10 protein used as the immunogen in the present invention and the cDNA sequence encoding the protein are publicly available in GenBank as Accession Nos. BAA84093 (SEQ ID NO: 153) and AB027464 (SEQ ID NO: 154), respectively. The FZD10 protein or its partial peptide for use as the immunogen can be synthetically prepared according to a procedure known in the art such as a solid-phase peptide synthesis process, using the available amino acid sequence information. The partial peptides of FZD10 protein include, but are not limited to, a peptide containing residues 1-225 of the amino acid sequence shown in SEQ ID NO: 153, which corresponds to the N-terminal extracellular domain of FZD10 protein (FZD10-ECD). In addition, peptides containing residues 43-56, 61-72, 156-169, 157-170, 157-172, 161-173, 174-191, 189-202, or 214-225 of the FZD10 protein (SEQ ID NO: 153) or at least five residues, and preferably six to ten residues, of these partial sequences can be used as the immunogen. A peptide containing the residues 214-225 of the FZD10 protein (SEQ ID NO: 153) is preferably used as the immunogen in the present invention.

The protein or its partial peptide can also be prepared by using the sequence information of cDNA encoding FZD10 protein or its partial peptide according to a known gene recombination procedure. The production of the protein or its partial peptide according to such a gene recombination procedure will be illustrated below.

A recombinant vector for the production of protein can be obtained by linking the above cDNA sequence to an appropriate vector. A transformant can be obtained by introducing the recombinant vector for the production of protein into a host so that the target FZD10 protein or its partial peptide can be expressed.

As the vector, a phage or plasmid that is capable of autonomously replicating in a host is used. Examples of a plasmid DNA include pET28, pGEX4T, pUC118, pUC119, pUC18, pUC19, and other plasmid DNAs derived from *Escherichia coli*; pUB110, pTP5, and other plasmid DNAs derived from *Bacillus subtilis*; and YEp13, YEp24, YCp50 and other plasmid DNAs derived from yeast. Examples of a phage DNA include lambda phages such as λgt11 and λZAP. In addition, animal virus vectors such as retrovirus vector and vaccinia virus vector can be used, and insect virus vectors such as baculovirus vector can also be used.

The DNA encoding the FZD10 protein or its partial peptide (hereinafter referred to as FZD10 DNA) is inserted into the vector, for example, by the following method. In this method, purified DNA is cleaved by an appropriate restriction enzyme and inserted into a restriction enzyme site or a multi-cloning site of an appropriate vector DNA to ligate into the vector.

In addition to a promoter and the FZD10 DNA, any of enhancers and other cis elements, splicing signals, poly A addition signals, selective markers, ribosome binding site (RBS), and other elements can be ligated into the recombinant vector for the production of protein for use in mammalian cells, if desired.

For ligating the DNA fragment to the vector fragment, a known DNA ligase can be used. The DNA fragment and the vector fragment are annealed and ligated, thereby producing a recombinant vector for the production of a protein.

The host for use in transformation is not specifically limited as long as it allows the FZD10 protein or its partial peptide to be expressed therein. Examples of the host include bacteria, for example, *E. coli*, and *Bacillus*; yeast, for example, *Saccharomyces cerevisiae*; animal cells, for example, COS cells, Chinese Hamster Ovary (CHO) cells, and insect cells.

For example, when a bacterium is used as the host, the recombinant vector for the protein production should preferably be capable of autonomously replicating in the host bacterium and comprise a promoter, a ribosome binding site, the FZD10 DNA, and a transcription termination sequence. The recombinant vector may further comprise a gene for regulating the promoter. An example of *Escherichia coli* includes *Escherichia coli* BRL, and an example of *Bacillus* is *Bacillus subtilis*. Any promoter that can be expressed in the host such as *Escherichia coli* can be used herein.

The recombinant vector can be introduced into the host bacterium by any procedures known in the art. Such procedures include, for example, a method using calcium ions and an electroporation.

When yeast cell, an animal cell, or an insect cell is used as the host, a transformant can be produced according to a known procedure in the art, and then the FZD10 protein or its partial peptide can be produced in the host (transformant).

The FZD10 protein or its partial peptide for use as the immunogen in the present invention can be obtained from a culture of the above-generated transformant. The "culture" refers to any of culture supernatant, cultured cells, cultured microorganisms, and homogenates thereof. The transformant is cultured in a culture medium by a conventional process of culturing a host.

The culture medium for culturing the transformant obtained by using *Escherichia coli*, yeast, or other microorganisms as the host can be either a natural medium or a synthetic medium, as long as it comprises a carbon source, nitrogen source, inorganic salts, and other components utilizable by the microorganism and enables the transformant to grow efficiently.

The transformant is generally cultured by shaking culture or aeration culture with stirring under aerobic conditions at 25° C. to 37° C. for 3 to 6 hours. During culturing, pH is held at a level near neutrality by adjustment with, for example, an inorganic or organic acid, and an alkaline solution. During culturing, antibiotics such as ampicillin or tetracycline may be added to the medium according to the selective marker inserted into the recombinant expression vector, if necessary.

After culturing, when the FZD10 protein or its partial peptide is produced within the microorganism or cell, the protein or its partial peptide is extracted by homogenizing the microorganism or cell. When the FZD10 protein or its partial peptide is secreted from the microorganism or cell, the culture medium is used as is, or debris of the microorganism or cell is removed from the culture medium, for example, by centrifugation. Thereafter, the FZD10 protein or its partial peptide can be isolated from the culture and purified by a conventional biochemical method for the isolation and purification of proteins, such as ammoniumسulfate precipitation, gel chromatography, ion-exchange chromatography, and affinity chromatography, either individually or in combination.

Whether or not the FZD10 protein or its partial peptide has been obtained can be confirmed, for example, by SDS polyacrylamide gel electrophoresis.

Next, the obtained FZD10 protein or its partial peptide is dissolved in a buffer to prepare an immunogen. Where necessary, an adjuvant can be added thereto for effective immunization. Such adjuvants include, for example, commercially available Freund's complete adjuvant and Freund's incomplete adjuvant. Any of these adjuvants can be used alone or in combination.

3.1.2. Polyclonal Antibody

To prepare a polyclonal antibody, the immunogen prepared in Section 3.1.1. above is administered to a mammal such as a rabbit, rat, or mouse. An adjuvant such as Freund's complete adjuvant (FCA) or Freund's incomplete adjuvant (FIA) may be used according to necessity. The immunization is performed mainly by intravenous, subcutaneous, or intraperitoneal injection. The interval of immunization is not specifically limited and the mammal is immunized one to 7 times at the intervals of several days to several weeks. The antibody titer is determined 1 to 7 days after the last immunization, for example, by enzyme-linked immunosorbent assay (ELISA), enzyme immunoassay (ETA), or radioimmunoassay (RIA). Blood is collected on the day when the maximum antibody titer is measured, to obtain an antiserum. Thereafter, the reactivity of the polyclonal antibody in the antiserum is measured, for example, by ELISA.

3.1.3. Monoclonal Antibody

The immunogen prepared in Section 3.1.1. above is administered to a mammal such as a rabbit, rat, or mouse. An adjuvant such as Freund's complete adjuvant (FCA) or Freund's incomplete adjuvant (FIA) may be used as necessary. The immunization is performed mainly by intravenous, subcutaneous, or intraperitoneal injection. The interval of immunization is not specifically limited and the mammal is immunized one to 3 times at intervals ranging from several days to weeks. Antibody-producing cells are collected 1 to 7 days after the last immunization. Examples of the antibody-producing cells include pancreatic cells, lymph node cells, and peripheral blood cells.

To obtain a hybridoma, an antibody-producing cell and a myeloma cell are fused. As the myeloma cell to be fused with the antibody-producing cell, a generally available established cell line can be used. Preferably, the cell line used should have drug selectivity and properties such that it can not survive in a HAT selective medium (containing hypoxanthine, aminopterin, and thymidine) in unfused form and can survive only when fused with an antibody-producing cell. Possible myeloma cells include, for example, mouse myeloma cell lines such as P3X63-Ag.8.U1 (P3U1), and NS-I.

Next, the myeloma cell and the antibody-producing cell are fused. For the fusion, these cells are mixed, preferably at the ratio of the antibody-producing cell to the myeloma cell of 5:1, in a culture medium for animal cells which does not contain serum, such as DMEM and RPMI-1640 media, and fused in the presence of a cell fusion-promoting agent such as polyethylene glycol (PEG). The cell fusion may also be carried out by using a commercially available cell-fusing device using electroporation.

Then, the hybridoma is picked up from the cells after above fusion treatment. For example, a cell suspension is appropriately diluted with, for example, the RPMI-1640 medium containing fetal bovine serum and then plated onto a microtiter plate. A selective medium is added to each well, and the cells are cultured with appropriately replacing the selective medium. As a result, the cells that grow about 30 days after the start of culturing in the selective medium can be obtained as the hybridoma.

The culture supernatant of the growing hybridoma is then screened for the presence of an antibody that reacts with the FZD10 protein or its partial peptide. The screening of hybridoma can be performed according to a conventional procedure, for example, using enzyme-linked immunosorbent assay (ELISA), enzyme immunoassay (EIA) or radioimmunoassay (RIA). The fused cells are cloned by the limiting dilution to establish a hybridoma, which produces the monoclonal antibody of interest.

The monoclonal antibody can be collected from the established hybridoma, for example, by a conventional cell culture method or by producing the ascites. If necessary, the antibody can be purified in the above-described antibody collecting method according to a known procedure such as ammonium sulfate precipitation, ion-exchange chromatography, gel filtration, affinity chromatography, or a combination thereof.

The globulin type of the monoclonal antibodies useful in the present invention is not specifically limited, as long as they are capable of specifically binding to the FZD10 protein and can be any of IgG, IgM, IgA, IgE, and IgD. Among them, IgG and IgM are preferred.

The hybridoma clone Mouse-Mouse hybridoma 5F2 TK10P2 producing the monoclonal antibody raised against the recombinant FZD10 protein was deposited internationally at the IPOD International Patent Organism Depository of the National Institute of Advanced Industrial Science and Technology (AIST Tsukuba Central 6, 1-1, Higashi 1-chome, Tsukuba-shi, Ibaraki-Ken, 305-8566 Japan) as of Feb. 18, 2004 under the accession number of FERM BP-08628. The monoclonal antibody produced by the hybridoma may be preferably used in the present invention. However, the antibody that can be used in the present invention is not limited to the above monoclonal antibody.

3.1.4. Other Antibodies

In addition, techniques developed for the production of "chimeric antibodies" (Morrison et al., 1984, Proc. Natl. Acad. Sci., 81: 6851-6855; Neuberger et al., 1984, Nature, 312: 604-608; Takeda et al., 1985, Nature, 314: 452-454) can be used. These involve splicing the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region, e.g., "humanized antibodies."

Alternatively, techniques described for the production of single chain antibodies (U.S. Pat. No. 4,946,778; Bird, 1988, Science 242: 423-426; Huston et al., 1988, Proc. Natl. Acad. Sci. USA 85: 5879-5883; and Ward et al., 1989, Nature 334: 544-546) can be adapted to produce single chain antibodies against FZD10 protein or a peptide thereof. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242: 10381041).

3.1.5. Antibody Fragments

Antibody fragments that specifically recognize a portion (epitope) of a protein of interest may be generated by known techniques. For example, such fragments include, but are not limited to the F (ab')$_2$ fragments that can be produced by pepsin digestion of the antibody molecule and the Fab fragments that can be generated by reducing the disulfide bridges of the F (ab')$_2$ fragments.

Alternatively, Fab expression libraries may be constructed (Huse et al., 1989, Science, 246: 1275-1281) to allow rapid and easy identification of monoclonal Fab fragments with the desired specificity.

3.2. Therapeutic Uses of the Antibody

Described below are methods and pharmaceutical compositions for treating and/or preventing FZD10-associated disease using the antibody of the present invention. The outcome of a treatment is to at least produce in a treated subject a healthful benefit, which in the case of tumors, includes but is not limited to remission of the tumors, palliation of the symptoms of the tumors, and control of metastatic spread of the tumors.

Specifically, the method for treating and/or preventing FZD10-associated disease in a subject according to the present invention comprises administering to a subject in need thereof the antibody or the fragment described above (see, Section 3.1.).

The term "subject" herein refers to a subject who has suffered from FZD10-associated disease and also a subject suspected to have FZD10-associated disease. The subject in the present invention may be animals including mammals and avian animals. For example, mammals may include humans, mice, rats, monkeys, rabbits, and dogs.

The term "FZD10-associated disease" herein refers to a disease associated with the over-expression of FZD10 protein. Specifically, FZD10-associated diseases include, but are not limited to, synovial sarcoma (SS), colorectal cancer, gastric cancer, chronic myeloid leukemia (CML), and acute myeloid leukemia (AML).

3.2.1. Pharmaceutical Compositions

The antibody described herein can be administered to a subject at effective doses to treat or prevent the FZD10-associated disease. An effective dose refers to that amount of an antibody sufficient to result in a healthful benefit in the treated subject. Formulations and methods of administration that can be employed when the pharmaceutical composition contains an antibody of the present invention are described below.

Pharmaceutical compositions for use in accordance with the present invention can be formulated in conventional manner using one or more pharmaceutically acceptable carriers or excipients.

The antibodies can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the antibody can be in lyophilized powder form for constitution with a suitable vehicle, e.g., sterile pyrogen-free water, before use.

3.2.2. Dose and Administration Route

Toxicity and therapeutic efficacy of the antibody of the present invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD/ED.

Antibodies that exhibit large therapeutic indices are preferred. While antibodies that exhibit toxic side effects can be used, care should be taken to design a delivery system that targets such antibodies to the site of affected tissue in order to minimize potential damage to uninfected cells and, thereby, reduce side effects.

The data obtained from the cell culture assays and animal studies can be used in formulating a range of dosages for use in humans. The dosage of such antibodies lies preferably within a range of circulating plasma concentrations that include the ED50 with little or no toxicity. The dosage can vary within this range depending upon the dosage form employed and the route of administration utilized. For any antibody used in the method of the invention, the effective dose can be estimated initially from cell culture assays. A dose can be formulated in animal models to achieve a circulating plasma concentration range that includes the IC50 (i.e., the concentration of the test antibody that achieves a half-maximal inhibition of symptoms) as determined in cell culture. Such information can be used to more accurately determine useful doses in humans. Levels in plasma can be measured, for example, by high performance liquid chromatography.

While depending on the conditions and age of the subject and/or administration route, one skilled in the art can select an appropriate dose of the pharmaceutical composition of the present invention. For example, the pharmaceutical composition of the present invention is administered in an amount such that the antibody according to the present invention is administered to the subject in a day in an amount of about 3 to about 15 µg per kg body weight of subject, and preferably of about 10 to about 15 µg per kg body weight of subject. The administration interval and times can be selected in consideration of the condition and age of the subject, administration route, and response to the pharmaceutical composition. For example, the pharmaceutical composition can be administered to the subject one to 5 times, preferably 1 times a day for 5 to 10 days.

The pharmaceutical composition can be administered systemically or locally. It is preferably administered in a targeting delivery manner so as to deliver the active component to an affected site.

3.2.3. Combination Therapy

In particular embodiments, the methods and compositions of the present invention are used for the treatment or prevention of FZD10-associated disease together with one or a combination of chemotherapeutic agents including, but not limited to, methotrexate, taxol, mercaptopurine, thioguanine, cisplatin, carboplatin, mitomycin, bleomycin, doxorubicin, idarubicin, daunorubicin, dactinomycin, vinblastine, vincristine, vinorelbine, paclitaxel, and docetaxel.

With respect to radiation therapy, any radiation therapy protocol can be used depending upon the type of FZD10-associated disease to be treated. For example, but not by way of limitation, X-ray radiation can be administered. Gamma ray emitting radioisotopes, such as radioactive isotopes of radium, cobalt, and other elements may also be administered to expose tissues.

In another embodiment, chemotherapy or radiation therapy is administered, preferably at least an hour, five hours, 12 hours, a day, a week, a month, and more preferably several months (e.g., up to three months) subsequent to using the methods and compositions containing the antibody of the present invention. The chemotherapy or radiation therapy administered prior to, concurrently with, or subsequent to the treatment using the methods and compositions according to the present invention can be administered by any method known in the art.

3.3. Diagnostic and Prognostic Uses of the Antibody

Antibodies directed against FZD10 protein or peptide fragments thereof in Section 3.1. may also be used as diagnostics and prognostics, as described herein. Such diagnostics methods may used to detect the presence or absence of FZD10-associated disease and the risk of having the disease. The method for diagnosis and/or prognosis of an FZD10-associated disease of the present invention comprises immunologically detecting or determining the FZD10 protein derived from the disease in a sample using an antibody or a fragment thereof according to the present invention. Specifically, a method for diagnosis or prognosis of FZD10-associated disease or of a predisposition to develop the disease in a subject according to the present invention comprises:

(a) contacting a sample from the subject with an antibody against FZD10 protein or a fragment thereof;

(b) detecting the FZD10 protein in the sample; and (c) judging whether or not the subject suffers from or is at risk of developing the disease based on the relative abundance of the FZD10 protein compared to a control.

The method for diagnosis and/or prognosis of the present invention can be performed based on any procedures, as long as it is an assay using an antibody, i.e., an immunological assay. Thereby one can detect the FZD10 protein using the antibody or a fragment thereof of the present invention as the antibody used in the assay. For example, the FZD10 protein can be detected by using an immunohistochemical staining, immunoassay such as enzyme immunoassays (ELISA and EIA), immunofluorescent assay, radioimmunoassay (RIA), or Western blotting.

A sample to be tested in the method for diagnosis and/or prognosis of FZD10-associated disease of the present invention is not specifically limited, as long as it is a biological sample that may contain the FZD10 protein derived from the FZD10-associated disease. Examples of the sample include extract of a cell or organ, and tissue sections, as well as blood, sera, plasma, lymphocyte cultivated supernatant, urine, spinal fluid, saliva, sweat, and ascites. The abundance of the FZD10 protein as determined in samples such as tumor tissue, tumor biopsy, and metastasis tissue by using the antibody or a fragment thereof of the present invention is specifically useful as an index of an FZD10-associated disease.

For example, antibodies and fragments thereof according to the present invention, such as those described above in Section 3.1., may be used to quantitatively or qualitatively detect the FZD10 protein. The antibodies (or fragment thereof) of the present invention may, additionally, be employed histologically, as in immunofluorescence or immunoelectron microscopy, for in situ detection of FZD10 protein. In situ detection may be accomplished by removing a histological sample from a subject, such as paraffin-embedded sections of tissues (such as surgical specimens) and applying thereto a labeled antibody of the present invention. The antibody (or fragment thereof) is preferably applied by overlaying a sample with the labeled antibody (or fragment thereof). Using the present invention, those skilled in the art will readily perceive that any of a wide variety of histological methods (such as staining procedures) can be modified in order to achieve such in situ detection.

Immunoassays for FZD10 protein will typically comprise incubating a sample from a subject to be examined, such as a biological fluid, a tissue extract, freshly harvested cells, or lysates of cells that have been incubated in cell culture, in the presence of a detectably labeled antibody of the present invention, and detecting the bound antibody by any of a number of techniques well-known in the art.

The sample may be brought into contact with and immobilized onto a solid phase support or carrier such as nitrocellulose, or another solid support which is capable of immobilizing cells, cell particles, or soluble proteins. The support may then be washed with suitable buffers followed by treatment with the detectably labeled antibody against FZD10. The solid phase support may then be washed with the buffer a second time to remove unbound antibody. The amount of bound label on the solid support may then be detected by conventional means.

The term "solid phase support or carrier" means any support capable of binding an antigen or an antibody. Those skilled in the art will know many suitable carriers for binding antibodies or antigens, or will be able to ascertain the same by use of routine experimentation.

The binding activity of a given lot of anti-FZD10 antibody may be determined according to well-known methods. Those skilled in the art will be able to determine operative and optimal assay conditions for each determination by employing routine experimentation.

To detect a reaction between the antibody (or its fragment) of the present invention and the FZD10 protein derived from an FZD10-associated disease affected site in a sample easily, the reaction can be directly detected by labeling the antibody of the present invention or indirectly detected by using a labeled secondary antibody. The latter indirect detection procedure, such as a sandwich assay or competitive assay of ELISA, is preferably used in the method of the present invention for better sensitivity.

Examples of labels for use herein are as follows. Peroxidases (PODs), alkaline phosphatases, β-galactosidase, urease, catalase, glucose oxidase, lactate dehydrogenase, amylases, and biotin-avidin complexes can be used in an enzyme immunoassay. Fluorescein isothiocyanate (FITC), tetramethylrhodamine isothiocyanate (TRITC), substituted rhodamine isothiocyanate, and dichlorotriazine isothiocyanate can be used in an immunofluorescent assay. Tritium, $^{125}$I, and $^{131}$I can be used in a radioimmunoassay. NADH-FMNH$_2$-luciferase assay, luminol-hydrogen peroxide-POD system, acridinium esters, and dioxetane compounds can be used in an immunoluminescent assay.

The label can be attached to the antibody according to a conventional procedure. For example, the label can be attached to the antibody by a glutaraldehyde method, maleimide method, pyridyl disulfide method, or periodate method in the enzyme immunoassay, and by a chloramine T method or Bolton-Hunter method in the radioimmunoassay.

The assay can be performed according to a known procedure (Ausubel, F. M. et al. Eds., Short Protocols in Molecular Biology, Chapter 11 "Immunology" John Wiley & Sons, Inc. 1995).

For example, when the antibody of the present invention is directly labeled with the label described above, the sample is brought into contact with the labeled antibody to thereby form a complex between the FZD10 protein and the antibody. Then, unbound labeled antibody is separated, and the level of the FZD10 protein in the sample can be determined based on the amount of the bound labeled antibody or that of the unbound labeled antibody.

When a labeled secondary antibody is used, the antibody of the present invention is allowed to react with the sample in a primary reaction, and the resulting complex is allowed to react with the labeled secondary antibody in a secondary reaction. The primary reaction and the secondary reaction can be performed in reverse order, concurrently with some interval of time therebetween. The primary and secondary reactions yield a complex of [FZD10 protein]-[the antibody of the invention]-[the labeled secondary antibody] or a complex of [the antibody of the invention]-[FZD10 protein]-[the labeled secondary antibody]. Unbound labeled secondary antibody is then separated, and the level of the FZD10 protein in the sample can be determined based on the abundance of the bound labeled secondary antibody or that of the unbound labeled secondary antibody.

One of preferred embodiments of the present invention will be illustrated below. Initially, the antibody of the present invention as a primary antibody is brought into contact with a sample such as a tissue section. Unspecific binding of the primary antibody is then blocked using a known blocking reagent. Next, the sample is brought into contact with a labeled secondary antibody that reacts with the primary antibody (the antibody of the present invention) at a site different from that of a FZD10 protein. Signals from the label are then detected.

The "secondary antibody that reacts with the primary antibody at a site different from that of a FZD10 protein" for use herein is not specifically limited, as long as it is an antibody that recognizes a site other than the binding site between the primary antibody and the FZD10 protein. The secondary antibody just mentioned above can be any of polyclonal antibodies, antisera, and monoclonal antibodies, as well as fragments of these antibodies such as Fab fragment, F(ab')$_2$ fragment, and Fab' fragment. The secondary antibody can be a mixture of two or more types of antibodies.

Thus, the FZD10 protein abundance in the sample from a subject is determined, and whether or not the subject suffers from or is at the risk of developing the FZD10-associated disease can be judged based on the relative abundance of the FZD10 protein, where necessary as compared with a control, including the protein abundance in a normal sample or a sample of a tissue in which the FZD10 protein is not expressed. As apparent to those skilled in the art, the FZD10 protein abundance varies depending on the conditions, sex, age, and other factors in each subject. Accordingly, the presence of the disease or the risk thereof can be determined preferably by comparing the FZD10 protein abundance in the sample with that in a normal sample or a sample of a tissue in which the FZD10 protein is not expressed, and determining the difference between the two samples. To perform a prognosis, it is also effective to compare the FZD10 protein abundance in the sample with that in a sample collected when the subject has suffered from a primary tumor.

According to another embodiment, the antibody of the present invention is labeled with a radioisotope, and the labeled antibody is parenterally administered to a subject. Thus, the localization of a primary tumor and the related metastasized tumor of FZD10-associated disease can be rapidly found in a non-invasive manner. Such a diagnosis method is known as tumor imaging, and one skilled in the art can easily understand the procedures thereof. The labeled antibody can be administered to the subject systemically or locally, preferably through a parenteral route such as intravenous injection, intramuscular injection, intraperitoneal injection, or subcutaneous injection.

3.3.1. Kits Comprising the Antibody

The antibodies according to the present invention specifically react with a FZD10 protein as mentioned above and can thereby be used in kits for diagnosis and/or prognosis of an FZD10-associated disease.

The kit for diagnosis and/or prognosis of the present invention comprises an antibody of the present invention described in Section 3.1. By detecting the FZD10 protein in a sample from a subject who is suspected to suffer from a FZD10-associated disease with the use of the kit for diagnosis and/or prognosis of the present invention, whether or not the subject suffers from the FZD10-associated disease can be rapidly and easily ascertained. Kits for diagnosis and/or prognosis of diseases using such immunological reactions have been widely known, and one skilled in the art can easily select appropriate components other than the antibody. The kits for diagnosis and/or prognosis of the present invention can be used in any means, as long as it is a means for immunoassay.

EXAMPLES

The present invention will be further illustrated by the following non-limiting examples:

Example 1

General Methods (1) Tissue Samples

Primary or recurrent STS tissues were obtained from 47 patients who underwent surgical resection, including 13 with SS and 34 with spindle cell sarcomas (14 MFHs, 10 LMSs, 3 PLSs, 3 DLSs and 4 MPNSTs). Among the four MPNSTs, three had developed in patients with clinical diagnosis of type 1 neurofibromatosis (MPNST248, MPNST397, and MPNST558). Tumor samples were snap-frozen in liquid nitrogen immediately after resection and stored at −80° C. until preparation of RNA. Tissue specimens were obtained in the same manner from 15 additional SS patients to verify the expression patterns. Part of each tumor sample was fixed in 10% formalin and routinely processed for hematoxylin and eosin staining to establish a pathological diagnosis by the present inventors. Histological subclassification of SS, either monophasic or biphasic, was determined by the standard criteria, mainly based on the presence of an epithelial component (Weiss, S. W. and Goldblum, J. R. Enzinger and Weiss's Soft Tissue Tumors, 4th edition. St. Louis: Mosby, 2001). Nine of the 13 cases were thus classified as monophasic and the remaining four were as biphasic. At least 90% of the viable cells in each specimen were identified as tumor cells; contamination with normal elements such as inflammatory cells was considered to be minimal (2) RNA Preparation and T7-Based RNA Amplification Total RNAs were extracted from each frozen specimen and from human mesenchymal stem cells (MSC) purchased from BioWhittaker, Inc. (Walkersville, Md.) as a universal control, using TRIzol reagent (GIBCO BRL, Rockville, Md.) according to the manufacturer's instructions. After treatment with DNase I (Nippon Gene, Osaka, Japan), 10 µg of total RNAs from the tumors and MSC were amplified using an Ampliscribe T7 Transcription Kit (Epicentre Technologies, Madison, Wis.) and 5 µg of amplified RNAs were labeled with Cy5-dCTP and Cy3-dCTP, respectively, as described previously (Ono, K. et al., Cancer Res., 60: 5007-11, 2000). Total RNA was also prepared from three SS cell lines (OUSS, HS-SY-II and YaFuSS) to reinforce the microarray data. All samples used in this study were analyzed for detection of SYT-SSX fusion transcripts by reverse transcription-PCR (RT-PCR) experiments, using the following primers: for the SYT-SSX1 gene, 5'-CAACAGCAAGATGCATACCA-3' (SEQ ID NO: 177) and 5'-GGTGCAGTTGTTTCCCATCG-3' (SEQ ID NO: 178); for the SYT-SSX2 gene, 5'-CAACAG-CAAGATGCATACCA-3' (SEQ ID NO: 179) and 5'-GGCA-CAGCTCTTTC CCATCA-3' (SEQ ID NO: 180).

(3) cDNA Microarray.

A "genome-wide" cDNA microarray was fabricated with 23,040 cDNAs selected from the UniGene database (build #131) of the National Center for Biotechnology Information. Establishment of the microarray, procedures of hybridization and washing, and photometrical quantification of signal intensities of each spot were done as described previously (Ono, K. et al., supra), except that all hybridization and washing procedures were carried out with an Automated Slide Processor (Amersham Bioscience, Buckinghamshire, UK). Each slide contained 52 housekeeping genes, and the Cy5/Cy3 ratio for each gene's expression was adjusted so that the averaged Cy5/Cy3 ratio of the panel of housekeeping genes was 1.0. A cut-off value was assigned to each microarray slide, using variance analysis. If both Cy3 and Cy5 signal intensities were lower than the cut-off values, the expression level of the corresponding gene in that sample was assessed as low or absent. For other genes, Cy5/Cy3 was calculated as a relative expression ratio.

(4) Cluster Analysis of 47 STS Cases According to Gene-Expression Profiles

A hierarchical clustering method was applied to both genes and samples. To obtain reproducible clusters for classification of the 47 STSs, 1,204 genes were selected for which data were present in 90% of the experiments, and with expression ratios that varied by standard deviations of more than 1.0. The analysis was performed using web-available software ("Cluster" and "TreeView") written by M. Eisen (http://genome-www5.stanford.edu/MicroArray/SMD/restech.html). Before the clustering algorithm was applied, the fluorescence ratio for each spot was first log-transformed ($\log_2$) and then the data for each sample were median-centered to remove experimental biases.

(5) Identification of Up-Regulated Genes Common to SS

The relative expression ratio of each gene (Cy5/Cy3 intensity ratio) was classified into one of four categories: (A) up-regulated (expression ratio more than 2.0); (B) down-regulated (expression ratio less than 0.5); (C) unchanged (expression ratio between 0.5 and 2.0); and (D) not expressed (or slight expression but under the cut-off level for detection). We used these categories to detect a set of genes whose changes in expression ratios were common among samples as well as specific to a certain subgroup in accordance with Shena et al. (Schena, M. et al., Proc. Natl. Acad. Sci. USA, 93: 10614-10619, 1996). To detect candidate genes that were commonly up-regulated in SS, the overall expression patterns of 23,040 genes were first screened to select genes with expression ratios of more than 3.0 that were present in more than 75% of the SS cases categorized as (A), (B), or (C). Then from a list of selected genes, those showing slight or no expression (category D) were chosen in more than 80% of non-SS cases.

(6) Cluster Analysis of 13 SS Cases According to Gene-Expression Profiles

To clarify the nature of the histological heterogeneity within the SS group, focus was placed on differences in expression patterns of 23,040 genes among the 13 original SS cases. From the overall expression profiles of the SS group, 1,405 genes were chosen for which data were present in 75% of the cases, and with expression ratios that varied by standard deviations of more than 1.0. Clustering analysis was performed in the manner described above.

(7) Identification of Candidate Genes for Discriminating Between SS Subclasses 7,067 genes for which data were present in more than 10 of 13 SS cases were selected, and the mean ($\mu$) and standard deviation ($\sigma$) was calculated from the relative expression ratios of each gene in one of the two subclasses. A discrimination score (DS) for each gene was defined as $DS=\mu_1-\mu_2/(\sigma_1+\sigma_2)$, where the subscripts refer to the same group (Golub, T. R. et al., Science, 286: 531-7, 1999). A large DS indicates that a gene's expression varies greatly between the two groups but little within its own group. A permutation test was invoked to calculate the ability of individual genes to distinguish between the two subclasses; samples were randomly permutated into each of the two groups 10,000 times. Since the DS dataset of each gene showed a normal distribution, a P value for the user-defined grouping was calculated. If the P value was less than 0.001, the gene was considered to have the power to distinguish the two groups.

(8) Semi-Quantitative and Real-Time Quantitative RT-PCR

A 3-μg aliquot of total RNA from each tissue sample was reverse-transcribed for single-stranded cDNAs using oligo $(dT)_{12-18}$ primer and Superscript II (Invitrogen, Carlsbad, Calif.). Semi-quantitative RT-PCR was carried out with the same gene-specific primers as those prepared for constructing our cDNA microarray or with a β2 microglobulin (β2MG)-specific primer as an internal control as described previously (Yamanaka, Y. et al., Biochem. Biophys. Res. Commun, 287: 198-203, 2001). The primer sequences are listed in Table 1. PCR reactions were optimized for the number of cycles to ensure product intensity within the linear phase of amplification. Real-time quantitative RT-PCR (TaqMan PCR, Applied Biosystems, Foster City, Calif.) was performed with the ABI Prism 7700 Sequence Detection system (Applied Biosystems) as described previously (Yamanaka, supra). The primers and TaqMan probes are shown in Table 2. The expression levels of each candidate gene were corrected by that of β2MG and relative expression ratios (r) of each sample to MSC were calculated.

TABLE 1

Gene-Specific Primers

| ID | Hs. | GENE | PCR | | Forward and Reverse Primers | SEQ ID NO: |
|---|---|---|---|---|---|---|
| C0671 | 31664 | frizzled homolog 10 | 260 | F | 5'-TCAGAAACCCTTCAGTGCTACAT-3' | 1 |
| | | | | R | 5'-ATACACACGCAGAAACCACTCTT-3' | 2 |
| A8647 | 105805 | EST | 255 | F | 5'-CCACTGTCTCATGAAGTGTCAAA-3' | 3 |
| | | | | R | 5'-ACAGAATGGTAAGAAAGGAAGCC-3' | 4 |
| A0102 | 1408 | endothelin 3 | 1004 | F | 5'-GACACAGATCATAGCTCTACAGGA-3' | 5 |
| | | | | R | 5'-GAGTATTTGAGCAATTGATGGG-3' | 6 |
| A5094N | 53563 | collagen, type IX, alpha 3 | 234 | F | 5'-GTGAGGAAGCAAGTGACAAGG-3' | 7 |
| | | | | R | 5'-CACCCTACCTTCTCTCAAATGC-3' | 8 |
| A0623 | 144879 | dual specificity phosphatase 9 | 308 | F | 5'-GAGAGCGCAATACCTCACG-3' | 9 |
| | | | | R | 5'-GTGGAGAAACAGGGAGGTGA-3' | 10 |
| B9059 | 25960 | N-myc | 808 | F | 5'-AAGACAGCAGCAGTTGCTAAAGA-3' | 11 |
| | | | | R | 5'-GAAGAAACAGGCTAGGAAAAAGG-3' | 12 |
| A6384 | 346950 | cellular retinoic acid-binding protein 1 | 511 | F | 5'-GGGGATCAGTTCTACATCAAGAC-3' | 13 |
| | | | | R | 5'-CGTCTAACCAGTTTAATGACTTCG-3' | 14 |
| A0277 | 26988 | ephrin-B3 | 1001 | F | 5'-CATGAGAAGAAGTGTCCCGTTT-3' | 15 |
| | | | | R | 5'-TAAAACTACTGAGGTGACGGCAT-3' | 16 |
| A5044 | 31439 | serine protease inhibitor, Kunitz type, 2 | 239 | F | 5'-CCAACATCACTTCTGTGATGAGA-3' | 17 |
| | | | | R | 5'-GATTTGAGTGATCATTAGGGCTG-3' | 18 |
| C0488 | 30743 | preferentially expressed antigen in melanoma | 513 | F | 5'-CAACCTTAAGCTTCTACGGGATT-3' | 19 |
| | | | | R | 5'-CCTCAAGTCAACATCTGCCTATC-3' | 20 |
| A2246 | 73964 | EphA4 | 1014 | F | 5'-GAAGGCGTGGTCACTAAATGTAA-3' | 21 |
| | | | | R | 5'-CTTTAATTTCAGAGGGCGAAGAC-3' | 22 |
| A0650 | 49585 | fibroblast growth factor 18 | 912 | F | 5'-ACTTGCCTGTGTTTACACTTCCT-3' | 23 |
| | | | | R | 5'-GTGTTGGTTTCCTCATTCAAGTC-3' | 24 |
| C1372 | 256311 | granin-like neuro-endocrine peptide precursor | 365 | F | 5'-CTGTTGAGGTACTTGCTGGGAC-3' | 25 |
| | | | | R | 5'-TCAGATCATGTTTATTGTGGGG-3' | 26 |
| E1451 | 198760 | neurofilament, heavy polypeptide (200 kD) | 516 | F | 5'-CCAAAGAAACTCAGAAGAGTCC-3' | 27 |
| | | | | R | 5'-GAAAGTGAACTCCAGTGGAAAG-3' | 28 |
| A2691N | 2877 | cadherin 3, type 1, P-cadherin (placental) | 806 | F | 5'-CTGAAGGCGGCTAACACAGAC-3' | 29 |
| | | | | R | 5'-TACACGATTGTCCTCACCCTTC-3' | 30 |
| B9201 | 284122 | WNT inhibitory factor 1 | 860 | F | 5'-CACTGCAATAAAAGGTACGAAGC-3' | 31 |
| | | | | R | 5'-TTCAGAAAACTAAAGCAGCACC-3' | 32 |
| A2029 | 79404 | neuron-specific protein | 1001 | F | 5'-CTCTGGCATCTTGGTAAGGAG-3' | 33 |
| | | | | R | 5'-CCTCATGTTCTTTATTTGCACAGAG-3' | 34 |
| C9473 | 92732 | *Homo sapiens* X28 region near ALD locus | 286 | F | 5'-GTGAACTGAGGAAGGTGCTTAGA-3' | 35 |
| | | | | R | 5'-CTTTATTCTTGAGATGCAGGGG-3' | 36 |

TABLE 1-continued

Gene-Specific Primers

| ID | Hs. | GENE | PCR | | Forward and Reverse Primers | SEQ ID NO: |
|---|---|---|---|---|---|---|
| A8857 | 11849 | Hypothetical protein MGC15827 | 503 | F<br>R | 5'-CCCAGATGACCACATTTAATACC-3'<br>5'-AGAGAAGGGAATCACAACACAGA-3' | 37<br>38 |
| C5852 | 55407 | *Homo sapiens* cDNA DKFZp434K0621 | 814 | F<br>R | 5'-CAAGGCTAGAAAGATGCTACGTT-3'<br>5'-CAGACACGCACTTGTGGTTTATT-3' | 39<br>40 |
| A5313 | | BC009491clone MGC 16382 | 527 | F<br>R | 5'-AGAAGATGCCAATGTTTCATCC-3'<br>5'-GACTGTGTTGAGTAAGAGCCACA-3' | 41<br>42 |
| D6309 | 129010 | EST | 351 | F<br>R | 5'-ATGCTGTCTCCAGACCCACT-3'<br>5'-AGTGACCCTGGCTCTGAAAG-3' | 43<br>44 |
| D6252 | 128899 | EST | 227 | F<br>R | 5'-GGCTTATTCTTCAGGCACTAAGG-3'<br>5'-AGCAGTTGGAAATGTACTTGCAC-3' | 45<br>46 |
| C9468 | 92679 | *Homo sapiens* clone CDABP0014 | 206 | F<br>R | 5'-CTCCTTTCCAGACAGATGAGAGA-3'<br>5'-ATGCCTGTTTTTCCTACACTCAG-3' | 47<br>48 |
| B8437 | 24583 | hypothetical protein DKFZp434C0328 | 268 | F<br>R | 5'-TTACTGTTTTGTCTCTTGAGCCC-3'<br>5'-GTTACCCCTAGGTATGCTTCGTT-3' | 49<br>50 |
| B7503 | 12714 | EST | 518 | F<br>R | 5'-AAAAGGATAGTTCCAGGCCATAG-3'<br>5'-GCCAGTAGACCCAAACAATAAGA-3' | 51<br>52 |

Italic ID; Highly specific to SS. Hs.; UniGene accession number.
PCR; PCR product size (bp). Primer F or R; forward or reverse primer sequence, respectively.

TABLE 2

A list of primer sets and TaqMan probes

| ID | | SEQ ID NO: |
|---|---|---|
| Forward Primer | | |
| A2673 | 5'-CGATGAGCTGGGAGTGAAGC-3' | 53 |
| B2602 | 5'-TTTCGTTCTGTTTTCTCATGACAGA-3' | 54 |
| A2041 | 5'-GGATTGCAGCTTCTGGGAAC-3' | 55 |
| D5183 | 5'-TTCGAGAAGCGCCACAAGA-3' | 56 |
| C9540 | 5'-AGCCCTCGCGGCAAG-3' | 57 |
| B9386 | 5'-TTGAAATGCTTTGATATTCTAATTGACA-3' | 58 |
| A4266 | 5'-TGACGGACTTCGTGTGCAAA-3' | 59 |
| A5183 | 5'-ACGCAGACAGAAGGTGGAGC-3' | 60 |
| A1181 | 5'-GACAAATGTTCGTCCTGTTAATTTATAGG-3' | 61 |
| A1848 | 5'-GAGGAGATCCGGCGCATAA-3' | 62 |
| A8306 | 5'-CTCTTTGCACATGGGCATCA-3' | 63 |
| A1887N | 5'-CTGGCCTGCCTTCGTTAACT-3' | 64 |
| Reverse Primer | | |
| A2673 | 5'-CATCGCTCTTGGATTCCCAC-3' | 65 |
| B2602 | 5'-GAGAGAGTCAGACTAATAAACAGGCTGTT-3' | 66 |
| A2041 | 5'-CAAGCAGTTTGGAGGCAGC-3' | 67 |
| D5183 | 5'-GCTGAGAGGCCGGCACT-3' | 68 |
| C9540 | 5'-GCTGGCTCAACATGGAAGGA-3' | 69 |

TABLE 2-continued

A list of primer sets and TaqMan probes

| ID | | SEQ ID NO: |
|---|---|---|
| B9386 | 5'-ATTCTTACGAACTTTAAAAAAATAGCAAAGT-3' | 70 |
| A4266 | 5'-ATTCACGCCGAAGAAGTTGG-3' | 71 |
| A5183 | 5'-GAGACATGCAGCCGTTTCG-3' | 72 |
| A1181 | 5'-TTTTGCCACTGTGTATATCATCCA-3' | 73 |
| A1848 | 5'-AGCACTCGCTGGAACATGAA-3' | 74 |
| A8306 | 5'-TCTTTGTAAGGCTGTACCTTGCAT-3' | 75 |
| A1887N | 5'-GGGCAGGATACCCAAACAAA-3' | 76 |

TaqMan Probe

| ID | | SEQ ID NO: |
|---|---|---|
| A2673 | 5'-Fam-CAGGCAAAAGTGAGCGCAGCTCCT-TAMRA-3' | 77 |
| B2602 | 5'-Fam-CCCTTTCCCCACCCCTAAGTGCCTAA-TAMRA-3' | 78 |
| A2041 | 5'-Fam-ATCTATGAGCTTCGAAATAAGGAACGCATCTCTG-TAMRA-3' | 79 |
| D5183 | 5'-Fam-CACCTGTCCCCCTGCTTCAGGGA-TAMRA-3' | 80 |
| C9540 | 5'-Fam-CCCTCACTCTCTCGCCTGTTCTGTGTC-TAMRA-3' | 81 |
| B9386 | 5'-Fam-AACAAGTTTTTTCCCTGCTCCCCAAATAGAAT-TAMRA-3' | 82 |
| A4266 | 5'-Fam-CAGCAGA GTGAGCTGTTGACTCGATCG-TAMRA-3' | 83 |
| A5183 | 5'-Fam-AGACGGCCAGCAGTCACAGACACAAAGT-TAMRA-3' | 84 |
| A1181 | 5'-Fam-TGTGGAGGTAGTTGGGTAGAAAAATTATTAGAACATTCAC-TAMRA-3' | 85 |
| A1848 | 5'-Fam-TACCAGCAGCAATATGGACGGAGCCTT-TAMRA-3' | 86 |
| A8306 | 5'-Fam-TCTGTAGAATTTGACGGAACACAGCTATTTCCC-TAMRA-3' | 87 |
| A1887 N | 5'-Fam-TGTCAATAAACAGCTTCATGCCTTTGTAAGTTATTTCTTG-TAMRA-3' | 88 |

Primer F or R; forward or reverse primer sequence, respectively.

(9) Development of Predictive Formula for Discrimination of SS Subclasses

From the quantitative results obtained by real-time RT-PCR, the discriminant coefficient ($k_j$) of a predictor gene (j) and constant value (C) were determined by forward stepwise discriminant analysis. A predictive score ($PS_i$) of each sample (i) was calculated as a following formula:

$$PS_i = \Sigma_j k_j \times \log_2(r_{ij}) + C$$

where $r_{ij}$ is the expression ratio (sample i/MSC) of gene j. Statistical analyses were to performed with statistical package SPSS (Chicago).

(10) Cell Line

Human synovial sarcomas cell lines, HS-SY-2, and YaFuSS were obtained from Department of Tissue Regeneration, Institute for Frontier Medical Sciences Kyoto University. All cells were grown in monolayers in appropriate media (Sigma), Dulbecco's modified Eagle's medium for HS-SY-2 and YaFuSS, media was supplemented with 10% fetal bovine serum and 1% antibiotic/antimycotic solution (Sigma).

(11) Effect of Anti-Sense Oligonucleotides on mRNA Expression

Antisense (AS) or reverse (RE) oligonucleotides (1 μM) were transfected into HS-SY-2 or YaFuSS cells with Lipofectin reagent (Invitrogen) for 4 h. After transfection of HS-SY-2 or YaFuSS cells with oligonucleotides for 12 h, both cells were harvested and analyzed of each gene expression by semi quantitative RT-PCR Analysis.

(12) Semiquantitative RT-PCR Analysis

Isolation of total RNA from cultured cells was performed using RNeasy spin column kits (Qiagen) according to the manufacturer's instructions. cDNAs were synthesized from 1 μg aliquots of total RNAs with the SuperScript Preamplification System (Life Technologies, Inc.). The RT-PCR exponential phase was determined to allow semiquantitative comparisons among cDNAs developed from identical reactions.

Each PCR regime involved a 94° C., 2-min initial denaturation step followed by 18 cycles (for C0488), 19 cycles (for A5094N,C1372), 23 cycles (for A2246), 24 cycles (for A0277), 25 cycles (for A0623), 30 cycles (for A0102), or 18 cycles (for β2MG), cycles of 94° C. for 30 s, 58° C. for 30 s, and 72° C. for 1 min, on a Gene Amp PCR system 9600 (Perkin-Elmer). β2MG served as the quantity control.

Example 2

Cluster Analysis of Gene Expression Profiles

Figure 1A:
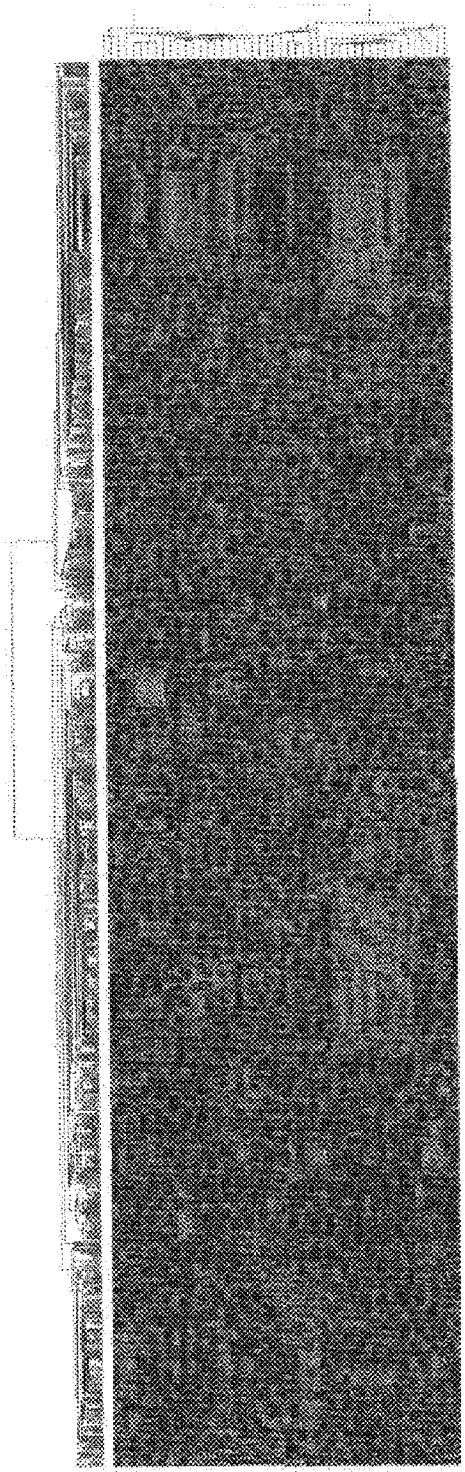
FIG. 1A is a dendrogram showing the biological classification of 47 STS cases. Horizontal rows represent individual genes; vertical columns represent individual samples. Each cell in the matrix represents the expression level of a single transcript in a single sample, with red and green indicating transcript levels respectively above and below the median for that gene across all samples. Black represents unchanged expression; gray indicates no or slight expression (intensities of both Cy3 and Cy5 under the cut-off value.) Color saturation is proportional to magnitude of the difference from the mean. The dendrogram at the top of the matrix indicates the degree of similarity between tumor samples. The dendrogram on the left side indicates the degree of similarity among the selected genes according to their expression patterns.
Figure 1B:
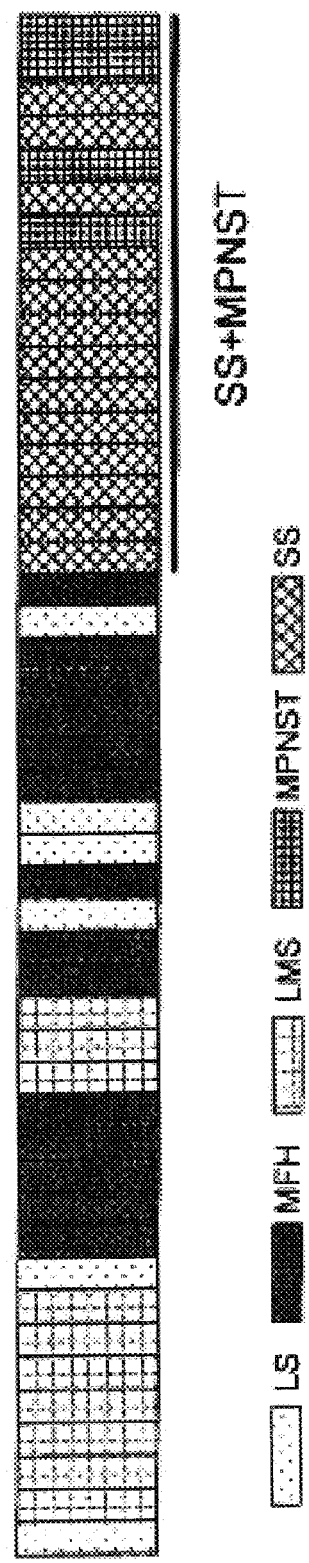
FIG. 1B is an enlarged view of a dendrogram, showing the biological classification of 47 STS cases; the shorter the branches, the greater the similarity.

All 47 tumors were first examined for the presence of SYT-SSX fusion transcripts, by means of RT-PCR. In all of the 13 tumors that had been diagnosed as SS, fusion transcripts of either SYT-SSX1 (11 cases) or SYT-SSX2 (2 cases)

were identified, but no evidence of SYT-SSX fusion transcripts in any of the 34 tumors diagnosed as other histological types were found. The expression profiles of all 47 STS cases were then subjected to a hierarchical clustering analysis. Reproducible clusters were obtained with 1,204 genes (see Example 1); their expression patterns across the 47 STS cases are shown in FIGS. 1A and 1B. MFH, LMS, DLS, and PLS were scattered into several different clusters, and failed to compose a disease-specific cluster. On the contrary, SS cases showed a distinct cluster along with MPNST. Four tumors with biphasic features (SS190, SS334, SS487 and SS582) were clustered into one group, but nine tumors with monophasic features failed to make one cluster. Two SS cases (SS213 and SS438) constituted one subcluster together with a case of MPNST (MPNST248), and one case of MPNST (MPNST558) fell into the major cluster of SS. These data suggested that SS and MPNST are closely related diseases in terms of gene expression, although both are regarded as clearly distinct entities from the histological point of view.

Example 3

Identification of Gene with Clinically Relevant Expression Patterns in Synovial Sarcoma Cells (1) Identification of Up-Regulated Genes Common to SS Cases Twenty-six genes, including four ESTs were identified, that were commonly up-regulated in SS (Table A). Among them frizzled homolog 10 (C0671) and one EST (A8647) were up-regulated specifically in SS. The remaining 24 genes were also expressed in MPNST, at the same or lower levels. The results of semi-quantitative RT-PCR experiments confirmed the specific expression of these genes in SS, or SS and MPNST (FIG. 2). In addition, expression of all 26 genes was detected in three SS cell lines, indicating that this activity was intrinsic to SS cells and not induced by in vivo environments. In most of the known genes that were up-regulated commonly in SS and MPNST, the proposed function and distribution of expression were related to neural tissues, e.g. EphA4, ephrin-B3, and endothelin 3 (EDN3). Moreover, SS expressed additional markers of neural differentiation such as neurofilament, neuron-specific protein, and FGF18, which were expressed in MPNST at the same or slightly lower levels.

These data mean that the cellular precursor of SS is very similar to that of MPNST, presumably a cell derived from the neural crest.

(2) Subclassification of SS

Figure 3A:
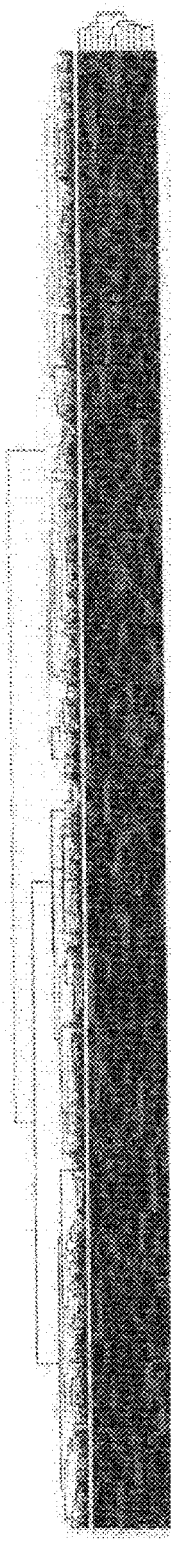
FIG. 3A is a dendrogram showing the overall expression patterns of 1,405 genes in 13 SS cases.
Figure 3B:
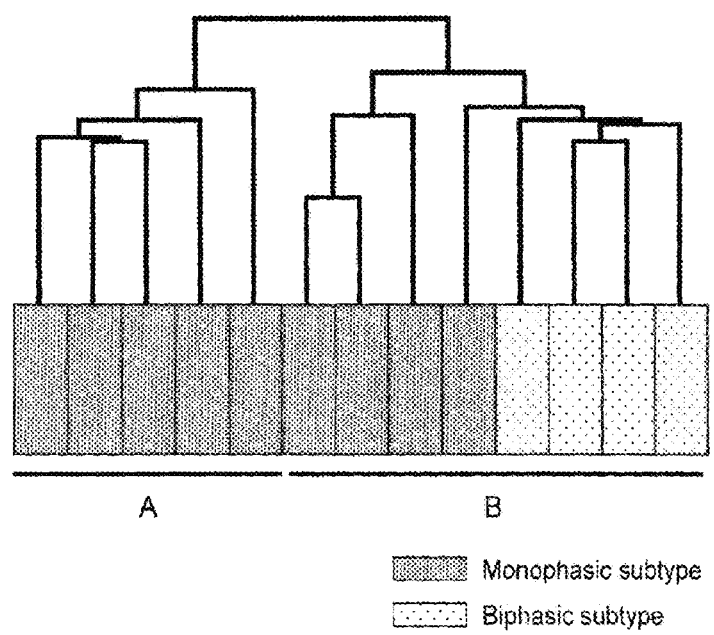
FIG. 3B is a dendrogram showing putative subclasses obtained by cluster analysis; see details in description for FIG. 1. The SS group fell into two biologically distinct subclasses (A and B); tumors with typical monophasic features and with typical biphasic features were each clustered in close relationship and separated from other categories in all cases.

On the basis of the expression patterns of the 1,405 genes we selected (see Example 1), the SS group was subdivided by a clustering analysis into two distinct subclasses (A and B) (FIGS. 3A and 3B). As shown in the hierarchical clustering analysis for all tumors (FIGS. 1A and 1B), four biphasic tumors (SS190, SS334, SS487 and SS582) were again clustered closely, whereas monophasic tumors were divided into two groups. Therefore, the degree of epithelial differentiation may contribute to this subclassification. However, because a tumor (SS646) that showed minimal epithelial differentiation and carried the SYT-SSX2 fusion gene was classified closely to one of the clusters of biphasic type. t is likely that factors other than epithelial differentiation also contribute to this subclassification.

Figure 4:
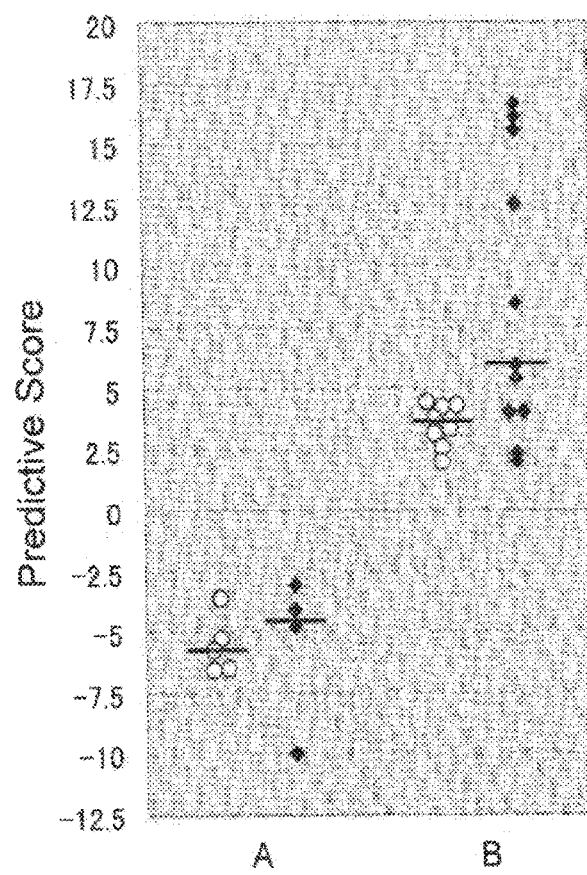
FIG. 4 is a scattered plot showing the predictive scores of SS subclasses (A and B) in 13 learning cases (○) and 15 test cases (♦). Horizontal bar indicates the median value of each group.

A permutation test identified a set of genes that may distinguish the two subclasses (Table 3). Forward stepwise discriminant analysis was applied using 12 candidate genes, and established a predictive formula with discriminant coefficients of 9 predictive genes which were further selected from the 12 genes at a constant value of 6.464 for subclassification of these learning cases (see Example 1, and Table 3). To further verify the power of a set of the nine genes to assign a tumor to one subgroup or the other, their expression levels were also determined by real-time RT-PCR analysis in 15 additional SS cases. In all of these cases SYT-SSX fusion transcripts were identified. SYT-SSX1 genes were identified in 12 cases and SYT-SSX2 in 3 cases. Histologically, 10 of the 15 additional cases were classified into the monophasic subtype, and five into the biphasic subtype. By the predictive formula, the 15 test cases also clearly fell into either subclass A (four cases) or subclass B (11 cases) (FIG. 4). All of the four cases in the subclass A were monophasic, whereas all of the five biphasic cases were assigned to the subclass B, confirming that the subclassification reflected the degree of epithelial differentiation. However, a monophasic case with the SYT-SSX2 gene in the test cases, which may correspond to SS646 in the learning cases, fell into the subclass B, suggesting again that factors other than epithelial differentiation also contribute to this subclassification. These results indicated a use for this set of genes to classify SS cases in terms of their biological properties.

TABLE 3

A list of candidate genes discriminating the SS subgroups

| ID | Hs. | GENE | permutational P | discriminant coefficient |
|---|---|---|---|---|
| A2673 | 2730 | heterogeneous nuclear ribonucleoprotein L | $5.43 \times 10^{-12}$ | |
| B2602 | 3542 | hypothetical protein FLJ11273 | $4.63 \times 10^{-11}$ | −6.035 |
| A2041 | 78596 | proteasome (prosome, macropain) subunit, beta type, 5 | $3.67 \times 10^{-8}$ | −7.187 |
| D5183 | 182740 | ribosomal protein S11 | $8.78 \times 10^{-8}$ | −1.154 |
| C9540 | 91142 | KH-type splicing regulatory protein (FUSE binding protein 2) | $1.99 \times 10^{-7}$ | −2.591 |
| B9386 | 27179 | *Homo sapiens* cDNA FLJ12933 fis, clone NT2RP2004962 | $4.90 \times 10^{-7}$ | |
| A4266 | 82071 | Cbp/p300-interacting transactivator, with Glu/Asp-rich carboxy-terminal domain, 2 | $5.24 \times 10^{-7}$ | 1.777 |
| A5183 | 5011 | RNA binding motif protein 9 | $5.37 \times 10^{-7}$ | 9.412 |
| A1181 | 82173 | TGFB inducible early growth response | $3.39 \times 10^{-6}$ | |
| A1848 | 77840 | annexin A4 | $3.96 \times 10^{-6}$ | −1.933 |
| A8306 | 172572 | hypothetical protein FLJ20093 | $6.71 \times 10^{-6}$ | 7.464 |
| A1887N | 78465 | v-jun avian sarcoma virus 17 oncogene homolog | $1.24 \times 10^{-5}$ | 0.184 |

Hs.; UniGene accession number.

Example 4

Effect on Downregulation of SS-Associated Genes

Figure 5:
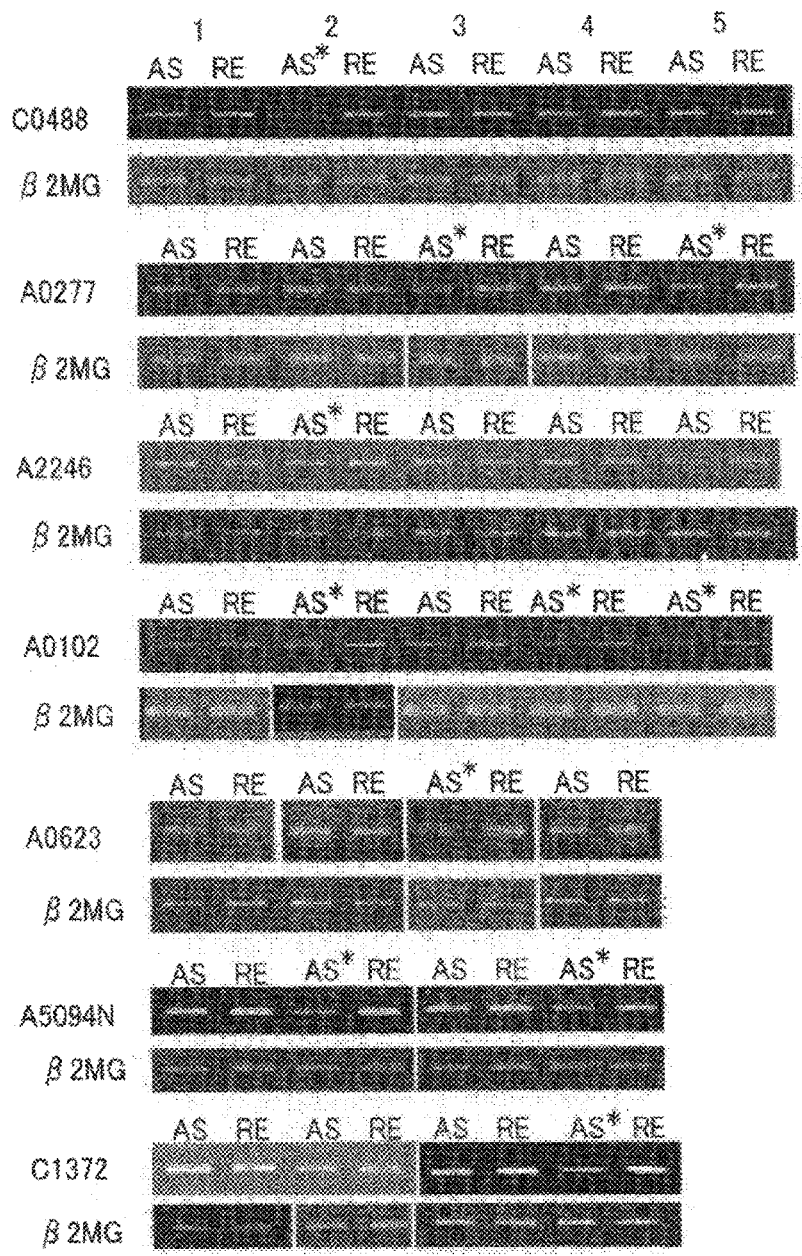
FIG. 5 is a photograph of a blot showing inhibition of mRNA expression by antisense oligonucleotide. β2MG was used as quantity control. Effective antisense oligonucleotides are shown in bold.

To investigate the effect of antisense S-oligonucleotide on the mRNA expression of commonly up regulated genes in SS (Table A), five pairs of control and antisense S-oligonucleotides corresponding in each 7 kinds of known genes out of 26 kinds of up-regulated genes were synthesized Among the 7 genes, mRNA expression was significant suppressed by antisense S-oligonucleotide in C0488, A0277, A2246 A0623, A5094N, A0102 and C1372 (FIG. 5). Sequence of the S-oligonucleotides in each gene were listed in Table 4. In the A0102 (endothelin 3), 3 antisense S-oligonucleotides (A0102AS2 (SEQ ID NO: 136), A0102AS4 (SEQ ID NO: 138) and A0102AS5 (SEQ ID NO: 139)) significant suppressed expression of mRNA compared to the control S-oligonucleotide (A0102RE2 (SEQ ID NO: 141), A0102RE4 (SEQ ID NO: 143) and A0102RE5 (SEQ ID NO: 144)) respectively. In the A0277 (ephrin-B3) and A5094N (collagen type IX, alpha3), 2 antisense 5-oligonucleotides (A0277AS3 (SEQ ID NO: 101), A0277AS5 (SEQ ID NO: 103) and A5094NAS2 (SEQ ID NO: 128), A5094N4 (SEQ ID NO: 130)) significant suppressed mRNA expression in each gene compared to the control S-oligonucleotide (A0277RE3 (SEQ ID NO: 106), A0277RE5 (SEQ ID NO: 108) and A5094NRE2 (SEQ ID NO: 132), A5094NRE4 (SEQ ID NO: 134)) respectively. mRNA expression of C0488 (preferentially expressed antigen in melanoma), A2246 (EphA4), A0623 (dual specificity phodsphatase 9) and C1372 (granin-like neuroendocrine peptide precursor) were inhibited by one kind of antisense S-oligonucleotide compared to control S-oligonucleotide (C0488AS2 (SEQ ID NO: 90), A2246AS2 (SEQ ID NO: 110), A0623AS3 (SEQ ID NO: 121) and C1372AS4 (SEQ ID NO: 148)) significant suppressed mRNA expression in each gene compared to the control S-oligonucleotide (C0488RE2 (SEQ ID NO: 95), A2246RE2 (SEQ ID NO: 115), A0623RE3 (SEQ ID NO: 125) and C1372RE4 (SEQ ID NO: 152)) respectively.

TABLE 4

| SYX Assignment | ID No. | Genbank Accession No. | Oligo Name | Sequence | SEQ ID NO: |
|---|---|---|---|---|---|
| 10 | C0488 | NM_006115 | C0488AS1 | TCGTTCCATTTTGAAGCG | 89 |
|  | * |  | C0488AS2 | CAAACGCCTTCGTTCCAT | 90 |
|  |  |  | C0488AS3 | CATTTTGAAGCGACTTAG | 91 |
|  |  |  | C0488AS4 | AATACAGACCTGTTGACA | 92 |
|  |  |  | C0488AS5 | GCTTGGATTTCTAGGTCT | 93 |
|  |  |  | C0488RE1 | GCGAAGTTTTACCTTGCT | 94 |
|  | * |  | C0488RE2 | TACCTTGCTTCCGCAAAC | 95 |
|  |  |  | C0488RE3 | GATTCAGCGAAGTTTTAC | 96 |
|  |  |  | C0488RE4 | ACAGTTGTCCAGACATAA | 97 |
|  |  |  | C0488RE5 | TCTGGATCTTTAGGTTCG | 98 |
| 8 | A0277 | NM_001406 | A0277AS1 | CCATGACCCCGCCAAG | 99 |
|  |  |  | A0277AS2 | TGCCTGGCTCTTCAGC | 100 |
|  | * |  | A0277AS3 | ACCAACTCCCCCAAAGT | 101 |
|  |  |  | A0277AS4 | TAGCTATACTTATTCATA | 102 |
|  | * |  | A0277AS5 | TAAAAGTGGAGACGAGGA | 103 |
|  |  |  | A0277RE1 | GAACCGCCCCAGTACC | 104 |
|  |  |  | A0277RE2 | CGACTTCTCGGTCCGT | 105 |
|  | * |  | A0277RE3 | TGAAACCCCCTCAACCA | 106 |
|  |  |  | A0277RE4 | ATACTTATTCATATCGAT | 107 |
|  | * |  | A0277RE5 | AGGAGCAGAGGTGAAAAT | 108 |
| 11 | A2246 | NM_004438 | A2246AS1 | ATGGTTCGCCGGTGCCAA | 109 |
|  | * |  | A2246AS2 | AAATAGAAAATCCCGCAT | 110 |
|  |  |  | A2246AS3 | AAAATCCCGCATGGTT | 111 |
|  |  |  | A2246AS4 | GGCTCTTACCTTCATTCG | 112 |
|  |  |  | A2246AS5 | TTCTCTTCTGAGTTGT | 113 |
|  |  |  | A2246RE1 | AACCGTGGCCGCTTGGTA | 114 |
|  | * |  | A2246RE2 | TACGCCCTAAAAGATAAA | 115 |
|  |  |  | A2246RE3 | TTGGTACGCCCTAAAA | 116 |
|  |  |  | A2246RE4 | GCTTACTTCCATTCTCGG | 117 |
|  |  |  | A2246RE5 | TGTTGAGTCTTCTCTT | 118 |
| 5 | A0623 | NM_001395 | A0623AS1 | TCCATGGGCGATCGGCT | 119 |
|  |  |  | A0623AS2 | GAAGTTTCCGAAGCTC | 120 |
|  | * |  | A0623AS3 | CGATCGGCTCCCTACA | 121 |
|  |  |  | A0623AS4 | AAGAAAAAGTAACAGT | 122 |
|  |  |  | A0623RE1 | TCGGCTAGCGGGTACCT | 123 |
|  |  |  | A0623RE2 | CTCGAAGCCTTTGAAG | 124 |
|  | * |  | A0623RE3 | ACATCCCTCGGCTAGC | 125 |
|  |  |  | A0623RE4 | TGACAATGAAAAAGAA | 126 |
| 4 | A5094N | NM_001853 | A5094AS1 | CGCGCGGCCCGGCCAT | 127 |
|  | * |  | A5094AS2 | TTCTCCGTCAATGCCGT | 128 |
|  |  |  | A5094AS3 | ACCAGCTTCTCCGTCAAT | 129 |
|  |  |  | A5094AS4 | GCCTTTGTCTCCTCTG | 130 |
|  |  |  | A5094RE1 | TACCGGCCCGGCGCGC | 131 |
|  | * |  | A5094RE2 | TGCCGTAACTGCCTCTT | 132 |
|  |  |  | A5094RE3 | TAACTGCCTCTTCGACCA | 133 |
|  | * |  | A5094RE4 | GTCTCCTCTGTTTCCG | 134 |

TABLE 4-continued

| SYX Assignment ID | Genbank No. Accession No. | Oligo Name | Sequence | SEQ ID NO: |
|---|---|---|---|---|
| 3 | A0102 NM_000114 | A0102AS1 | GGCTCCATGAACCTAGAT | 135 |
| * | | A0102AS2 | CATGAACCTAGATCAGGC | 136 |
| | | A0102AS3 | CTCCATGAACCTAGATCA | 137 |
| * | | A0102AS4 | TGCGCTTACCTGCGGC | 138 |
| * | | A0102AS5 | ACTAACTTTCTCATTTTC | 139 |
| | | A0102RE1 | TAGATCCAAGTACCTCGG | 140 |
| * | | A0102RE2 | CGGACTAGATCCAAGTAC | 141 |
| | | A0102RE3 | ACTAGATCCAAGTACCTC | 142 |
| * | | A0102RE4 | CGGCGTCCATTCGCGT | 143 |
| * | | A0102RE5 | CTTTTACTCTTTCAATCA | 144 |
| 13 | C1372 AF181562 | C1372AS1 | CATGCTGCCCCAGCGA | 145 |
| | | C1372AS2 | AGCAGCAGCACCAAAA | 146 |
| | | C1372AS3 | AAACAGGCCGAGCAGCA | 147 |
| * | | C1372AS4 | AGATCATGTTTATTGTGG | 148 |
| | | C1372RE1 | AGCGACCCCGTCGTAC | 149 |
| | | C1372RE2 | AAAACCACGACGACGA | 150 |
| | | C1372RE3 | ACGACGAGCCGGACAAA | 151 |
| * | | C1372RE4 | GGTGTTATTTGTACTAGA | 152 |

*effective

Example 5

Recombinant Protein and Polyclonal Antibody

The recombinant protein of the N-terminal extracellular domain of FZD10 (FZD10-ECD; residues 1-225 of the amino acid sequence shown in SEQ ID NO: 153) fused with His tag was produced in *E. coli* using the pET28 expression system (Novagen, Madison, Wis.). Briefly, expression of the protein was induced by 0.5 mM isopropyl β-D-thiogalactopyranoside (IPTG) by incubation at 25° C. for 3 h and then purified with Ni-NTA resin (QIAGEN, Valencia, Calif.) according to the manufacturer's instructions. Rabbits were immunized with the purified recombinant protein (Medical & Biological Laboratories, Nagoya, Japan), and then the high-titer antiserum was purified using Affi-Gel 15 support (Bio-Rad, Hercules, Calif.), which was coupled with FZD10-ECD recombinant protein in a coupling solution (20 mM HEPES, 150 mM NaCl, pH 8.0). Antibody bound to the gel was eluted from the column in 0.1 M glycine (pH 2.5) and immediately neutralized in 1 M Tris (pH 8.5). The quality and specificity of the affinity-purified polyclonal antibody (hereinafter referred to "TT641 pAb") was verified by SDS-polyacrylamide gel electrophoresis (PAGE) and Western blotting.

Example 6

Expression of FZD10

(1) Preparation of Cell Lines and Tissue Specimens

SS cell lines (HS-SY-2, YaFuSS and SYO-1), colon cancer cell lines (SW480, LoVo, DLD1, HT29, HCT116, SNU-C4 and SNU-05), a cervical adenocarcinoma cell line (HeLa), a fibrosarcoma cell line (HT1080), and COST were grown in monolayers in appropriate media supplemented with 10% fetal bovine serum and 1% antibiotic/antimycotic solution (Sigma, St Louis, Mo.) and maintained at 37° C. in air containing 5% $CO_2$. Tumor samples were snap-frozen in liquid nitrogen immediately after resection and stored at −80° C. until preparation of RNA. Surgical specimens were also fixed in 10% formalin and routinely processed for paraffin embedding. The paraffin block was thin-sectioned serially to 5 μm thickness and stained with HE (hematoxylin-eosin) for pathological evaluation. All samples were approved for our analysis by the ethical committee of the Faculty of Medicine, Kyoto University.

(2) Northern-Blot Analysis

Total RNAs were extracted from cell lines and from frozen surgical specimens prepared in (1) above using TRIzol reagent (Invitrogen, Carlsbad, Calif.) according to the manufacturer's instructions. After treatment with DNase I (Nippon Gene, Osaka, Japan), mRNA was isolated with Micro-Fast-Track (Invitrogen) following the manufacturer's instructions. A 1-μg aliquot of each mRNA, along with human normal tissue poly A (+) RNA isolated from the heart, brain, lung, liver, kidney, bone marrow, pancreas and placenta (Clontech, Palo Alto, Calif.) was separated on a 1% denaturing agarose gel and transferred to a nylon membrane. Hybridization with a random-primer $\alpha^{32}$P-dCTP labeled FZD10 cDNA probe was carried out according to the instructions for the Megaprime DNA labeling system (Amersham Bioscience). Prehybridization, hybridization, and washing were performed according to the supplier's recommendations. The blots were autoradiographed with intensifying screens at −80° C. for three days.

Northern blot analysis revealed that the highest level of FZD10 was expressed in placenta among normal human adult tissues (FIG. 6A), which was consistent with a previous report (Koike, J. et al., Biochem Biophys Res Commun. 262: 39-43., 1999). As compared to the level of transcripts in placenta, FZD10 gene was expressed in SS cell lines (HS-SY-2 and YaFuSS) and surgical SS specimens (SS487 and SS582) at much higher levels. These findings indicate that transcription of FZD10 increased in SS tumor cells.

Example 7

Specific Recognition of Extracellular Domain of FZD10 by TT641 pAb (1) Western Blotting The present inventors generated the polyclonal antibody that recognized the N-terminal extracellular domain of FZD10 (FZD10-ECD) (see Example 6). To investigate the specificity of the affinity-purified FZD10-ECD antibody (TT641 pAb), Western blotting analyses were performed as following:

For complete solubilization of whole-cell proteins, adherent cells were collected in Laemmli sample buffer (BioRad), lysed with sonication, and boiled for 5 min. Each sample was loaded onto a 10% SDS-PAGE gel, blotted onto a nitrocellulose membrane (Amersham Bioscience) and incubated at 4° C. overnight at 0.1 µg/ml of TT641 pAb. Following 1 h of incubation with anti-rabbit HRP-conjugated immunoglobulin (Amersham Bioscience), signals were visualized using enhanced chemiluminescent reagent (ECL) (Amersham Bioscience). As a loading control for proteins, β-actin was detected by monoclonal anti-β-actin AC-15 (Sigma).

Figure 7:
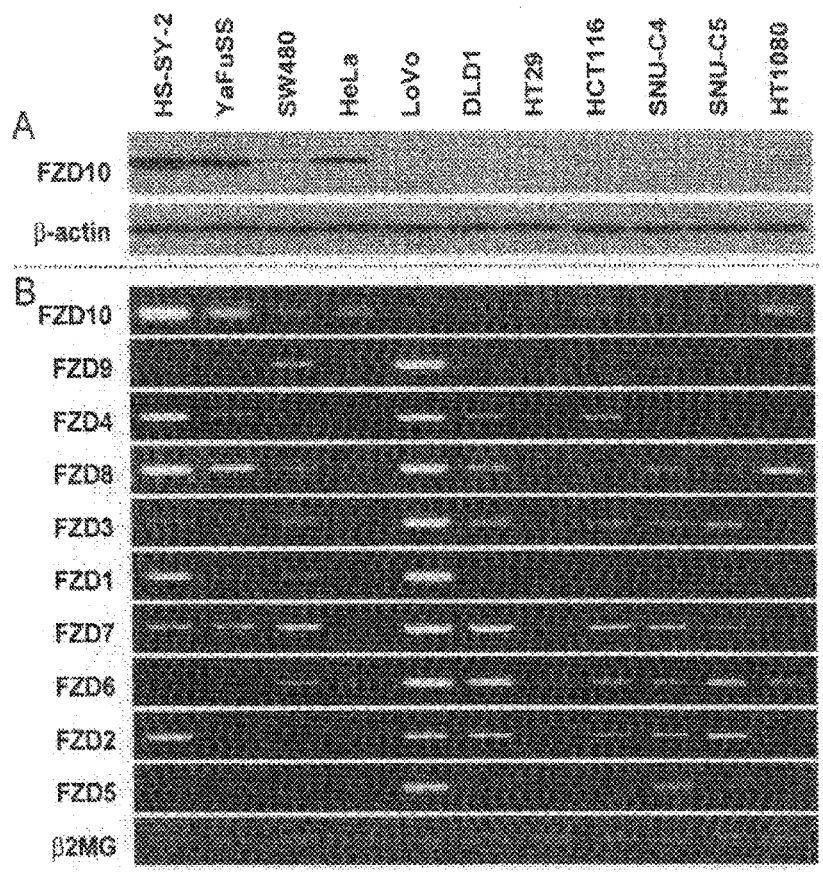
FIGS. 7A and 7B are photographs showing the specificity of the affinity-purified FZD10-ECD antibody (TT641 pAb) that recognized the N-terminal extracellular domain of FZD10 (FZD10-ECD).

As a result, a single 68-kDa band of the predicted size compatible to FZD10 was clearly observed in FZD10-expressing cell lines (FIG. 7A). However, since the sizes of the other FZD gene family proteins are similar to that of FZD10 protein, we further examined whether the single band recognized by TT641 pAb was specific to the FZD10 protein by semi-quantitative RT-PCR as following.

(2) Semi-Quantitative RT-PCR

A 3-µg aliquot of total RNA prepared from each cell line was reverse-transcribed for single-stranded cDNAs using oligo(dT)$_{12-18}$ primer and Superscript II (Invitrogen). Semi-quantitative RT-PCR was carried out with the primers specific to each member of the FZD family or with a β2-microglobulin (β2MG)-specific primer as an internal control. The primer sequences are listed in Table 5.

cell lines. This finding indicates that TT641 pAb recognized the specific epitope of FZD10 but not other members of the FZD gene family.

Example 8

Localization of FZD10 in Cells (1) Immunocytochemistry

Figure 8:
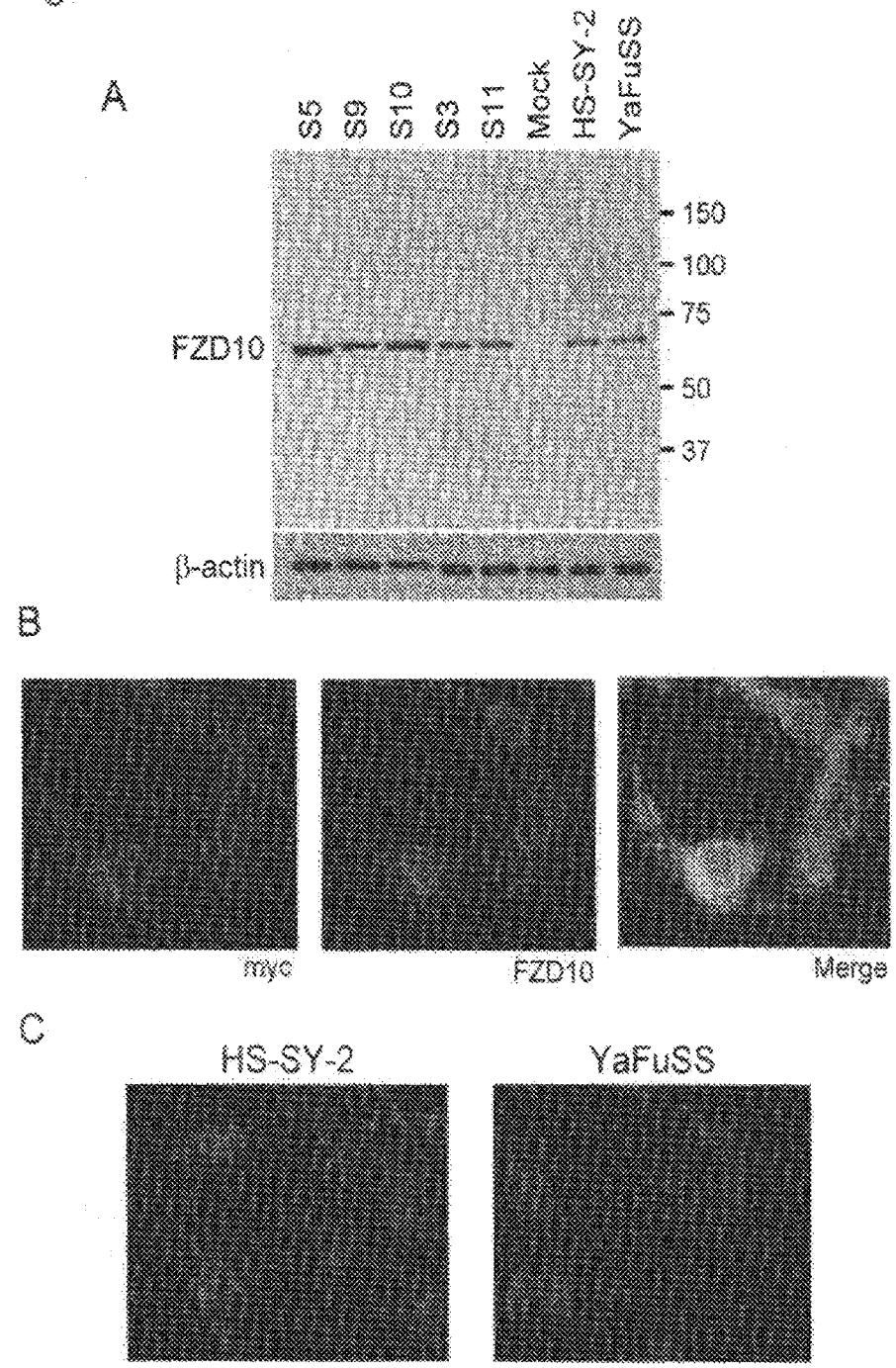
FIGS. 8A, 8B and 8C are photographs showing subcellular localization of FZD10 protein with immunocytochemical analysis.

To examine the subcellular localization of FZD10 protein, we performed immunocytochemical analysis. We initially established COS7-FZD10 cells (S5, S9, S10, S3 and S11) that stably over-expressed FZD10 by transfecting an expression construct of pCAGGS-FZD10-Myc-His into COS7 cells (FIG. 8A).

Firstly, the entire coding sequence of FZD10 cDNA was amplified by RT-PCR using KOD-Plus DNA polymerase (TOYOBO, Osaka, Japan) and inserted into the unique EcoRI site of the pCAGGS mammalian expression vector, which carries a CAG (cytomegalovirus immediate-early enhancer chicken β-actin hybrid) promoter (Niwa, H. et al., Gene. 108: 193-9., 1991) and a gene conferring neomycin resistance. Myc and His epitope tags were placed at the C terminus of the expression vector (pCAGGS-FZD10-Myc-His). Constructs were confirmed by DNA sequencing with forward and reverse primers; forward, 5'-GTCCCCTTCTCCATCTC-CAG-3' (SEQ ID NO: 175); reverse, 5'-TATTTGTGAGC-CAGGGCATT-3' (SEQ ID NO: 176).

Then, COS7 cells were seeded at 5×10$^4$ cells per six-well plate. After 24 h, cells were transfected with 2 µg of pCAGGS-FZD10-Myc-His mixture pre-incubated for 15 min with 6 µl of FuGene6 transfection reagent (Roche, Basel, Switzerland). Following a three-week culture period in selective medium containing 0.4 mg/ml of Geneticin (Invitrogen), stable transfectants were established.

TABLE 5

Primer sequences FZD gene family

| | Primer F | Primer R |
|---|---|---|
| FZD1 | 5'-CTCGAGGTTTCCTCACTAGACAA-3' (SEQ ID NO: 155) | 5'-AATGGTTAAACCGCCCTAAATAA-3' (SEQ ID NO: 156) |
| FZD2 | 5'-TCCACCTTCTTCACTGTCACC-3' (SEQ ID NO: 157) | 5'-TAAAATACGGAGTCTGTAGGGGC-3' (SEQ ID NO: 158) |
| FZD3 | 5'-ATTGAATAGGCCTGATCATCTGA-3' (SEQ ID NO: 159) | 5'-ATAGGAGCGTAGAGTGCACAAAG-3' (SEQ ID NO: 160) |
| FZD4 | 5'-ATGACTTACAGATCCCCCGAC-3' (SEQ ID NO: 161) | 5'-ACAGAGCAGGGGAAGTCACAT-3' (SEQ ID NO: 162) |
| FZD5 | 5'-CTGCGCTTCTTCCTATGCACTA-3' (SEQ ID NO: 163) | 5'-TTGTTGTAGAGCGGGTGTGACT-3' (SEQ ID NO: 164) |
| FZD6 | 5'-CGCTACTTTGTACTCTTGCCACT-3' (SEQ ID NO: 165) | 5'-ACATGGGATATGGTACTGACGAC-3' (SEQ ID NO: 166) |
| FZD7 | 5'-GCGAGGCGCTCATGAACAAGT-3' (SEQ ID NO: 167) | 5'-CACGGCCACCATGAAGTAGCA-3' (SEQ ID NO: 168) |
| FZD8 | 5'-GACACTTGATGGGCTGAGGTTC-3' (SEQ ID NO: 169) | 5'-TAAGTCAGGGGTGGGAGTTTAC-3' (SEQ ID NO: 170) |
| FZD9 | 5'-CTGCACGCTGGTCTTCCTACT-3' (SEQ ID NO: 171) | 5'-CCGATCTTGACCATGAGCTTC-3' (SEQ ID NO: 172) |
| FZD10 | 5'-TCAGAAACCCTTCAGTGCTACAT-3' (SEQ ID NO: 173) | 5'-ATACACACGCAGAAACCACTCTT-3' (SEQ ID NO: 174) |

Primer F or R; forward or reverse primer sequences, respectively

The results are shown in FIG. 7B. The expression pattern found in Western blotting (FIG. 7A) was compared to the levels of transcripts in 10 members of the FZD family using various cell lines (FIG. 7B). As shown in FIGS. 7A and 7B, the expression pattern detected with Western blotting using TT641 pAb was quite similar to those of the FZD10 transcripts revealed by semi-quantitative RT-PCR among 10 members of the FZD family, especially in the HeLa and LoVo COS7-derived stable transfectants expressing FZD10 were fixed with 4% paraformaldehyde in PBS and then covered with blocking solution (3% BSA) for 1 h at room temperature. To minimize cell lysis, permealization with detergents was not performed. The cells were then incubated with mouse anti-c-myc antibody (9E10, diluted 1:1000) and with the TT641 pAb (2 µg/ml) in blocking solution at 4° C. overnight. Primary antibodies were stained with goat anti-rabbit secondary fluorescent antibodies (Alexa Flour 488; diluted 1:500, Molecular Probes) and horse anti-mouse secondary antibodies conjugated with Texas Red (diluted 1:1000, Vector Laboratories, Burlingame, Calif.) for 1 h at room temperature, stained with DAPI (4',6-diamidino-2-phenylindole) and visualized with an ECLIPSE E 600 microscope (Nikon, Tokyo, Japan). To detect the endogenous expression patterns of FZD10, SS cell lines (HS-SY-2 and YaFuSS) were also fluorescence immunostained with 2 µg/ml of TT641 pAb in the same manner.

When COS7-FZD10 cells were counterstained with Texas Red-conjugated anti-myc antibody, the red signal coincided with the green one of the TT641 pAb (FIG. 8B), supporting the specific binding of the TT641 pAb to FZD10. Furthermore, the immunocytochemical analysis using TT641 pAb revealed that endogenous expression patterns observed in SS cell lines (HS-SY-2 and YaFuSS) were similar to those in stable transfectants (FIG. 8C). The reason why FZD10 stained in a dotted pattern in the cytoplasm remains unclear, although the predicted FZD10 protein is known to be a seven-pass transmembrane receptor (Koike, J. et al., Biochem Biophys Res Commun 262: 39-43., 1999). Presumably, the mature cell-surface antigen appeared in relatively low concentrations and abundant unprocessed antigens in the cytoplasm may be detected in immunocytochemistry.

(2) Flow Cytometric Analysis

To address the question as to the subcellular localization raised in the immunocytochemistry section, flow cytometric analysis was performed.

$5 \times 10^6$ cells were collected by trypsinization and incubated with 1.5 µg of TT641 pAb and non-immunized rabbit IgG (DAKO, Kyoto, Japan) at 4° C. for 30 min. After washing 3 times with PBS, 2 µg of fluorescent anti-rabbit IgG (Alexa Fluor 488, Molecular Probe) was added to the cell suspension and incubated at 4° C. for 30 min. Immediately after washing three times with PBS, cells were analyzed by a FACScan (Becton Dickinson, San Jose, Calif.).

Figure 9:
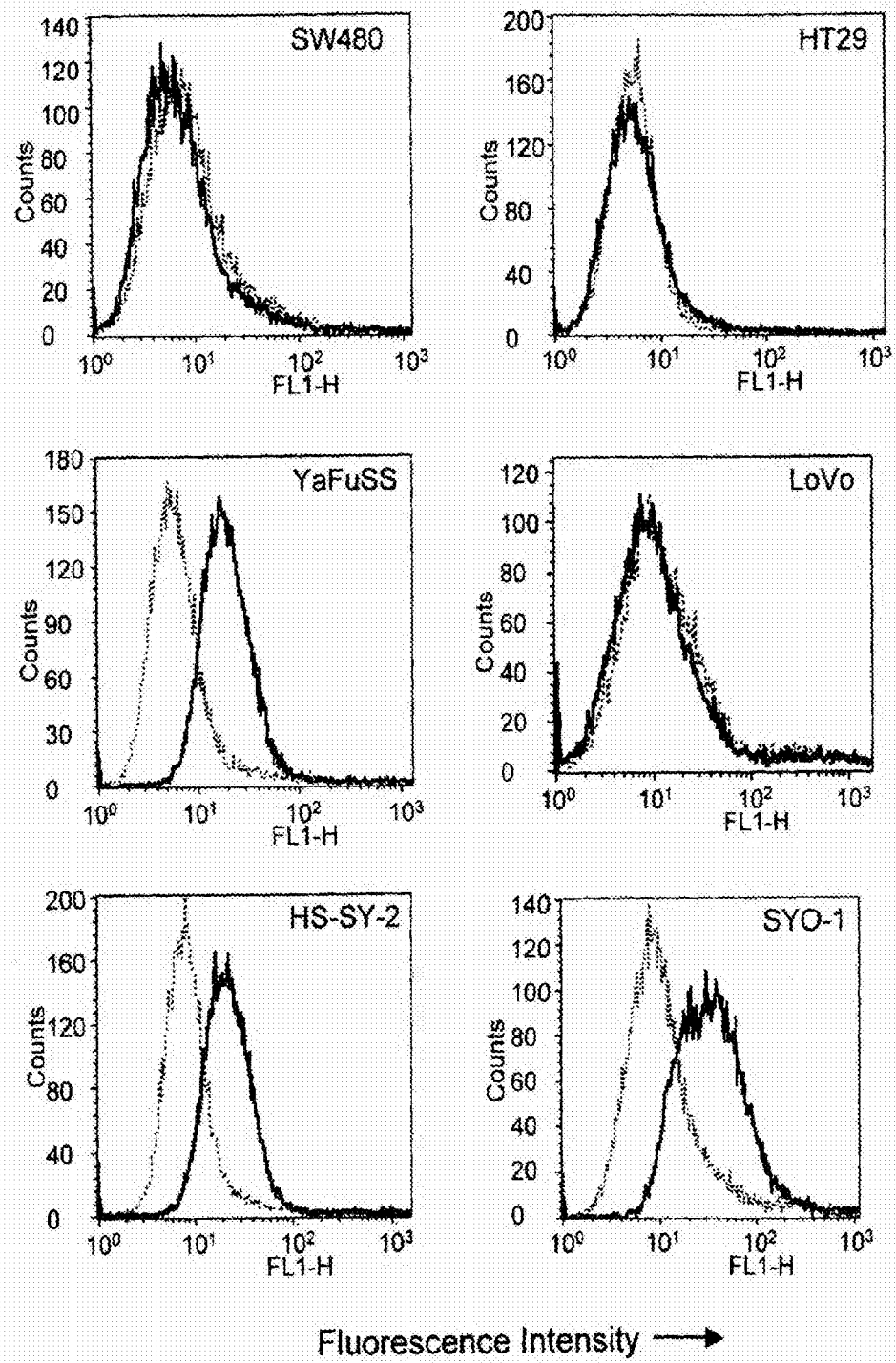
FIG. 9 shows a flow cytometric analysis using TT641 pAb in several tumor cell lines. Solid lines show the expression level of FZD10, a cell-surface antigen, detected with TT641 pAb, whereas broken lines depict the fluorescent signal of cells incubated with non-immunized rabbit IgG as a negative control.

Three SS cell lines, YaFuSS, HS-SY-2, and SYO-1, were specifically labeled with the TT641 pAb (FIG. 9), whereas no fluorescence signals were detected in SW480, HT29, or LoVo cell lines. These observations were correlated with the expression levels of FZD10 observed in Northern blots (see, Example 5, FIG. 6B). Taken together, these findings indicate that the TT641 pAb specifically recognizes the cell-surface antigen of FZD10, but not any other FZD members (FIGS. 7A and 7B), under both native and denaturing conditions.

Example 9

Epitope Mapping of TT641 pAb

To characterize the specificity of TT641 pAb, we initially performed epitope mapping using SPOTs system as following:

A series of 10-residue linear peptides overlapping by one amino acid and covering the entire sequence of FZD10-ECD (residues 1-225 of the amino acid sequence shown in SEQ ID NO: 153) was synthesized and covalently bound to a cellulose membrane by the SPOT synthesis technique (SPOTs; Sigma Genosys). According to the manufacturer's recommendations, the membrane containing 216 peptide spots was preincubated for 8 h at room temperature with a blocking buffer (Sigma) and hybridized with TT641 pAb in the blocking buffer at 4° C. overnight. The membrane was washed with 0.05% Tween 20/TBS (50 mM Tris, 137 mM NaCl and 2.7 mM KCl, pH 8.0), followed by 2 h of incubation of anti-rabbit immunoglobulin conjugated with horseradish peroxidase (HRP) (Amersham Bioscience) in the blocking buffer at room temperature. After three washes with 0.05% Tween 20/TBS, the spots were visualized with signal development solution (Sigma) containing 3-amino-9-ethylcarbazole.

Figure 10:
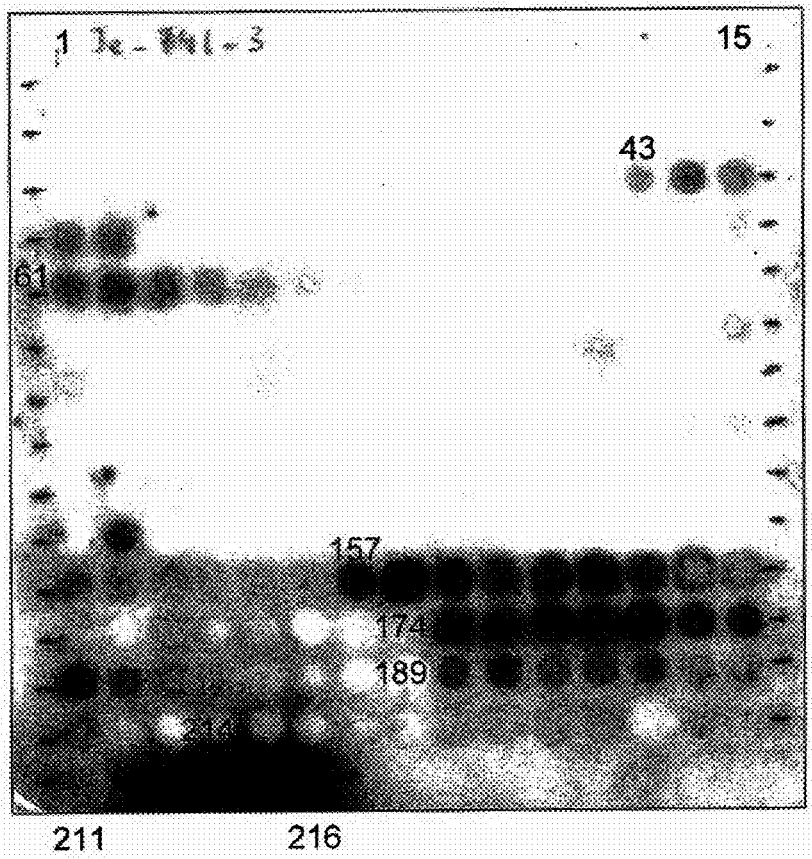
FIG. 10 is a photograph showing an epitope mapping of TT641 pAb with synthetic overlapping linear peptides. The membrane containing a series of 10-residue peptides differing by one amino acid and covering the entire amino acid of FZD10-ECD was probed with TT641 pAb, and the binding was detected with HRP-conjugated goat anti-rabbit IgG. Bold letters indicate the possible core epitopes of FZD10-ECD.

As a result, TT641 pAb recognized 6 different epitopes of FZD10-ECD to a different degree (FIG. 10). Among them, TT641 pAb showed the strongest reactivity to the epitope ranging from 214-225 residues, which was thought to represent a critical sequence for specific binding of TT641 pAb to FZD10-ECD.

Example 10

Expression Pattern of FZD10 Protein (1) Immunohistochemical Staining

To investigate whether TT641 pAb could specifically recognize FZD10 protein in tissue sections, we initially performed immunohistochemical analyses in normal adult human tissues and SS surgical specimens using the TT641 pAb.

Each serial section of the paraffin-embedded specimens was mounted on a silanized slide, deparaffinized in xylene and rehydrated in phosphate buffered saline (PBS). The sections were then processed for antigen retrieval by microwave treatment. After quenching endogenous peroxidase activity with 3% hydrogen peroxide, non-specific binding of primary antibodies was blocked with a blocking reagent (DAKO). The slides were then incubated at 4° C. overnight with TT641 pAb at 5 µg/ml. Subsequently, rabbit ENVISION Polymer Reagent (DAKO) was added as a secondary antibody for 60-mins reaction at room temperature. Finally the immunoreaction was visualized with peroxidase substrate 3, 3'-diaminobenzidine tetrahydrochloride (DAKO). The sections were counterstained with hematoxylin, dehydrated in graded alcohols, cleared in xylene, and coverslipped. Negative controls were run in parallel with replacement of the specific antibody with non-immune normal rabbit IgG (DAKO). Paraffin-embedded slides of human adult normal tissues were purchased from DAKO and BioChain (Hayward, Calif.), and immunostained in the same manner as mentioned above.

Figure 6:
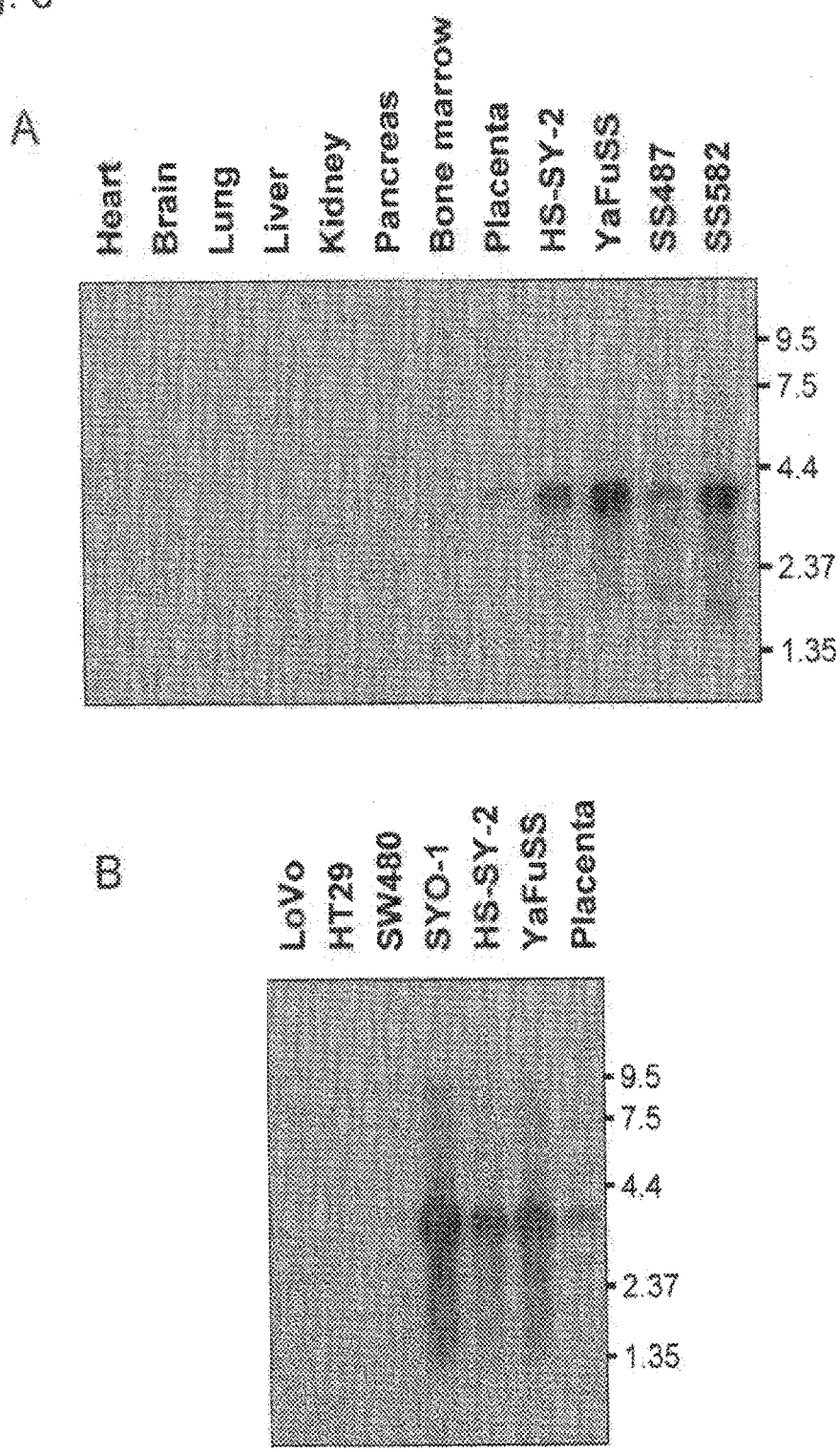
FIG. 6A is a photograph showing a Northern blot analysis of FZD10 in normal human adult tissues (heart, brain, lung, liver, kidney, pancreas, bone marrow, and placenta), SS cell lines (HS-SY-2 and YaFuSS) and surgical SS specimens (SS487 and SS582).
FIG. 6B is a photograph showing a northern blot analysis of FZD10 in colon cancer cell lines (LoVo, HT29 and SW480) and SS cell lines (SYO-1, HS-SY-2, and YaFuSS).
Figure 11:
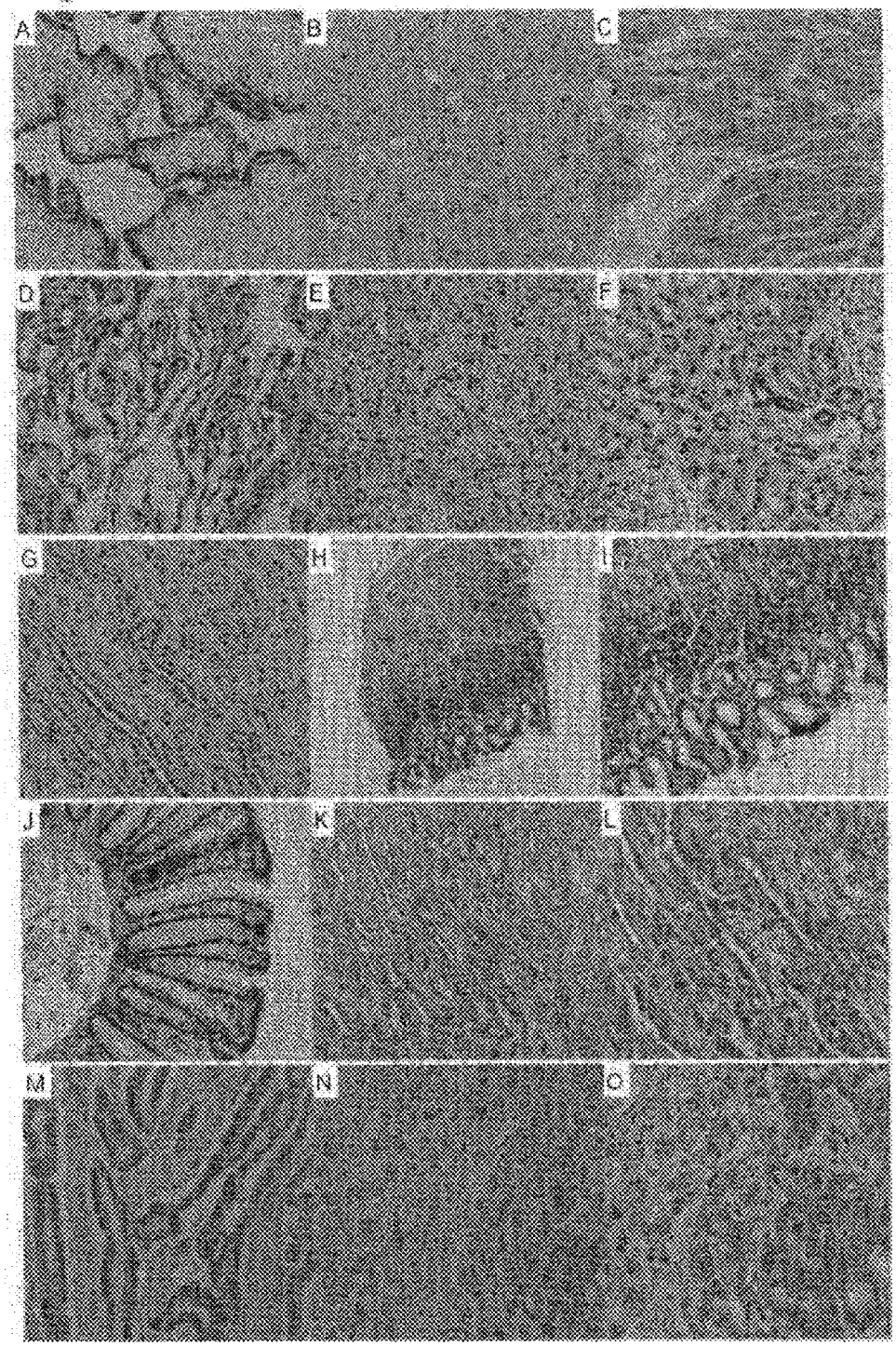
FIGS. 11A to 11O are photographs showing immunohistochemical analysis using the TT641 pAb in normal adult human tissues, SS tumor tissues, primary colon cancer, and metastatic liver lesions of the colon cancer. In these figures, A=placenta, B=brain, C=heart, D=lung, E=liver, F and G=kidneys from different individuals, H and I=stomach from the same individual, J=colon, K and L=SS tumor cells of the same biphasic SS specimen, and M, N, and O=primary colon cancer and its metastatic liver lesion of the same patient. The original magnification of A, B, C, D, E, F, G, I, J, K, and M=×100; H and N=×40; L and O=×200.

In contrast to positive staining for FZD10 in placenta (FIG. 11A), no expression of FZD10 was detected by immunostaining with TT641 pAb in five different tissue sections of normal brain (FIG. 11B), heart (FIG. 11C), lung (FIG. 11D) or liver (FIG. 11E), as expected from the Northern blots (see, Example 6, FIG. 6A). In normal kidney, however, positive staining was observed in the proximal and distal tubules and collecting tubes (FIG. 11F), although the degree of staining intensity varied between individuals (FIG. 11G). In normal stomach tissues, strong immunoreactivity was observed in the upper portion of gastric glands, but the staining intensity was much weaker in cells located at the bottom of the glands (FIGS. 11H and 11I). In normal colon tissues as well, epithelial cells showed faint immunoreactivity of FZD10 at the bottom of the crypts, but strong staining intensity was detected at the surface of the villi (FIG. 11J). In contrast, strong expression of FZD10 was found in a cytoplasmic pattern in SS tumor cells of the biphasic SS specimen (FIGS.

11K and 11L). It is noteworthy that staining intensity was especially strong in epithelial tumor cells, whereas non-epithelial spindle tumor cells showed faint immunoreactivity. These data suggested that expression levels of FZD10 protein was also absent or low in normal vital organs, compared to the increased expression in SS tissues. In addition, colon cancer cells in the primary and metastatic lesions were also specifically immunostained with TT641 pAb, but not detectable signals in the surrounding stromal and liver tissues (FIGS. 11M, 11N and 11O).

Example 11

TT641 pAb Mediates ADCC Against FZD10-Expressing SS Cells

To further examine whether the TT641 pAb induces antibody-dependent cell-mediated cytotoxicity (ADCC) against SS cells, we measured LDH release from SS cells upon cell lysis.

Cytotoxicity was assayed by quantitative measurement of lactate dehydrogenase (LDH), a stable cytosolic enzyme that is released upon cell lysis, using CytoTox96 Non-radioactive Cytotoxicity Assay (Promega, Madison, Wis.). For the preparation of fresh effector cells, peripheral blood mononuclear cells (PBMCs) were isolated from heparinized peripheral blood of a healthy donor by Ficoll-Paque (Amersham Bioscience) density gradient centrifugation. Following the manufacturer's instructions, effector cells (E) and target cells (T) ($5\times10^3$/well) were co-incubated at various E:T ratios together with TT641 pAb or non-immunized rabbit IgG in 100 µl of phenol red-free RPMI 1640 supplemented with 5% FBS in a 96-well round-bottom plate in quadruplicate for 6 h at 37° C. Released LDH in the culture supernatant (50 µl) was measured by a colorimeric assay, which results in the conversion of a tetrazolium salt into a red formazan product. Absorbance data at 490 nm were collected with a standard 96-well plate reader. After the data were corrected for background signals, the percentage of specific cytotoxicity was calculated according to the formula: % cytotoxicity=100×(experimental LDH release−effector spontaneous LDH release−target spontaneous LDH release)/(target maximal LDH release−target spontaneous LDH release). Controls included the incubation of either target or effector cells with TT641 pAb.

Figure 12:
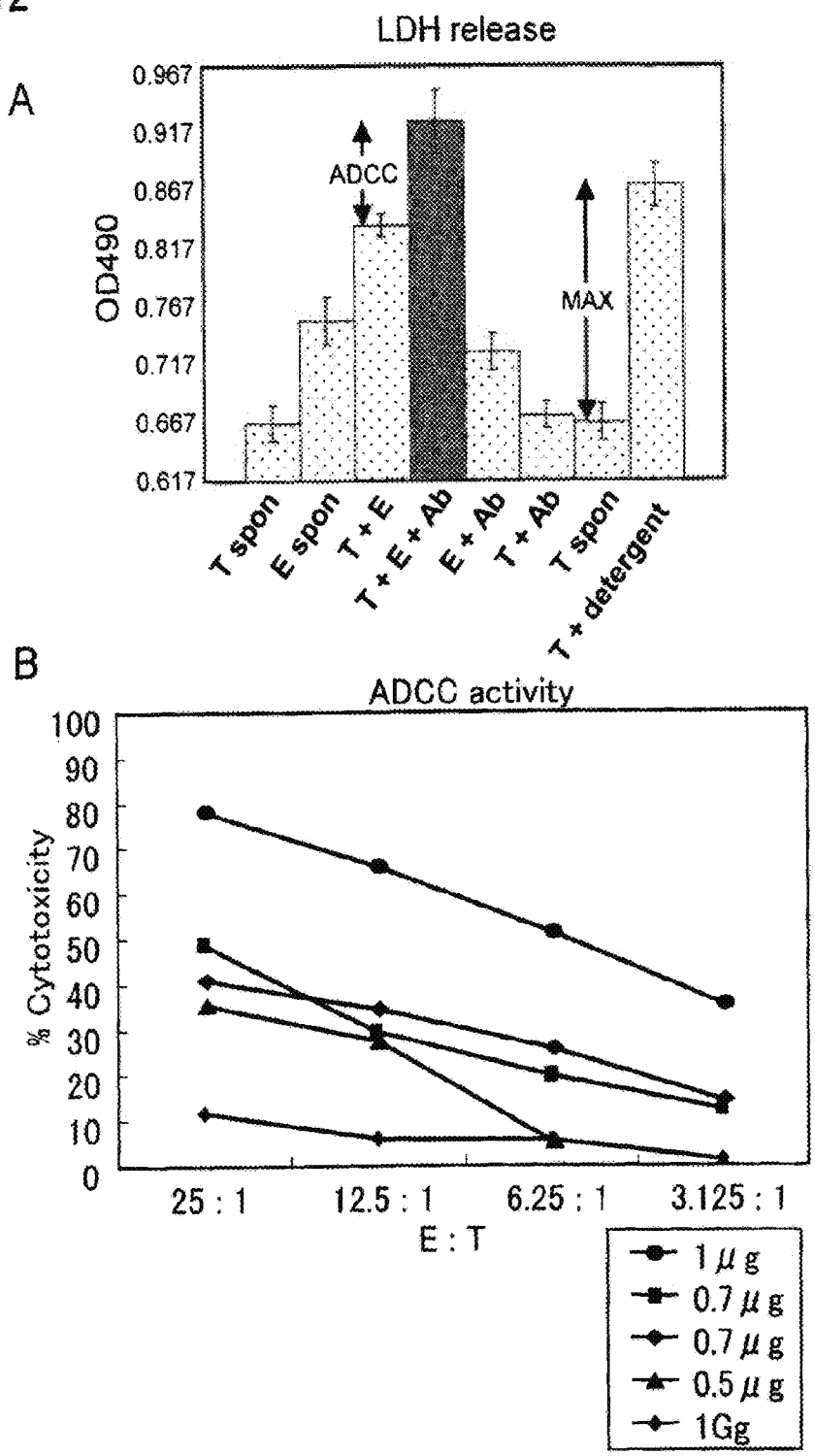
FIG. 12A is a photograph showing TT641 pAb mediated ADCC against FZD10-overexpressing cells. Cytotoxicity was assayed by quantitative measurement of released lactate dehydrogenase (LDH) upon cell lysis, when target and effector cells were co incubated with 7 µg/ml of TT641 pAb at an E:T ratio of 25:1. In this figure, T=target cells (SYO-1), E=effector cells (PBMCs), T spon=spontaneous release of LDH from target cells, E spon=spontaneous release of LDH from effector cells, and Ab=TT641 pAb.
FIG. 12B is a photograph showing that TT641 pAb mediated ADCC against FZD10-overexpressing cells. Cell-mediated cytotoxicity against FZD10-overexpressing cells at several E:T ratios, indicating positive correlation with the amount of TT641 pAb added to the medium.

As shown in FIG. 12A, when target and effector cells were co-incubated with 7 µg/ml (0.7 µg/well) of TT641 pAb at an E:T ratio of 25:1, there were no cytotoxic effects in the target cell line (SYO-1) with TT641 pAb alone (T+Ab), and no evidence of cytotoxic interaction between the TT641 pAb and the human effector cells (E+Ab) or between the target cells and the human effector cells (T+E). On the other hand, cytotoxic effects were observed when the target cells were incubated with both the antibody and human effector cells (T+E+Ab). Even when the target cells were incubated with different concentrations of TT641 pAb in different E:T ratios, cytotoxicity was induced only when both the antibody and human effector cells were added at the same time.

As shown in FIG. 12B, 1 µg of the TT641 pAb induced 78% of cell-mediated cytotoxicity against FZD10-overexpressing cells at an E:T ratio of 25:1. This cytotoxic effect was positively correlated with the E:T ratios and the amount of the antibody added. There was no significant ADCC induced by control antibody against the target cells. These results suggested the possibility that TT641 pAb against FZD10 could exhibit a growth inhibitory effect for FZD10-overexpressing tumors through ADCC.

Example 12

Growth Inhibitory Effect of TT641 pAb on SS Xenografts

In this Example, mice were inoculated subcutaneously with SYO-1 cells to examine the growth inhibitory effect of TT641 pAb on SS xenografts.

Animal work was performed in the animal facility in accordance with institutional guidelines. Female 6-week-old athymic mice (BALB/cA Jcl-nu) were used. Mice were acclimated and housed in sterile cages in groups of 3 under laminar flow hoods in a temperature-controlled room with a 12-hour light/12-hour dark schedule, and fed autoclaved chow and water ad libitum.

For the cell implantations, SYO-1 cells, grown in monolayers, were trypsinized and resuspended in serum-free medium. The final concentration was adjusted to $5\times10^7$ cells/ml and the cell suspension was placed on ice. After the site was cleaned with ethanol, 0.1 ml ($5\times10^6$ cells) of the suspension was subcutaneously injected into the flanks of nude mice. Tumors were measured with a dial-caliper, and volumes were determined using the formula: 0.5×(larger diameter)×(smaller diameter)$^2$. When the primary tumors were 40-75 mm$^3$ in size, animals were randomly divided into two groups. One group (n=16) received intratumoral injection of 10 µg of the TT641 pAb as a suspension in 75 µl of PBS for 5 consecutive days (Days 0-4). As a control, the other group (n=15) received non-immunized rabbit IgG (DAKO). Tumor growth was assessed by calculation of a growth ratio based on tumor volume at the indicated day to that calculated at the initial day of treatment.

Figure 13:
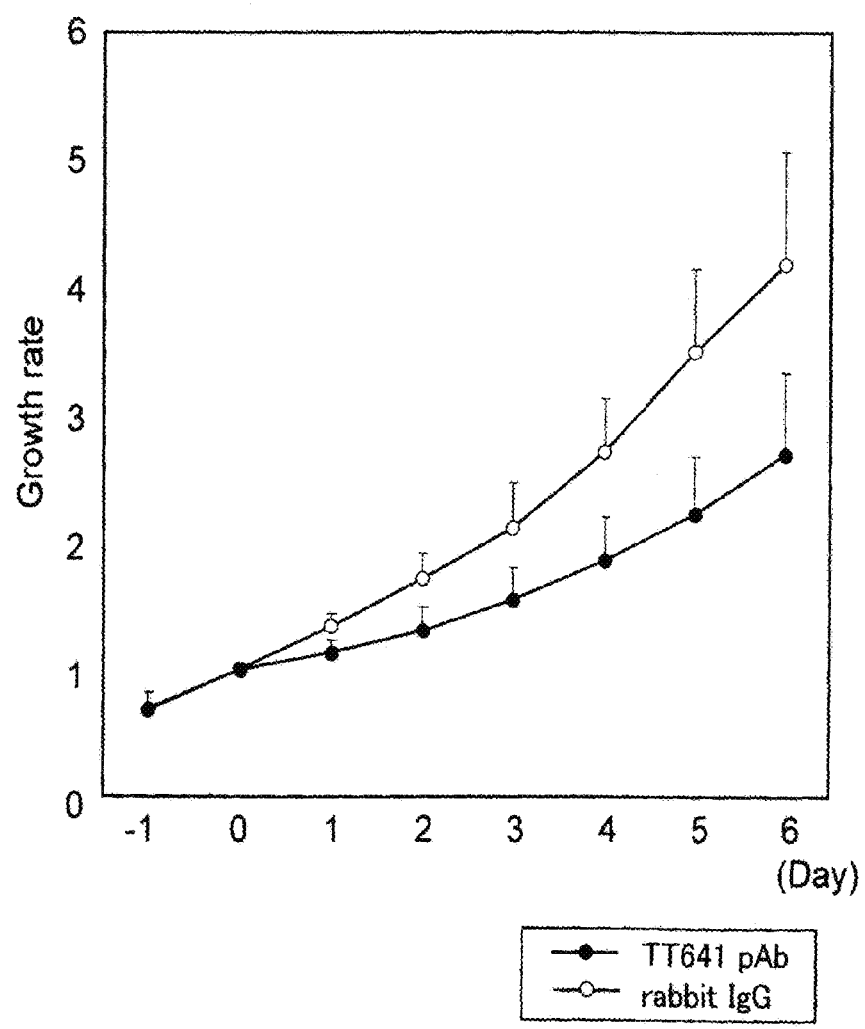
FIG. 13 shows that TT641 pAb exerted a growth inhibitory effect on SS xenografts. The tumor growth was assessed as the ratio of tumor volume at the indicated day to that calculated at the initial day of treatment in the experimental group (n=16) treated with TT641 pAb (closed circle) and in the control group (n=15) with non-immunized rabbit IgG (open circle). Treatment was continued for 5 consecutive days (Days 0-4). Data was expressed as mean±SD.

As shown in FIG. 13, the growth of SS xenografts was attenuated by treatment with TT641 pAb, as compared with treatment with non-immunized rabbit IgG. At day 6 after the initiation of antibody injection, the growth rate of SS xenografts in mice treated with TT641 pAb was significantly lower than that observed in negative controls (P=$1.71\times10^{-5}$; Student's t-test).

To elucidate the reason of growth attenuation by treatment with TT641, The present inventors performed the TUNEL analysis.

Mice were sacrificed at the indicated time, and the tumors were collected and fixed with 10% formaldehyde. For the in situ terminal transferase-mediated dUTP nick end-labeling (TUNEL) assay, one of the serial sections of paraffin-embedded specimens was stained using ApopTag Apoptosis Detection Kit (Intergen) according to the manufacturer's instructions. In addition, to assess cell proliferation ability, immunohistochemical staining with anti-Ki-67 mouse monoclonal antibody (MIB-1, DAKO) was carried out in the same manner as mentioned in the immunohistochemical staining section.

Figure 14:
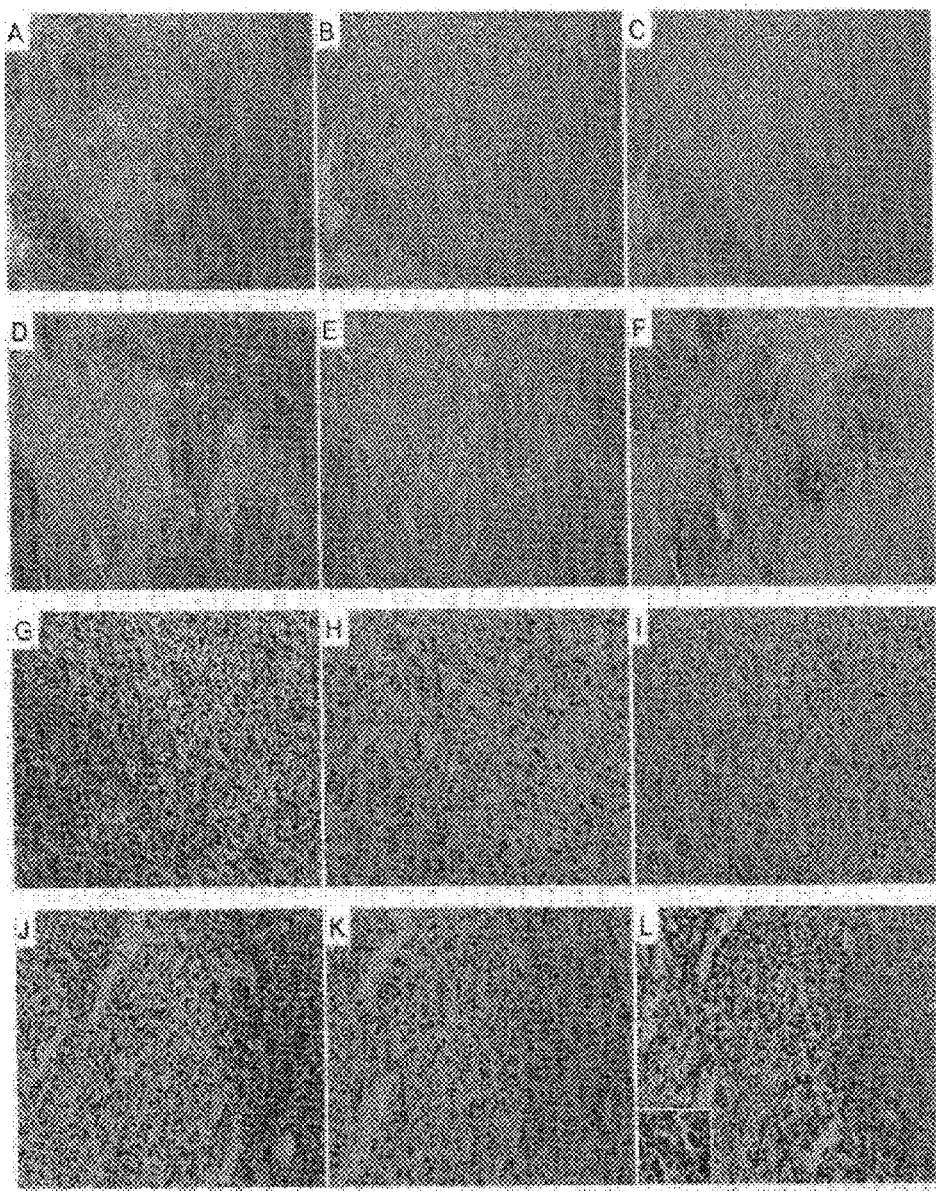
FIGS. 14A to 14L are photographs showing TUNEL analysis and immuno-histochemical staining for Ki-67. At 2 days after the completion of treatment, tumors were extirpated and fixed in 10% formaldehyde. TUNEL analysis and immunohistochemical staining for Ki-67, a reliable indicator of cell proliferation ability, were performed on the serial sections of paraffin-embedded specimens from tumors treated with non-immunized rabbit antibody (A, B, C, G, H and I) and TT641 pAb (D, E, F, J, K and L). In these figures, A, D, G and J=HE staining; B, E, H and K=immunostaining for Ki-67, and C, F, I and L=TUNEL analysis. The original magnification of A-F=×40; G-L=×200; inset in L=×400.

The specimen of tumor tissues treated with TT641 pAb showed clusters of apoptotic cells (FIGS. 14F and 14L), which were negative for staining for a marker of cell proliferation, Ki-67 (FIGS. 14E and 14K), whereas apoptotic cells were sparse in tumor specimens of negative controls (FIGS. 14C and 14I). Since the apoptotic cells in the tumor tissue were surrounded by many viable tumor cells, which were positive for Ki-67 staining (FIGS. 14E and 14K), the growth inhibitory effect of TT641 pAb on SS xenografts was thought to be insufficient to regress the tumors drastically.

Example 13

Expression of Mouse FZD10 in Normal Mouse Tissues

Figure 15:
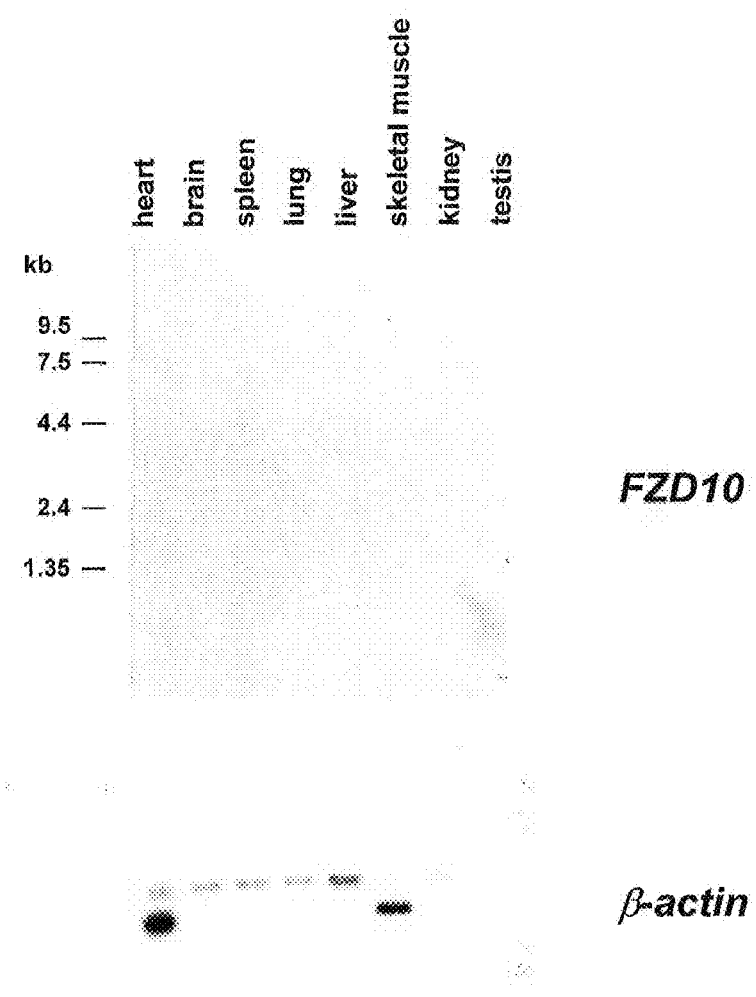
FIG. 15A is a photograph showing expression of mouse FZD10 in normal mouse tissues detected by northern blot analysis of FZD10 in eight normal mouse tissues (heart, brain, spleen, lung, liver skeletal muscle, kidney or testis). Expression of β-actin was used as a loading control.
FIGS. 15B to 15E are photographs showing immunocytochemical staining in normal mouse kidney (B), placenta (C), lung (D), and brain (E) tissues using the TT641 pAb.
Figure 15:
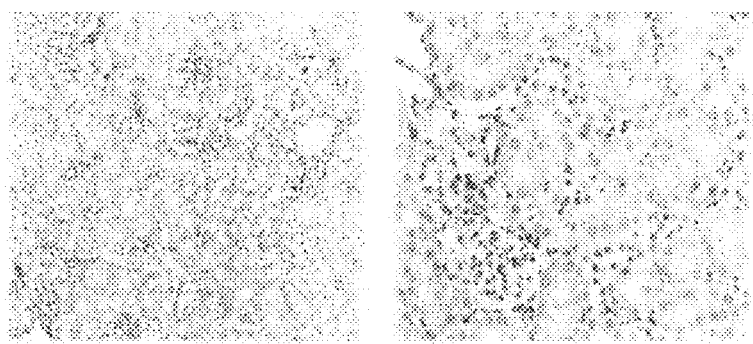
Figure 15:
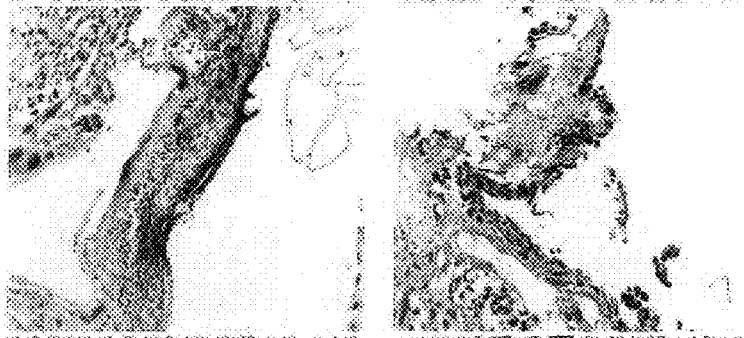
Figure 15:
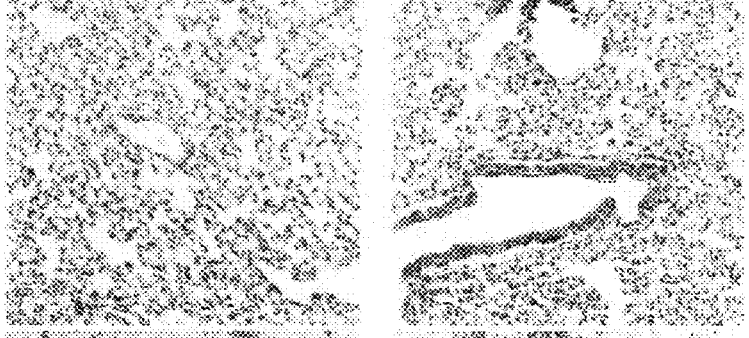
Figure 15:
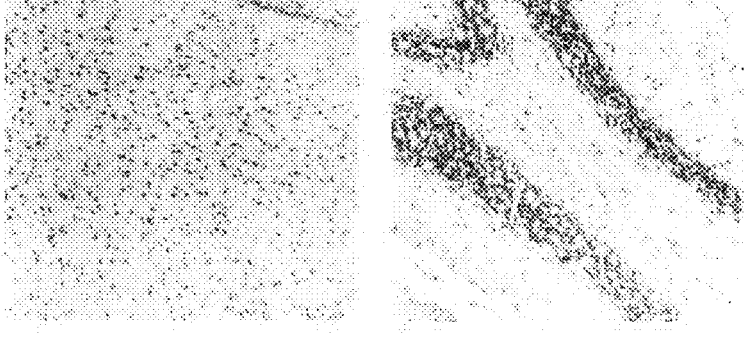

Since it was revealed that an amino-acid identity between human and mouse FZD10 was approximately 93%, we investigated whether TT641 pAb could also cross-react with mouse FZD10 protein using normal mouse tissues by Northern blot and immunohistochemical analyses. Although Northern-blot analysis revealed that no band was detected in normal mouse heart, brain, spleen, lung, liver skeletal muscle, kidney or testis tissues (FIG. 15A), immunohistochemical analysis showed that positive staining was observed in mouse kidney (FIG. 15B), and placenta (FIG. 15C), as well as in normal human tissues, and weak immunoreactivity was observed in normal mouse lung (FIG. 15D), but not observed in brain (FIG. 15E).

Example 14

Generation of Monoclonal Antibodies (mAbs)

Monoclonal anti-FZD10 antibodies (mAbs 1F2, 1F4, 5F2, 5H4 and 6C9) were obtained in the following:

A purified FZD10-ECD (residues 1-225 of the amino acid sequence shown in SEQ ID NO: 153) recombinant protein (Medical & Biological Laboratories, Nagoya, Japan) was used to immunize three 6-week BALB/c mice. 100 µg of the antigen (FZD10-ECD recombinant protein) emulsified in Freund's complete adjuvant was injected into the both foot pads of each mouse, followed by three times intraperitoneal injections at 3 days intervals. Two days after one booster inoculation of 100 µg of in 150 µl of Freund's complete adjuvant, cell fusion and cloning by limiting dilution were performed as follows. Total of six lymph nodes from selected mouse were fused with P3-U1 myeloma cells and hybridomas selected with HAT (15% FCS/RPM/HAT/BM-condimedH1) medium. After about 2-weeks from the fusion, the supernatants of the cells were screened by ELISA assay using recombinant FZD10-ECD as antigen. 42 positive hybridomas (OD450 in ELISA>0.1) were cloned twice by limiting dilution, and further selected by flow cytometry analysis using SS cell line, YaFuSS. Eventually, five single clones were selected as monoclonal antibody-producing hybridoma. Heavy chain isotype of each clone was identified by ELISA and monoclonal antibody concentration was determined by immunodiffusion. To produce large quantities of mAbs, $5\times10^5$ cloned hybridoma cells were administered into ascites fluid in BALB/c mice. After 10 days to 2-weeks after administration, ascites fluid were collected and pooled.

The hybridoma clone Mouse-Mouse hybridoma 5F2 TK10P2 producing the monoclonal antibody raised against the recombinant FZD10 protein was deposited internationally at the IPOD International Patent Organism Depositary of the National Institute of Advanced Industrial Science and Technology (AIST Tsukuba Central 6, 1-1, Higashi 1-chome, Tsukuba-shi, Ibaraki-Ken, 305-8566 Japan) as of Feb. 18, 2004 under the accession number of FERM BP-08628.

Example 15

Specificity of Monoclonal Anti-FZD10 Antibodies (mAbs)

(1) Specificity to FZD10 Protein

Figure 16A:
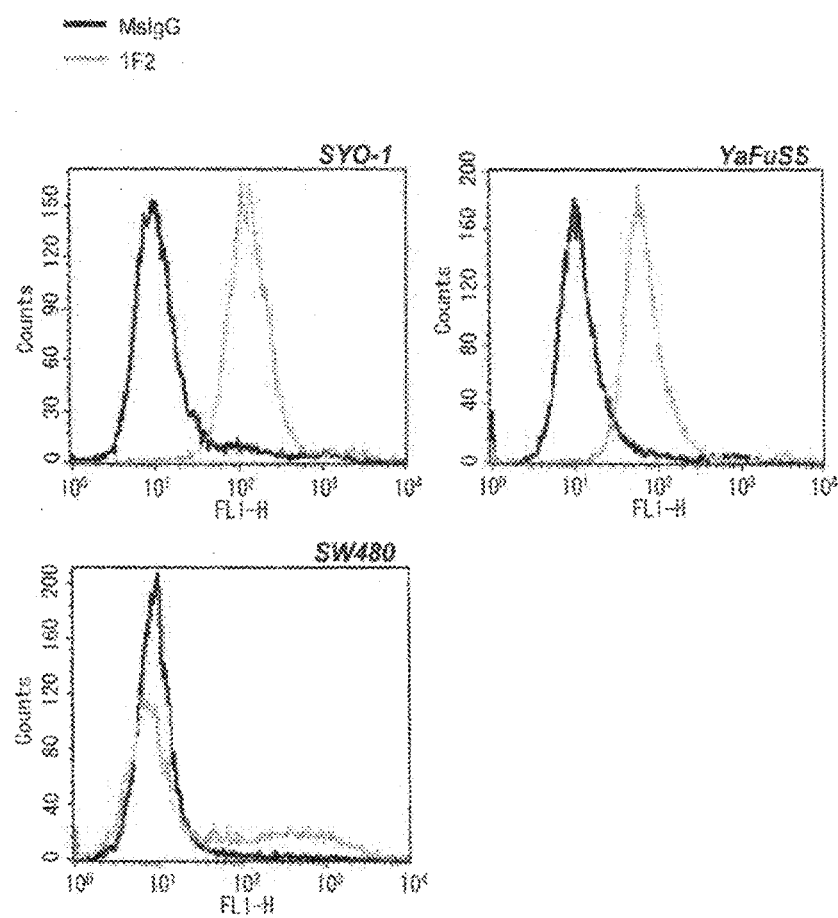
FIGS. 16A to 16E are graphs showing flow-cytometric analysis using anti-FZD10 mAbs, 1F2 (A), 1F4 (B), 5F2 (C), 5H4 (D) and 6C9 (E), in SS lines (SYO-1 and YaFuSS; upper panels) and colon-cancer cell lines (SW480 and HT29; lower panels). Gray lines show expression of the cell-surface antigen FZD10 detected by each mAb; black lines depict the fluorescent signals of cells incubated with non-immunized rabbit IgG as a negative control.
Figure 16B:
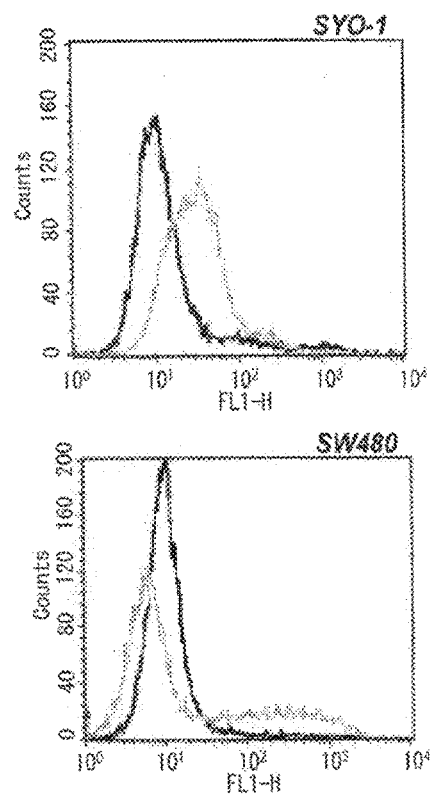
Figure 16C:
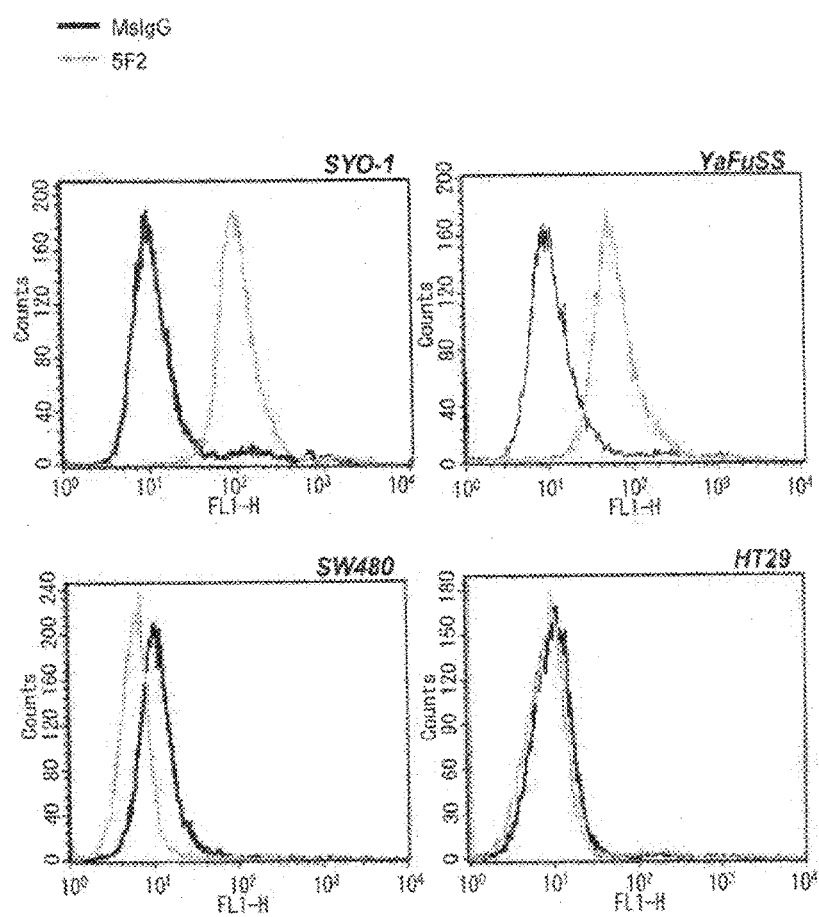
Figure 16D:
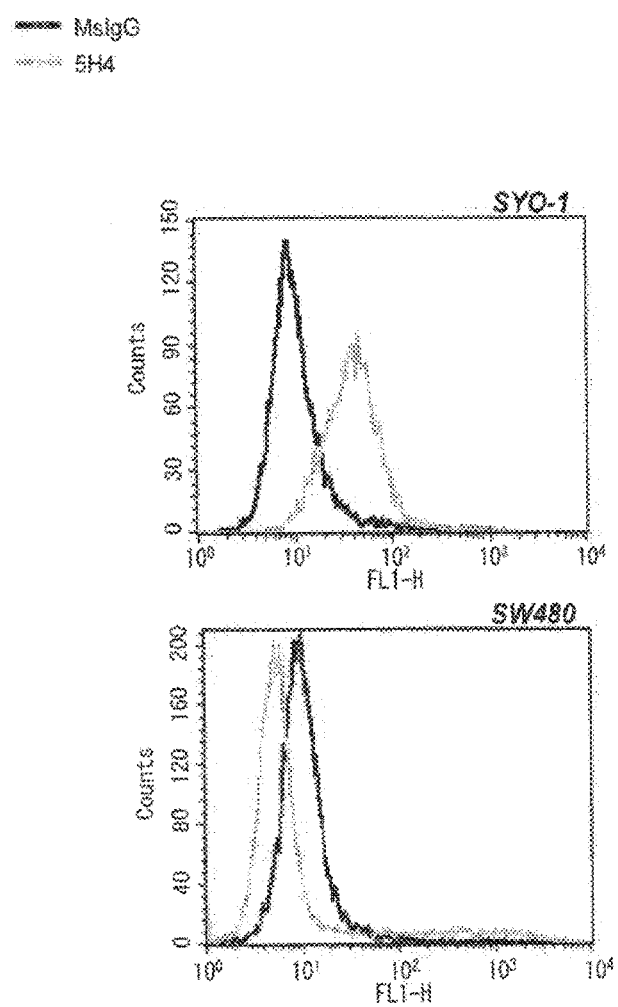
Figure 16E:
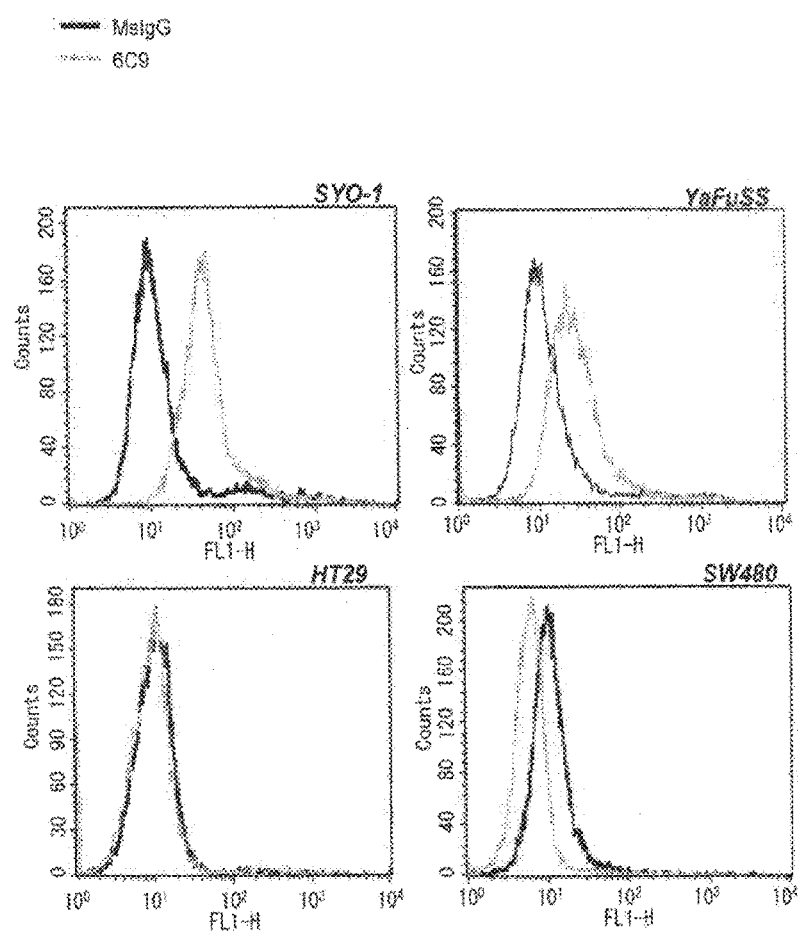

We first examined the specificity of the mAbs obtained in Example 10 by flow cytometry analysis using SS cell lines (SYO-1 and YaFuSS) which showed high expression of FZD10 transcript, and colon-cancer cell lines (SW480 and HT29) which showed hardly detectable expression. All of these mAbs could specifically recognize the FZD10 protein as surface antigen in SYO-1 or YaFuSS, whereas no fluorescent signals were detected in SW480 or HT29 (FIGS. 16A (1F2), 16B(1F4), 16C(5F2), 16D(5H4), 16E(6C9)). These results are consistent with those obtained by using TT641 pAb as described in Example 8. Taken together, these results indicate that the anti-FZD10 mAbs also specifically recognize the extracellular domain of FZD10 under native condition.

(2) Epitope Mapping

To further characterize the specificity of each mAb, we performed epitope mapping in the same manner as in Example 9.

A series of 10-residue linear synthetic peptides overlapping by one amino acid and covering the entire FZD10-ECD was covalently bound to a cellulose membrane (SPOTs; Sigma Genosys, Woodlands, Tex.) as described in Example 9. The membrane containing 216 peptide spots was hybridized with anti-FZD10 mAbs (1F2, 5F2, 5H4 and 6C9) at 4° C. overnight. After incubation with anti-rabbit HRP-conjugated IgG (Amersham Bioscience, Piscataway, N.J.), the spots were visualized with 3-amino-9-ethylcarbazole.

As a result, mAbs 1F2, 5F2, 5H4 and 6C9 recognized the amino acid residues 157-170 (EPTRGSGLFPPLFR, SEQ ID NO: 219), 157-170 (EPTRGSGLFPPLFR, SEQ ID NO: 219), 161-173 (GSGLFPPLFRPQR, SEQ ID NO: 220), 156-169 (DEPTRGSGLFPPLF, SEQ ID NO: 221) in FZD10-ECD (residues 1-225 of the amino acid sequence shown in SEQ ID NO:153), respectively (FIG. 17).

Example 16

Inhibition of Growth of SS Xenografts by 5F2 mAb

In vivo experiments were performed in our animal facility in accordance with institutional guidelines as well. A 0.1 ml of SYO-1 cell suspension ($5\times10^6$ cells) was injected subcutaneously into the flanks of six-week-old athymic female mice (BALB/cA Jcl-nu). Tumor volumes were determined using the formula: 0.5×(larger diameter)×(smaller diameter). When the xenografts were 40-75 mm³ in size, animals were randomly divided into two groups. One group received intratumoral injection of 50 µg of the mAbs, 5F2 (n=5), for 10 consecutive days, respectively. As a control, the other group (n=6) received non-immunized rabbit IgG (DAKO). Tumor growth was assessed by calculating the ratio of tumor volume on the indicated day to the volume calculated on the initiation of treatment.

Figure 18:
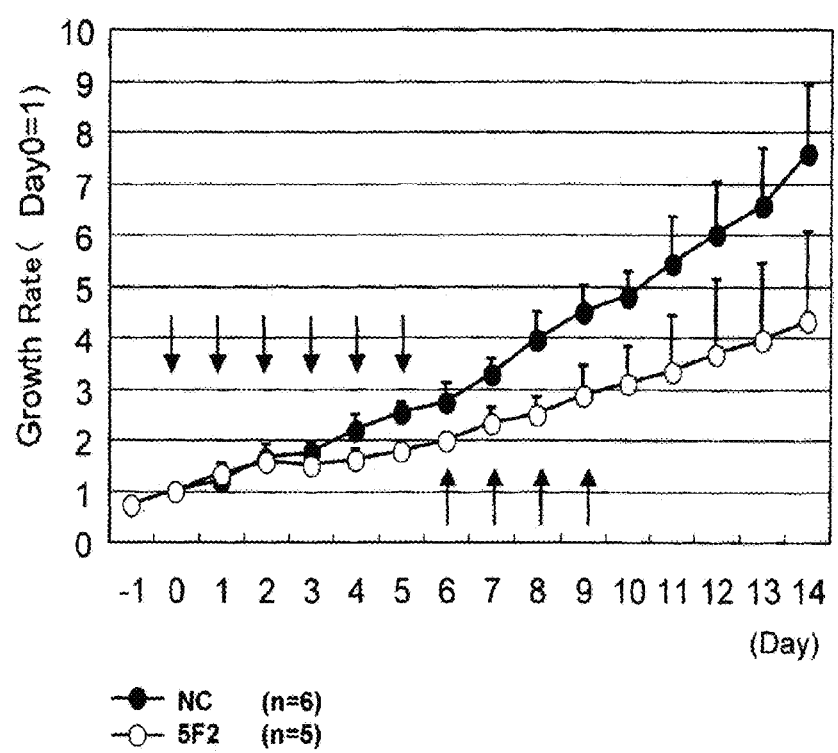
FIG. 18 is a graph showing growth-inhibitory effect of mAb 5F2 on SS xenografts. Tumor growth was assessed as the ratio of tumor volume at the indicated day to that calculated on the initial day of treatment in the experimental group (5F2, n=5) treated with mAbs (5F2, open circles) and in the control group (n=6) given non-immunized rabbit IgG (closed circles). Treatment was continued for ten consecutive days (Days 0-9; arrows). Data are expressed as means±SD.

To confirm the growth inhibition effect of TT641 pAb in SS xenografts, we examined whether the anti-FZD10 mAbs, 5F2 and 1F2 show antitumor effect in SS xenografts. The growth of SS xenografts was attenuated by treatment with mAb 5F2, as compared to treatment with non-immunized rabbit IgG (FIG. 18). At day 10 after initiation of antibody treatment (as indicated by the arrows in FIG. 18), the growth rate of SS xenografts in mice treated with mAbs 5F2 was significantly lower than that observed in negative controls (FIG. 18). These findings indicated that mAb 5F2 is likely to inhibit the tumor growth of SS cells.

Example 17

Construction of siRNA Expression Vector

To investigate the cellular function of FZD10, we constructed plasmids expressing siRNAs specific to FZD10 under the control of the U6 promotor (psiU6BX-FZD10). Two siRNAs (psiU6BX-FZD10A, B and C) were constructed according to FZD10 ORF sequence.

(1) Construction of siRNA Expression Vector, psiU6X3.0

Since snRNA U6 gene was reported to be transcribed by RNA polymerase III, which produces the short transcripts with uridines at the 3' end, we amplified the genomic fragment of snRNA U6 gene containing its promoter region by PCR using a set of primers, 5'-GGGGATCAGCGTTTGAG-TAA-3' (SEQ ID No. 181), and 5'-TAGGCCC CACCTCCT-TCTAT-3' (SEQ ID No. 182) and human placental DNA as a template. The product was purified and cloned into pCR plasmid vector using a TA cloning kit according to the supplier's protocol (Invitrogen). The BamHI, XhoI digested fragment containing the snRNA U6 gene was purified and cloned into nucleotide 1257 to 56 fragment of pcDNA3.1(+) plasmid, which was amplified by PCR with a set of primer, 5'-TGCGGATCCAGAGCAGATTGTACTGAGAGT-3' (SEQ ID No. 183) and 5'-CTCTATCTC GAGTGAGGCG-GAAAGAACCA-3' (SEQ ID No. 184). The ligated DNA was used as a template for PCR with primers, 5'-TTT AAGCTTGAAGACTATTTTTACATCAGGTTGTTT TTCT-3' (SEQ ID No. 185) and 5'-TTT AAGCTTGAAGACACGGTGTTTCGTCCTTTCCACA-3' (SEQ ID No. 186) (underlines indicate HindIII site). The product was digested with HindIII, which was subsequently self-ligated to produce psiU6BX3.0 vector plasmid.

(2) Plasmids Construction

To construct the myc/His-tagged full-length FZD10 expression vectors, we firstly PCR-amplified the entire coding sequence of the FZD10 (SEQ ID No. 154) using a human placenta cDNA library as template with following primers:

```
                                            (SEQ ID No. 187)
5'-CCGGAATTCCAGACCGTGCATCATGCAGCGCCCGGGCCCCGCCT-3'
(underline indicates EcoRI site)
and (SEQ ID No. 188)
5'-AAAAAGCTTCACGCAGGTGGGCGACTG-3'
(underline indicates HindIII site).
```

After digestion of EcoRI and HindIII, PCR product was cloned into to pcDNA3.1-myc/His vector (Invitrogen), and then the inserted FZD10 cDNA with myc/His-tag was further subcloned into pCAGGS/neo expression vector. Next, an internal-tagged HA-FLAG-FZD10FL (residue 1-581; SEQ ID No. 153), expression plasmid constructs were generated from the cloned full-length FZD10 cDNA by PCR amplification with following primer combinations:

```
FZD10-ATG,
                                            (SEQ ID No. 189)
5'-AAGTCGACACCATGCAGCGCCCGGGCCCC-3'
(underline indicates SalI site)
and FZD10-nt651,
                                            (SEQ ID No. 190)
5'-TCTCGAGGACATCCACGCCGGGCGTG-3'
(underline indicates XhoI site)

for N-terminal portion of FZD10 (1-217 amino-
acids of SEQ ID No. 153);

FZD10-nt652,
                                            (SEQ ID No. 191)
5'-AAGTCGACTACTGGAGCCGCGAGGACAAG-3'
(underline indicates SalI site)
and FZD10-TGA,
                                            (SEQ ID No. 192)
5'-AACTCGAGTCACACGCAGGTGGGCGACT-3'
(underline indicates XhoI site)

for C-terminal portion of FZD10 (218-581 amino-
acids of SEQ ID No. 153).
```

The N-terminal portion (residues 1-217) of FZD10ΔC1 (residues 1-578) and FZD10ΔC2 (residues 1-525) expression plasmid constructs were generated and C-terminal portion (residues 218-each end) of each construct was generated by the forward primer (FZD10-nt652) and the following reverse primers, respectively;

```
FZD10ΔC1(1-578),
                                            (SEQ ID No. 193)
5'-AACTCGAGTCAGGGCGACTGGGCAGGGATCT-3'
(underline indicates XhoI site)
and FZD10ΔC2(1-525),
                                            (SEQ ID No. 194)
5'-AACTCGAGTCAGGAGGTCCAAATCCACATCCC-3'
(the underline indicates XhoI site).
```

Plasmids expressing siRNAs specific to FZD10 were prepared by cloning the double-stranded oligonucleotides into psiU6BX3.0 vector (Table 6). The target sequences for siRNA in each plasmid are shown in Table 7. The complementary oligonucleotides were each phosphorylated by incubation with T4-polynucleotide kinase at 37° C. for 30 min, followed by boiling and cooling down to room temperature slowly to anneal the two oligonucleotides. Each product was ligated into psiU6BX3.0 to construct an FZD10-siRNA expression vector.

TABLE 6

Sequences of specific double-stranded oligonucleotides inserted into siRNA expression vector

| | Seq ID No. |
|---|---|
| psi-U6BX-FZD10-B | |
| 5'-CACCAACGCTGGACTGCCTGATGTTCAAGAGACATCAGGCAGTCCAGCGTT-3' | 195 |
| 5'-AAAAAACGCTGGACTGCCTGATGTCTCTTGAACATCAGGCAGTCCAGCGTT-3' | 196 |

TABLE 6-continued

Sequences of specific double-stranded oligonucleotides
inserted into siRNA expression vector

| | Seq ID No. |
|---|---|
| psi-U6BX-FZD10-C | |
| 5'-CACCGACTCTGCAGTCCTGGCAGTTCAAGAGACTGCCAGGACTGCAGAGTC-3' | 197 |
| 5'-AAAAGACTCTGCAGTCCTGGCAGTCTCTTGAACTGCCAGGACTGCAGAGTC-3' | 198 |
| psi-U6BX-EGFP | |
| 5'-CACCGAAGCAGCACGACTTCTTCTTCAAGAGAGAAGAAGTCGTGCTGCTTC-3' | 199 |
| 5'-AAAAGAAGCAGCACGACTTCTTCTCTCTTGAAGAAGAAGTCGTGCTGCTTC-3' | 200 |
| psi-U6BX-Luc | |
| 5'-CACCGTGCGCTGCTGGTGCCAACTCTCTTGAAGTTGGCACCAGCAGCGCAC-3' | 201 |
| 5'-AAAAGTGCGCTGCTGGTGCCAACTTCAAGAGAGTTGGCACCAGCAGCGCAC-3' | 202 |

The specific sequences to FZD10 are underlined.

TABLE 7

Target sequences for siRNA

| | Seq ID No. |
|---|---|
| psi-U6BX-FZD10-B | |
| 5'-AACGCTGGACTGCCTGATG-3' | 203 |
| psi-U6BX-FZD10-C | |
| 5'-GACTCTGCAGTCCTGGCAG-3' | 204 |
| psi-U6BX-EGFP | |
| 5'-GAAGCAGCACGACTTCTTC-3' | 205 |
| psi-U6BX-Luc | |
| 5'-GTGCGCTGCTGGTGCCAAC-3' | 206 |

Example 18

Effect of FZD10-siRNAs on Growth of Synovial Sarcoma Cell Lines

We transfected the plasmids prepared in Example 17 into synovial sarcoma cell line, SYO-1, and examined the expression level of FZD10 by semi-quantitative RT-PCR. Also, we conducted cell growth assay to confirm the cell growth inhibition.

(1) Semi-Quantitative RT-PCR

SYO-1 cells were maintained in Dulbecco's modified Eagle's medium supplemented with 10% fetal bovine serum and antibiotics. Cell line Nucleofector™ kit V (Amaxa Biosystems, Cologne, Germany) was used for transfection of SYO-1 cells. The transfected cells were assayed 48-72 h after transfection.

Total RNA was extracted from transfected cell using TRIZOL reagent (Invitrogen) according to manufacturer's protocol. Extracted RNA was treated with DNAse I (Roche Diagnostics, Mannheim, Germany) and reverse-transcribed to single-stranded cDNAs using oligo(dT)$_{12-18}$ primer with Superscript II reverse transcriptase (Invitrogen). PCR amplification was performed using the cDNAs as templates and primers as follows:

(SEQ ID No. 207)
5'-TATCGGGCTCTTCTCTGTGC-3'
and
(SEQ ID No. 208)
5'-GACTGGGCAGGGATCTCATA-3'
for FZD10, (SEQ ID No. 209)
5'-CTGCACGCTGGTCTTCCTCT-3'
and
(SEQ ID No. 210)
5'-CCGATCTTGACCATGAGCTTC-3'
for FZD9, (SEQ ID No. 211)
5'-TTAGCTGTGCTCGCGCTACT-3'
and
(SEQ ID No. 212)
5'-TCACATGGTTCACACGGCAG-3'
for β2MG.

Figure 19:
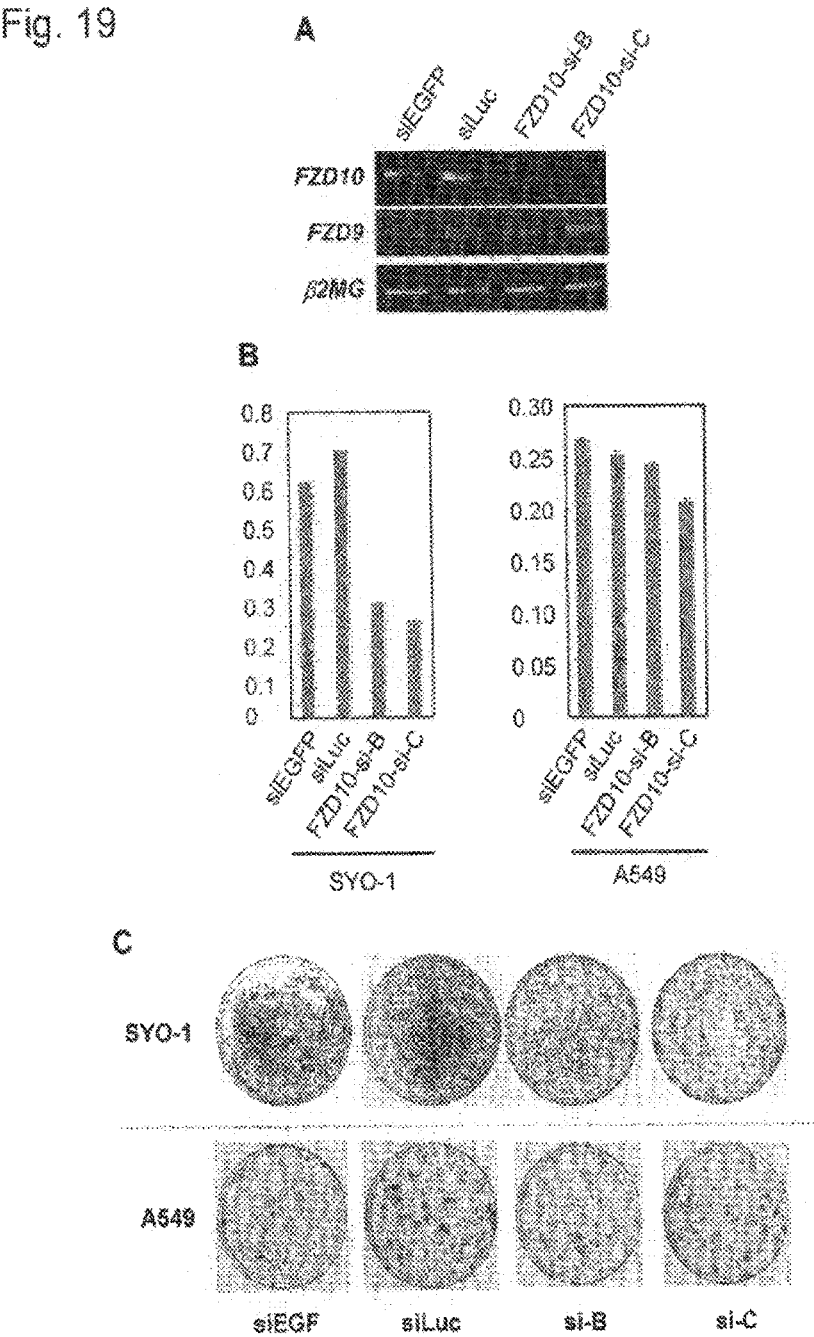
FIGS. 19A to 19C show growth-inhibitory effects of small-interfering RNAs (siRNAs) designed to reduce expression of FZD10 in SS cell line, SYO-1. (A) Semi-quantitative RT-PCR showing suppression of endogenous expression of FZD10 in SYO-1 cell. β2MG was used as an internal control. Expression of FZD9 is not affected by these siRNAs. (B) MTT Assay of SYO-1 cells transfected with psiU6BX3.0 vectors. A549 cell, in which undetectable FZD10 expression is observed, is an "off-target" control shows no growth-effect with these siRNAs. (C) Colony-formation assay demonstrating a decrease in the numbers of colonies by knock-down of FZD10 expression in SYO-1 cell. A549 cell line is an "off-target" control.

As a result, the two siRNA constructs, FZD10 (si-B and -C)-specific siRNAs significantly suppressed expression, compared with control (psiU6BX-LUC or -SC), while expression of FZD9, which has the highest similarity to FZD10 among Frizzled family genes, was not affected by these siRNAs (FIG. 19A).

(2) Cell Growth Assays

To confirm the cell growth inhibition with FZD10-specific siRNAs, we performed colony-formation and MTT assays, respectively. SYO-1 cells were transfected as described in (1) above. Lung cancer cell line, A549 cells were maintained in RPMI1640 medium supplemented with 10% fetal bovine serum and antibiotics. FuGene6 (Roche) was used for transfection of A549 cells.

SYO-1 and A549 cells transfected with psiU6-FZD10, psiU6-luc or psiU6-EGFP plasmids were maintained in media containing appropriate concentrations of Geneticin for 13 days. The cells were fixed with 4% paraformaldehyde and stained with Giemsa solution. Additionally, cell viability was measured by MTT assay using Cell-counting kit8 (Dojindo) as described (Shimokawa T et al. (2003). *Cancer Res*, 63, 6116-20).

As a result, introduction of FZD10 siRNA constructs suppressed growth of SYO-1, consisting with the result of above reduced expression of this gene (FIGS. 19B and 19C). Furthermore, the growth of A549 cell which shows undetectable expression of FZD10 was not affected, indicating that no "off-target" effect occurred by these siRNAs. Each result was verified by three independent experiments. Thus, our findings suggest that FZD10 has a significant function in the cell growth of the synovial sarcoma.

While the invention has been described in detail with reference to certain preferred embodiments, it is appreciated that many variations and modifications may be made by to those skilled in the art within the spirit and scope of the present invention as defined in the appended claims.

The invention claimed is:

1. A method for treating synovial sarcoma that overexpresses Frizzled homologue 10 (FZD10) in a subject, comprising administering to the subject an effective amount of an antibody or antigen binding fragment thereof that specifically recognizes at least residues 43-56, 61-72, 156-169, 157-170, 157-172, 161-173, 174-191, 189-202, or 214-225, of the amino acid sequence shown in SEQ ID NO: 153.

2. The method of claim 1, wherein the antibody is polyclonal or monoclonal antibody.

3. A method for treating synovial sarcoma that overexpresses Frizzled homologue 10 (FZD10) in a subject, comprising administering to the subject 3-15 μg per kg body weight of the subject of an antibody or antigen binding fragment thereof against the extracellular domain of FZD10 protein (SEQ ID NO: 153), once a day, one to five times during a period of 5 to 10 days.

* * * * *

SEQUENCE LISTING

```
<160> NUMBER OF SEQ ID NOS: 221

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 1
tcagaaaccc ttcagtgcta cat                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
atacacacgc agaaaccact ctt                                            23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
ccactgtctc atgaagtgtc aaa                                            23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
acagaatggt aagaaaggaa gcc                                            23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
gacacagatc atagctctac agga                                           24

<210> SEQ ID NO 6
```

```
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
gagtatttga gcaattgatg gg                                          22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7
gtgaggaagc aagtgacaag g                                           21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
caccctacct tctctcaaat gc                                          22

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
gagagcgcaa tacctcacg                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
gtggagaaac agggaggtga                                             20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
aagacagcag cagttgctaa aga                                         23

<210> SEQ ID NO 12
<211> LENGTH: 23
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
gaagaaacag gctaggaaaa agg                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
ggggatcagt tctacatcaa gac                                              23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
cgtctaacca gtttaatgac ttcg                                             24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
catgagaaga agtgtcccgt tt                                               22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
taaaactact gaggtgacgg cat                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
ccaacatcac ttctgtgatg aga                                              23

<210> SEQ ID NO 18
<211> LENGTH: 23
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 18
gatttgagtg atcattaggg ctg                                              23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
caaccttaag cttctacggg att                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
cctcaagtca acatctgcct atc                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
gaaggcgtgg tcactaaatg taa                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
ctttaatttc agagggcgaa gac                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
acttgcctgt gtttacactt cct                                              23

<210> SEQ ID NO 24
<211> LENGTH: 23
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 24
gtgttggttt cctcattcaa gtc                                           23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
ctgttgaggt acttgctggg ac                                            22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 26
tcagatcatg tttattgtgg gg                                            22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
ccaaagaaac tcagaagagt cc                                            22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
gaaagtgaac tccagtggaa ag                                            22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
ctgaaggcgg ctaacacaga c                                             21

<210> SEQ ID NO 30
<211> LENGTH: 22
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 30
tacacgattg tcctcaccct tc                                              22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 31
cactgcaata aaaggtacga agc                                             23

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 32
ttcagaaaac taaagcagca cc                                              22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
ctctggcatc ttggtaagga g                                               21

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 34
cctcatgttc tttatttgca cagag                                           25

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 35
gtgaactgag gaaggtgctt aga                                             23

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 36
ctttattctt gagatgcagg gg                                           22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 37
cccagatgac cacatttaat acc                                          23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 38
agagaaggga atcacaacac aga                                          23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 39
caaggctaga aagatgctac gtt                                          23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 40
cagacacgca cttgtggttt att                                          23

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 41
agaagatgcc aatgtttcat cc                                           22

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 42
gactgtgttg agtaagagcc aca                                            23

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 43
atgctgtctc cagacccact                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 44
agtgaccctg gctctgaaag                                                20

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 45
ggcttattct tcaggcacta agg                                            23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 46
agcagttgga aatgtacttg cac                                            23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 47
ctcctttcca gacagatgag aga                                            23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide
```

```
<400> SEQUENCE: 48
atgcctgttt ttcctacact cag                                            23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 49
ttactgtttt gtctcttgag ccc                                            23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 50 gttacccta ggtatgcttc gtt                                             23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 51
aaaaggatag ttccaggcca tag                                            23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 52
gccagtagac ccaaacaata aga                                            23

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 53
cgatgagctg ggagtgaagc                                                20

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 54
```

```
tttcgttctg ttttctcatg acaga                                          25
```

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 55

```
ggattgcagc ttctgggaac                                                20
```

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 56

```
ttcgagaagc gccacaaga                                                 19
```

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 57

```
agccctcgcg gcaag                                                     15
```

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 58

```
ttgaaatgct ttgatattct aattgaca                                       28
```

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 59

```
tgacggactt cgtgtgcaaa                                                20
```

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 60
acgcagacag aaggtggagc                                              20

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 61
gacaaatgtt cgtcctgtta atttatagg                                    29

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 62
gaggagatcc ggcgcataa                                               19

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 63
ctctttgcac atgggcatca                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 64
ctggcctgcc ttcgttaact                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 65
catcgctctt ggattcccac                                              20

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 66
gagagagtca gactaataaa caggctgtt                                    29

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 67
caagcagttt ggaggcagc                                                    19

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 68
gctgagaggc cggcact                                                      17

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 69
gctggctcaa catggaagga                                                   20

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 70
attcttacga actttaaaaa aatagcaaag t                                      31

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 71
attcacgccg aagaagttgg                                                   20

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 72
gagacatgca gccgtttcg                                                    19

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 73
ttttgccact gtgtatatca tcca                                            24

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 74
agcactcgct ggaacatgaa                                                 20

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 75
tctttgtaag gctgtacctt gcat                                            24

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 76
gggcaggata cccaaacaaa                                                 20

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 77
caggcaaaag tgagcgcagc tcct                                            24

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 78
cccttccccc acccctaagt gcctaa                                          26

```
<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 79
atctatgagc ttcgaaataa ggaacgcatc tctg                              34

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 80
cacctgtccc cctgcttcag gga                                          23

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 81
ccctcactct ctcgcctgtt ctgtgtc                                      27

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 82
aacaagtttt ttccctgctc cccaaataga at                                32

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 83
cagcagagtg agctgttgac tcgatcg                                      27

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 84
agacggccag cagtcacaga cacaaagt                                     28

<210> SEQ ID NO 85
```

```
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 85
tgtggaggta gttgggtaga aaaattatta gaacattcac                              40

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 86
taccagcagc aatatggacg gagcctt                                            27

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 87
tctgtagaat ttgacggaac acagctattt ccc                                     33

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 88
tgtcaataaa cagcttcatg cctttgtaag ttatttcttg                              40

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 89
tcgttccatt ttgaagcg                                                      18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 90
caaacgcctt cgttccat                                                      18

<210> SEQ ID NO 91
<211> LENGTH: 18
```

```
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 91
cattttgaag cgacttag                                                18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 92
aatacagacc tgttgaca                                                18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 93
gcttggattt ctaggtct                                                18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 94
gcgaagtttt accttgct                                                18

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 95
taccttgctt ccgcaaac                                                18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 96
gattcagcga agttttac                                                18

<210> SEQ ID NO 97
<211> LENGTH: 18
<212> TYPE: DNA
```

```
<213> ORGANISM: Artificial Sequence
<220> FEATURE:
<223> OTHER INFORMATION: Description of Artificial Sequence: synthetic
      oligonucleotide

<400> SEQUENCE: 97
acagttgtcc agacataa                                                    18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 98
tctggatctt taggttcg                                                    18

<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 99
ccatgacccc gccaag                                                      16

<210> SEQ ID NO 100
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 100
tgcctggctc ttcagc                                                      16

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 101
accaactccc ccaaagt                                                     17

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 102
tagctatact tattcata                                                    18

<210> SEQ ID NO 103
<211> LENGTH: 18
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 103
taaaagtgga gacgagga                                                       18

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 104
gaaccgcccc agtacc                                                         16

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 105
cgacttctcg gtccgt                                                         16

<210> SEQ ID NO 106
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 106
tgaaaccccc tcaacca                                                        17

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 107
atacttattc atatcgat                                                       18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 108
aggagcagag gtgaaaat                                                       18

<210> SEQ ID NO 109
<211> LENGTH: 18
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 109
atggttcgcc ggtgccaa                                                 18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 110
aaatagaaaa tcccgcat                                                 18

<210> SEQ ID NO 111
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 111
aaaatcccgc atggtt                                                   16

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 112
ggctcttacc ttcattcg                                                 18

<210> SEQ ID NO 113
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 113
ttctcttctg agttgt                                                   16

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 114
aaccgtggcc gcttggta                                                 18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 115
tacgccctaa aagataaa                                                    18

<210> SEQ ID NO 116
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 116
ttggtacgcc ctaaaa                                                      16

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 117
gcttacttcc attctcgg                                                    18

<210> SEQ ID NO 118
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 118
tgttgagtct tctctt                                                      16

<210> SEQ ID NO 119
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 119
tccatgggcg atcggct                                                     17

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 120
gaagtttccg aagctc                                                      16

<210> SEQ ID NO 121
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

```
<400> SEQUENCE: 121
cgatcggctc cctaca                                              16

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 122
aagaaaaagt aacagt                                              16

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 123
tcggctagcg ggtacct                                             17

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 124
ctcgaagcct ttgaag                                              16

<210> SEQ ID NO 125
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 125
acatccctcg gctagc                                              16

<210> SEQ ID NO 126
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 126
tgacaatgaa aaagaa                                              16

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide
```

<400> SEQUENCE: 127
cgcgcggccc ggccat                                                    16

<210> SEQ ID NO 128
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 128
ttctccgtca atgccgt                                                   17

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 129
accagcttct ccgtcaat                                                  18

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 130
gcctttgtct cctctg                                                    16

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 131
taccggcccg gcgcgc                                                    16

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 132
tgccgtaact gcctctt                                                   17

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 133

```
taactgcctc ttcgacca                                                18
```

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 134

```
gtctcctctg tttccg                                                  16
```

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 135

```
ggctccatga acctagat                                                18
```

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 136

```
catgaaccta gatcaggc                                                18
```

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 137

```
ctccatgaac ctagatca                                                18
```

<210> SEQ ID NO 138
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 138

```
tgcgcttacc tgcggc                                                  16
```

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 139

```
actaactttc tcattttc                                                   18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 140
tagatccaag tacctcgg                                                   18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 141
cggactagat ccaagtac                                                   18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 142
actagatcca agtacctc                                                   18

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 143
cggcgtccat tcgcgt                                                     16

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 144
cttttactct ttcaatca                                                   18

<210> SEQ ID NO 145
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 145
catgctgccc cagcga                                                     16
```

<210> SEQ ID NO 146
<211> LENGTH: 16
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 146
agcagcagca ccaaaa                                                      16

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 147
aaacaggccg agcagca                                                     17

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 148
agatcatgtt tattgtgg                                                    18

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 149
agcgaccccg tcgtac                                                      16

<210> SEQ ID NO 150
<211> LENGTH: 16
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 150
aaaaccacga cgacga                                                      16

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 151
acgacgagcc ggacaaa                                                     17

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 152
ggtgttattt gtactaga                                                   18

<210> SEQ ID NO 153
<211> LENGTH: 581
<212> TYPE: PRT
<213> ORGANISM: Homo sapiens

<400> SEQUENCE: 153

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
        35                  40                  45

Met Thr Arg Met Pro Asn Leu Met Gly His Glu Asn Gln Arg Glu Ala
    50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
    130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
    290                 295                 300

Glu Ser Thr Gly Cys Thr Leu Val Phe Leu Val Leu Tyr Tyr Phe Gly

```
                305                 310                 315                 320
Met Ala Ser Ser Leu Trp Trp Val Val Leu Thr Leu Thr Trp Phe Leu
                    325                 330                 335

Ala Ala Gly Lys Lys Trp Gly His Glu Ala Ile Glu Ala Asn Ser Ser
                340                 345                 350

Tyr Phe His Leu Ala Ala Trp Ala Ile Pro Ala Val Lys Thr Ile Leu
                355                 360                 365

Ile Leu Val Met Arg Arg Val Ala Gly Asp Glu Leu Thr Gly Val Cys
370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
                420                 425                 430

Asn Thr Asp Lys Leu Glu Lys Leu Met Val Arg Ile Gly Leu Phe Ser
                435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
                500                 505                 510

Val Val Gly Ile Thr Ser Gly Met Trp Ile Trp Thr Ser Lys Thr Leu
                515                 520                 525

Gln Ser Trp Gln Gln Val Cys Ser Arg Arg Leu Lys Lys Lys Ser Arg
                530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
                565                 570                 575

Ser Pro Thr Cys Val
                580

<210> SEQ ID NO 154
<211> LENGTH: 2811
<212> TYPE: DNA
<213> ORGANISM: Homo sapiens
<220> FEATURE:
<221> NAME/KEY: CDS
<222> LOCATION: (18)..(1763)

<400> SEQUENCE: 154
acacgtccaa cgccagc atg cag cgc ccg ggc ccc cgc ctg tgg ctg gtc         50
                Met Gln Arg Pro Gly Pro Arg Leu Trp Leu Val
                 1               5                  10 ctg cag gtg atg ggc tcg tgc gcc gcc atc agc tcc atg gac atg gag        98
Leu Gln Val Met Gly Ser Cys Ala Ala Ile Ser Ser Met Asp Met Glu
             15                  20                  25 cgc ccg ggc gac ggc aaa tgc cag ccc atc gag atc ccg atg tgc aag       146
Arg Pro Gly Asp Gly Lys Cys Gln Pro Ile Glu Ile Pro Met Cys Lys
         30                  35                  40 gac atc ggc tac aac atg act cgt atg ccc aac ctg atg ggc cac gag       194
Asp Ile Gly Tyr Asn Met Thr Arg Met Pro Asn Leu Met Gly His Glu
     45                  50                  55
```

-continued

| | |
|---|---|
| aac cag cgc gag gca gcc atc cag ttg cac gag ttc gcg ccg ctg gtg<br>Asn Gln Arg Glu Ala Ala Ile Gln Leu His Glu Phe Ala Pro Leu Val<br>60                      65                      70                  75 | 242 |
| gag tac ggc tgc cac ggc cac ctc cgc ttc ttc ctg tgc tcg ctg tac<br>Glu Tyr Gly Cys His Gly His Leu Arg Phe Phe Leu Cys Ser Leu Tyr<br>                      80                      85                  90 | 290 |
| gcg ccg atg tgc acc gag cag gtc tct acc ccc atc ccc gcc tgc cgg<br>Ala Pro Met Cys Thr Glu Gln Val Ser Thr Pro Ile Pro Ala Cys Arg<br>              95                      100                  105 | 338 |
| gtc atg tgc gag cag gcc cgg ctc aag tgc tcc ccg att atg gag cag<br>Val Met Cys Glu Gln Ala Arg Leu Lys Cys Ser Pro Ile Met Glu Gln<br>110                      115                      120 | 386 |
| ttc aac ttc aag tgg ccc gac tcc ctg gac tgc cgg aaa ctc ccc aac<br>Phe Asn Phe Lys Trp Pro Asp Ser Leu Asp Cys Arg Lys Leu Pro Asn<br>            125                      130                      135 | 434 |
| aag aac gac ccc aac tac ctg tgc atg gag gcg ccc aac aac ggc tcg<br>Lys Asn Asp Pro Asn Tyr Leu Cys Met Glu Ala Pro Asn Asn Gly Ser<br>140                      145                      150                  155 | 482 |
| gac gag ccc acc cgg ggc tcg ggc ctg ttc ccg ccg ctg ttc cgg ccg<br>Asp Glu Pro Thr Arg Gly Ser Gly Leu Phe Pro Pro Leu Phe Arg Pro<br>                      160                      165                  170 | 530 |
| cag cgg ccc cac agc gcg cag gag cac ccg ctg aag gac ggg ggc ccc<br>Gln Arg Pro His Ser Ala Gln Glu His Pro Leu Lys Asp Gly Gly Pro<br>175                      180                      185 | 578 |
| ggg cgc ggc ggc tgc gac aac ccg ggc aag ttc cac cac gtg gag aag<br>Gly Arg Gly Gly Cys Asp Asn Pro Gly Lys Phe His His Val Glu Lys<br>            190                      195                      200 | 626 |
| agc gcg tcg tgc gcg ccg ctc tgc acg ccc ggc gtg gac gtg tac tgg<br>Ser Ala Ser Cys Ala Pro Leu Cys Thr Pro Gly Val Asp Val Tyr Trp<br>205                      210                      215 | 674 |
| agc cgc gag gac aag cgc ttc gca gtg gtc tgg ctg gcc atc tgg gcg<br>Ser Arg Glu Asp Lys Arg Phe Ala Val Val Trp Leu Ala Ile Trp Ala<br>220                      225                      230                  235 | 722 |
| gtg ctg tgc ttc ttc tcc agc gcc ttc acc gtg ctc acc ttc ctc atc<br>Val Leu Cys Phe Phe Ser Ser Ala Phe Thr Val Leu Thr Phe Leu Ile<br>                      240                      245                  250 | 770 |
| gac ccg gcc cgc ttc cgc tac ccc gag cgc ccc atc atc ttc ctc tcc<br>Asp Pro Ala Arg Phe Arg Tyr Pro Glu Arg Pro Ile Ile Phe Leu Ser<br>255                      260                      265 | 818 |
| atg tgc tac tgc gtc tac tcc gtg ggc tac ctc atc cgc ctc ttc gcc<br>Met Cys Tyr Cys Val Tyr Ser Val Gly Tyr Leu Ile Arg Leu Phe Ala<br>            270                      275                      280 | 866 |
| ggc gcc gag agc atc gcc tgc gac cgg gac agc ggc cag ctc tat gtc<br>Gly Ala Glu Ser Ile Ala Cys Asp Arg Asp Ser Gly Gln Leu Tyr Val<br>285                      290                      295 | 914 |
| atc cag gag gga ctg gag agc acc ggc tgc acg ctg gtc ttc ctg gtc<br>Ile Gln Glu Gly Leu Glu Ser Thr Gly Cys Thr Leu Val Phe Leu Val<br>300                      305                      310                  315 | 962 |
| ctc tac tac ttc ggc atg gcc agc tcg ctg tgg tgg gtg gtc ctc acg<br>Leu Tyr Tyr Phe Gly Met Ala Ser Ser Leu Trp Trp Val Val Leu Thr<br>                      320                      325                  330 | 1010 |
| ctc acc tgg ttc ctg gcc gcc ggc aag aag tgg ggc cac gag gcc atc<br>Leu Thr Trp Phe Leu Ala Ala Gly Lys Lys Trp Gly His Glu Ala Ile<br>            335                      340                      345 | 1058 |
| gaa gcc aac agc agc tac ttc cac ctg gca gcc tgg gcc atc ccg gcg<br>Glu Ala Asn Ser Ser Tyr Phe His Leu Ala Ala Trp Ala Ile Pro Ala<br>350                      355                      360 | 1106 |
| gtg aag acc atc ctg atc ctg gtc atg cgc agg gtg gcg ggg gac gag<br>Val Lys Thr Ile Leu Ile Leu Val Met Arg Arg Val Ala Gly Asp Glu | 1154 |

-continued

```
              365                 370                 375
ctc acc ggg gtc tgc tac gtg ggc agc atg gac gtc aac gcg ctc acc    1202
Leu Thr Gly Val Cys Tyr Val Gly Ser Met Asp Val Asn Ala Leu Thr
380                 385                 390                 395 ggc ttc gtg ctc att ccc ctg gcc tgc tac ctg gtc atc ggc acg tcc    1250
Gly Phe Val Leu Ile Pro Leu Ala Cys Tyr Leu Val Ile Gly Thr Ser
                400                 405                 410 ttc atc ctc tcg ggc ttc gtg gcc ctg ttc cac atc cgg agg gtg atg    1298
Phe Ile Leu Ser Gly Phe Val Ala Leu Phe His Ile Arg Arg Val Met
            415                 420                 425 aag acg ggc ggc gag aac acg gac aag ctg gag aag ctc atg gtg cgt    1346
Lys Thr Gly Gly Glu Asn Thr Asp Lys Leu Glu Lys Leu Met Val Arg
        430                 435                 440 atc ggg ctc ttc tct gtg ctg tac acc gtg ccg gcc acc tgt gtg atc    1394
Ile Gly Leu Phe Ser Val Leu Tyr Thr Val Pro Ala Thr Cys Val Ile
    445                 450                 455 gcc tgc tac ttt tac gaa cgc ctc aac atg gat tac tgg aag atc ctg    1442
Ala Cys Tyr Phe Tyr Glu Arg Leu Asn Met Asp Tyr Trp Lys Ile Leu
460                 465                 470                 475 gcg gcg cag cac aag tgc aaa atg aac aac cag act aaa acg ctg gac    1490
Ala Ala Gln His Lys Cys Lys Met Asn Asn Gln Thr Lys Thr Leu Asp
                480                 485                 490 tgc ctg atg gcc gcc tcc atc ccc gcc gtg gag atc ttc atg gtg aag    1538
Cys Leu Met Ala Ala Ser Ile Pro Ala Val Glu Ile Phe Met Val Lys
            495                 500                 505 atc ttt atg ctg ctg gtg gtg ggg atc acc agc ggg atg tgg att tgg    1586
Ile Phe Met Leu Leu Val Val Gly Ile Thr Ser Gly Met Trp Ile Trp
        510                 515                 520 acc tcc aag act ctg cag tcc tgg cag cag gtg tgc agc cgt agg tta    1634
Thr Ser Lys Thr Leu Gln Ser Trp Gln Gln Val Cys Ser Arg Arg Leu
    525                 530                 535 aag aag aag agc cgg aga aaa ccg gcc agc gtg atc acc agc ggt ggg    1682
Lys Lys Lys Ser Arg Arg Lys Pro Ala Ser Val Ile Thr Ser Gly Gly
540                 545                 550                 555 att tac aaa aaa gcc cag cat ccc cag aaa act cac cac ggg aaa tat    1730
Ile Tyr Lys Lys Ala Gln His Pro Gln Lys Thr His His Gly Lys Tyr
                560                 565                 570 gag atc cct gcc cag tcg ccc acc tgc gtg tga acagggctgg agggaagggc   1783
Glu Ile Pro Ala Gln Ser Pro Thr Cys Val
            575                 580 acagggcgc ccggagctaa gatgtggtgc ttttcttggt tgtgttttc tttcttcttc    1843 ttctttttt ttttttata aaagcaaaag agaaatacat aaaaaagtgt ttaccctgaa    1903
attcaggatg ctgtgataca ctgaaaggaa aaatgtactt aaagggtttt gttttgtttt    1963
ggttttccag cgaagggaag ctcctccagt gaagtagcct cttgtgtaac taatttgtgg    2023
taaagtagtt gattcagccc tcagaagaaa acttttgttt agagccctcc gtaaatatac    2083
atctgtgtat ttgagttggc tttgctaccc atttacaaat aagaggacag ataactgctt    2143
tgcaaattca agagcctccc ctgggttaac aaatgagcca tccccagggc ccaccccag    2203 gaaggccaca gtgctgggcg gcatccctgc agaggaaaga caggacccgg ggcccgcctc    2263 acccccagt ggatttggag ttgcttaaaa tagactctgg ccttcaccaa tagtctctct    2323
gcaagacaga aacctccatc aaacctcaca tttgtgaact caaacgatgt gcaatacatt    2383
tttttctctt tccttgaaaa taaaagaga acaagtatt tgctatata taaagacaac    2443 aaaagaaatc tcctaacaaa agaactaaga ggcccagccc tcagaaaccc ttcagtgcta    2503
cattttgtgg cttttaatg gaaaccaagc caatgttata gacgtttgga ctgatttgtg    2563
```

```
gaaaggaggg gggaagaggg agaaggatca ttcaaaagtt acccaaaggg cttattgact    2623
ctttctattg ttaaacaaat gatttccaca aacagatcag gaagcactag gttggcagag    2683
acactttgtc tagtgtattc tcttcacagt gccaggaaag agtggtttct gcgtgtgtat    2743
atttgtaata tatgatattt ttcatgctcc actattttat taaaaataaa atatgttctt    2803
taaaaaaa                                                            2811
```

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 155

```
ctcgaggttt cctcactaga caa                                             23
```

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 156

```
aatggttaaa ccgccctaaa taa                                             23
```

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 157

```
tccaccttct tcactgtcac c                                               21
```

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 158

```
taaaatacgg agtctgtagg ggc                                             23
```

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 159

```
attgaatagg cctgatcatc tga                                             23
```

<210> SEQ ID NO 160
<211> LENGTH: 23

<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 160
ataggagcgt agagtgcaca aag                                           23

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 161
atgacttaca gatcccccga c                                             21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 162
acagagcagg ggaagtcaca t                                             21

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 163
ctgcgcttct tcctatgcac ta                                            22

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 164
ttgttgtaga gcgggtgtga ct                                            22

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 165
cgctactttg tactcttgcc act                                           23

<210> SEQ ID NO 166
<211> LENGTH: 23
<212> TYPE: DNA

```
<213> ORGANISM: Artificial Sequence
<220> FEATURE:
<223> OTHER INFORMATION: Description of Artificial Sequence: synthetic
      oligonucleotide

<400> SEQUENCE: 166
acatgggata tggtactgac gac                                           23

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 167
gcgaggcgct catgaacaag t                                             21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 168
cacggccacc atgaagtagc a                                             21

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 169
gacacttgat gggctgaggt tc                                            22

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 170
taagtcaggg gtgggagttt ac                                            22

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 171
ctgcacgctg gtcttcctac t                                             21

<210> SEQ ID NO 172
<211> LENGTH: 21
<212> TYPE: DNA
<213> ORGANISM: Artificial Sequence
```

```
<220> FEATURE:
<223> OTHER INFORMATION: Description of Artificial Sequence: synthetic
      oligonucleotide

<400> SEQUENCE: 172
ccgatcttga ccatgagctt c                                              21

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 173
tcagaaaccc ttcagtgcta cat                                            23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 174
atacacacgc agaaaccact ctt                                            23

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 175
gtccccttct ccatctccag                                                20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 176
tatttgtgag ccagggcatt                                                20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 177
caacagcaag atgcatacca                                                20

<210> SEQ ID NO 178
<211> LENGTH: 20
<212> TYPE: DNA
<213> ORGANISM: Artificial Sequence
<220> FEATURE:
```

```
<223> OTHER INFORMATION: Description of Artificial Sequence: synthetic
      oligonucleotide

<400> SEQUENCE: 178
ggtgcagttg tttcccatcg                                              20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 179
caacagcaag atgcatacca                                              20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 180
ggcacagctc tttcccatca                                              20

<210> SEQ ID NO 181
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 181
ggggatcagc gtttgagtaa                                              20

<210> SEQ ID NO 182
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 182
taggccccac ctccttctat                                              20

<210> SEQ ID NO 183
<211> LENGTH: 30
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 183
tgcggatcca gagcagattg tactgagagt                                   30

<210> SEQ ID NO 184
<211> LENGTH: 29
<212> TYPE: DNA
<213> ORGANISM: Artificial
<220> FEATURE:
<223> OTHER INFORMATION: Description of Artificial Sequence: synthetic
``` oligonucleotide

<400> SEQUENCE: 184
ctctatctcg agtgaggcgg aaagaacca                                             29

<210> SEQ ID NO 185
<211> LENGTH: 40
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 185
tttaagcttg aagactattt ttacatcagg ttgttttct                                  40

<210> SEQ ID NO 186
<211> LENGTH: 37
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 186
tttaagcttg aagacacggt gtttcgtcct ttccaca                                    37

<210> SEQ ID NO 187
<211> LENGTH: 45
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 187
ccggaattcc agaccgtgca tcatgcagcg cccgggcccc cgcct                           45

<210> SEQ ID NO 188
<211> LENGTH: 27
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 188
aaaaagcttc acgcaggtgg gcgactg                                               27

<210> SEQ ID NO 189
<211> LENGTH: 29
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 189
aagtcgacac catgcagcgc ccgggcccc                                             29

<210> SEQ ID NO 190
<211> LENGTH: 26
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 190
tctcgaggac atccacgccg ggcgtg    26

<210> SEQ ID NO 191
<211> LENGTH: 29
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 191
aagtcgacta ctggagccgc gaggacaag    29

<210> SEQ ID NO 192
<211> LENGTH: 28
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 192
aactcgagtc acacgcaggt gggcgact    28

<210> SEQ ID NO 193
<211> LENGTH: 31
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 193
aactcgagtc agggcgactg ggcagggatc t    31

<210> SEQ ID NO 194
<211> LENGTH: 32
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 194
aactcgagtc aggaggtcca atccacatc cc    32

<210> SEQ ID NO 195
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 195
caccaacgct ggactgcctg atgttcaaga gacatcaggc agtccagcgt t    51

<210> SEQ ID NO 196
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 196
aaaaaacgct ggactgcctg atgtctcttg aacatcaggc agtccagcgt t    51

<210> SEQ ID NO 197
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 197
caccgactct gcagtcctgg cagttcaaga gactgccagg actgcagagt c    51

<210> SEQ ID NO 198
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 198
aaaagactct gcagtcctgg cagtctcttg aactgccagg actgcagagt c    51

<210> SEQ ID NO 199
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 199
caccgaagca gcacgacttc ttcttcaaga gagaagaagt cgtgctgctt c    51

<210> SEQ ID NO 200
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 200 aaagaagca gcacgacttc ttctctcttg aagaagaagt cgtgctgctt c    51

<210> SEQ ID NO 201
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 201
caccgtgcgc tgctggtgcc aactctcttg aagttggcac cagcagcgca c    51

<210> SEQ ID NO 202
<211> LENGTH: 51
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 202
aaaagtgcgc tgctggtgcc aacttcaaga gagttggcac cagcagcgca c                51

<210> SEQ ID NO 203
<211> LENGTH: 19
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 203
aacgctggac tgcctgatg                19

<210> SEQ ID NO 204
<211> LENGTH: 19
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 204
gactctgcag tcctggcag                19

<210> SEQ ID NO 205
<211> LENGTH: 19
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 205
gaagcagcac gacttcttc                19

<210> SEQ ID NO 206
<211> LENGTH: 19
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 206
gtgcgctgct ggtgccaac                19

<210> SEQ ID NO 207
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 207
tatcgggctc ttctctgtgc                20

<210> SEQ ID NO 208
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 208
gactgggcag ggatctcata                                                20

<210> SEQ ID NO 209
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 209
ctgcacgctg gtcttcctct                                                20

<210> SEQ ID NO 210
<211> LENGTH: 21
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 210
ccgatcttga ccatgagctt c                                              21

<210> SEQ ID NO 211
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 211
ttagctgtgc tcgcgctact                                                20

<210> SEQ ID NO 212
<211> LENGTH: 20
<212> TYPE: DNA
<213> ORGANISM: Artificial
<220> FEATURE:
<223> OTHER INFORMATION: Description of Artificial Sequence: synthetic
      oligonucleotide

<400> SEQUENCE: 212
tcacatggtt cacacggcag                                                20

<210> SEQ ID NO 213
<211> LENGTH: 12
<212> TYPE: PRT
<213> ORGANISM: Homo sapiens

<400> SEQUENCE: 213

Gly Val Asp Val Tyr Trp Ser Arg Glu Asp Lys Arg
1               5                   10

<210> SEQ ID NO 214
<211> LENGTH: 16
<212> TYPE: PRT
<213> ORGANISM: Homo sapiens

<400> SEQUENCE: 214

Glu Pro Thr Arg Gly Ser Gly Leu Phe Pro Pro Leu Phe Arg Pro Gln
1               5                   10                  15

<210> SEQ ID NO 215
<211> LENGTH: 18

```
<212> TYPE: PRT
<213> ORGANISM: Homo sapiens

<400> SEQUENCE: 215

Pro His Ser Ala Gln Glu His Pro Leu Lys Asp Gly Gly Pro Gly Arg
1               5                   10                  15

Gly Gly

<210> SEQ ID NO 216
<211> LENGTH: 14
<212> TYPE: PRT
<213> ORGANISM: Homo sapiens

<400> SEQUENCE: 216

Lys Asp Ile Gly Tyr Asn Met Thr Arg Met Pro Asn Leu Met
1               5                   10

<210> SEQ ID NO 217
<211> LENGTH: 12
<212> TYPE: PRT
<213> ORGANISM: Homo sapiens

<400> SEQUENCE: 217

Gln Arg Glu Ala Ala Ile Gln Leu His Glu Phe Ala
1               5                   10

<210> SEQ ID NO 218
<211> LENGTH: 14
<212> TYPE: PRT
<213> ORGANISM: Homo sapiens

<400> SEQUENCE: 218

Arg Gly Gly Cys Asp Asn Pro Gly Lys Phe His His Val Glu
1               5                   10

<210> SEQ ID NO 219
<211> LENGTH: 14
<212> TYPE: PRT
<213> ORGANISM: Homo sapiens

<400> SEQUENCE: 219

Glu Pro Thr Arg Gly Ser Gly Leu Phe Pro Pro Leu Phe Arg
1               5                   10

<210> SEQ ID NO 220
<211> LENGTH: 13
<212> TYPE: PRT
<213> ORGANISM: Homo sapiens

<400> SEQUENCE: 220

Gly Ser Gly Leu Phe Pro Pro Leu Phe Arg Pro Gln Arg
1               5                   10

<210> SEQ ID NO 221
<211> LENGTH: 14
<212> TYPE: PRT
<213> ORGANISM: Homo sapiens

<400> SEQUENCE: 221

Asp Glu Pro Thr Arg Gly Ser Gly Leu Phe Pro Pro Leu Phe
1               5                   10
```